(12) United States Patent
Feldman et al.

(10) Patent No.: US 11,152,118 B2
(45) Date of Patent: Oct. 19, 2021

(54) ELECTRONIC MEDICAL RECORD INTERACTIVE INTERFACE SYSTEM

(71) Applicant: InterfaceED Solutions, Inc., Millbrae, CA (US)

(72) Inventors: David Philip Feldman, Millbrae, CA (US); Joshua Howland Tamayo-Sarver, Los Gatos, CA (US); Khoa That Hoa Ton, San Jose, CA (US); Bidyut Parruck, Cupertino, CA (US)

(73) Assignee: INTERFACED SOLUTIONS, INC., Millbrae, CA (US)

( * ) Notice: Subject to any disclaimer, the term of this patent is extended or adjusted under 35 U.S.C. 154(b) by 1320 days.

(21) Appl. No.: 15/156,655

(22) Filed: May 17, 2016

(65) Prior Publication Data

US 2016/0259902 A1 Sep. 8, 2016

Related U.S. Application Data

(63) Continuation-in-part of application No. 13/187,394, filed on Jul. 20, 2011, now abandoned.

(Continued)

(51) Int. Cl.
*G16H 50/20* (2018.01)
*G16H 10/60* (2018.01)
(Continued)

(52) U.S. Cl.
CPC ............ *G16H 50/20* (2018.01); *G06Q 50/01* (2013.01); *G16H 10/60* (2018.01); *G16H 20/00* (2018.01); *G16H 40/63* (2018.01); *Y02A 90/10* (2018.01)

(58) Field of Classification Search
None
See application file for complete search history.

(56) References Cited

U.S. PATENT DOCUMENTS

| | | | |
|---|---|---|---|
| 5,267,155 A | 11/1993 | Buchanan | |
| 5,660,176 A | 8/1997 | Iliff | |

(Continued)

OTHER PUBLICATIONS

Sim et al, Clinical Decision Support Systems for the Practice of Evidence-based Medicine, J Am Med Inform Assoc, vol. 8, No. 6, 2001 (Year: 2001).*

(Continued)

*Primary Examiner* — Gregory Lultschik
(74) *Attorney, Agent, or Firm* — Ahmann Kloke LLP

(57) ABSTRACT

Automated diagnosis archetypes based on a complete list of library of medical illnesses are used dynamically to help prioritize health data that is relevant to a physician's medical diagnosis for a patient. A super plurality of diagnoses patient archetypes are narrowed to match a patient profile based on information collected from different sources. Based on dynamic physician's diagnosis, the patient profile is mapped to a subset of plurality of patient archetypes. An automated agent is employed to customize a user interface to emphasize order selections to support eliminating a false positive in the proper subset of the plurality of patient persons, a false negative in the plurality of patient archetypes, or to increase a predicted applicability of a set of patient archetypes to the patient profile. The subset of patient archetypes ranking is updated based on received order results. A confirmed dynamic physician diagnosis is made available.

16 Claims, 54 Drawing Sheets

Related U.S. Application Data

(60) Provisional application No. 61/366,135, filed on Jul. 20, 2010, provisional application No. 61/421,169, filed on Dec. 8, 2010.

(51) Int. Cl.
*G16H 40/63* (2018.01)
*G06Q 50/00* (2012.01)
*G16H 20/00* (2018.01)

(56) References Cited

U.S. PATENT DOCUMENTS

| | | | |
|---|---|---|---|
| 6,347,329 | B1 | 2/2002 | Evans |
| 6,767,325 | B2 | 7/2004 | Iliff |
| 6,849,045 | B2 | 2/2005 | Iliff |
| 7,197,492 | B2 | 3/2007 | Sullivan |
| 7,300,402 | B2 | 11/2007 | Iliff |
| 8,311,848 | B2 | 11/2012 | Subash |
| 2002/0077865 | A1 | 6/2002 | Sullivan |
| 2002/0170565 | A1 | 11/2002 | Walker |
| 2004/0172294 | A1 | 9/2004 | Dahlin |
| 2005/0033121 | A1* | 2/2005 | Modrovich ........... G06F 19/325 600/300 |
| 2005/0119917 | A1* | 6/2005 | Kim ...................... G06Q 50/22 705/2 |
| 2008/0208633 | A1 | 8/2008 | Navani |
| 2008/0250070 | A1 | 10/2008 | Abdulla |
| 2009/0125322 | A9 | 5/2009 | Dahlin |
| 2010/0131482 | A1 | 5/2010 | Linthicum |
| 2011/0082710 | A1 | 4/2011 | Subash |
| 2014/0136233 | A1* | 5/2014 | Atkinson ............... G16H 15/00 705/3 |
| 2015/0248536 | A1* | 9/2015 | Tawil .................... G16H 50/20 705/3 |
| 2015/0304368 | A1* | 10/2015 | Vaccari ................. G06F 1/3215 709/206 |
| 2016/0012194 | A1* | 1/2016 | Prakash ................ G16H 40/40 705/2 |
| 2016/0210427 | A1* | 7/2016 | Mynhier ................ G16H 50/20 |

OTHER PUBLICATIONS

Elstad, Emily A. et al., "What Do Physicians Gain (and Lose) with Experience? Qualitative Results from a Cross-National Study of Diabetes," Social Science & Medicine, vol. 70, No. 11, pp. 1728-1736, Jun. 2010.

Tamayo-Sarver, Joshua H. et al., "Racial and Ethnic Disparities in Emergency Department Analgesic Prescription," American Journal of Public Health, vol. 93, No. 12, pp. 2067-2073, Dec. 2003.

Tamayo-Sarver, Joshua H. et al., "Rapid Clinical Decisions in Context: A Theoretical Model to Understand Physicians' Decision-Making with an Application to Racial/Ethnic Treatment Disparities," Research in the Sociology of Health Care, vol. 23, pp. 183-213, 2005.

Tamayo-Sarver, Joshua H. et al., "The Effect of Race/Ethnicity and Desirable Social Characteristics on Physicians' Decisions to Prescribe Opiod Analgesics," Academic Emergency Medicine, vol. 10, No. 11, pp. 1239-1248, Nov. 2003.

Tamayo-Sarver, Joshua H. et al., "Variability in Emergency Physician Decisionmaking About Prescribing Opiod Analgesics," Annals of Emergency Medicine, vol. 43, No. 4, pp. 483-493, Apr. 2004.

* cited by examiner

Figure 1C-1:
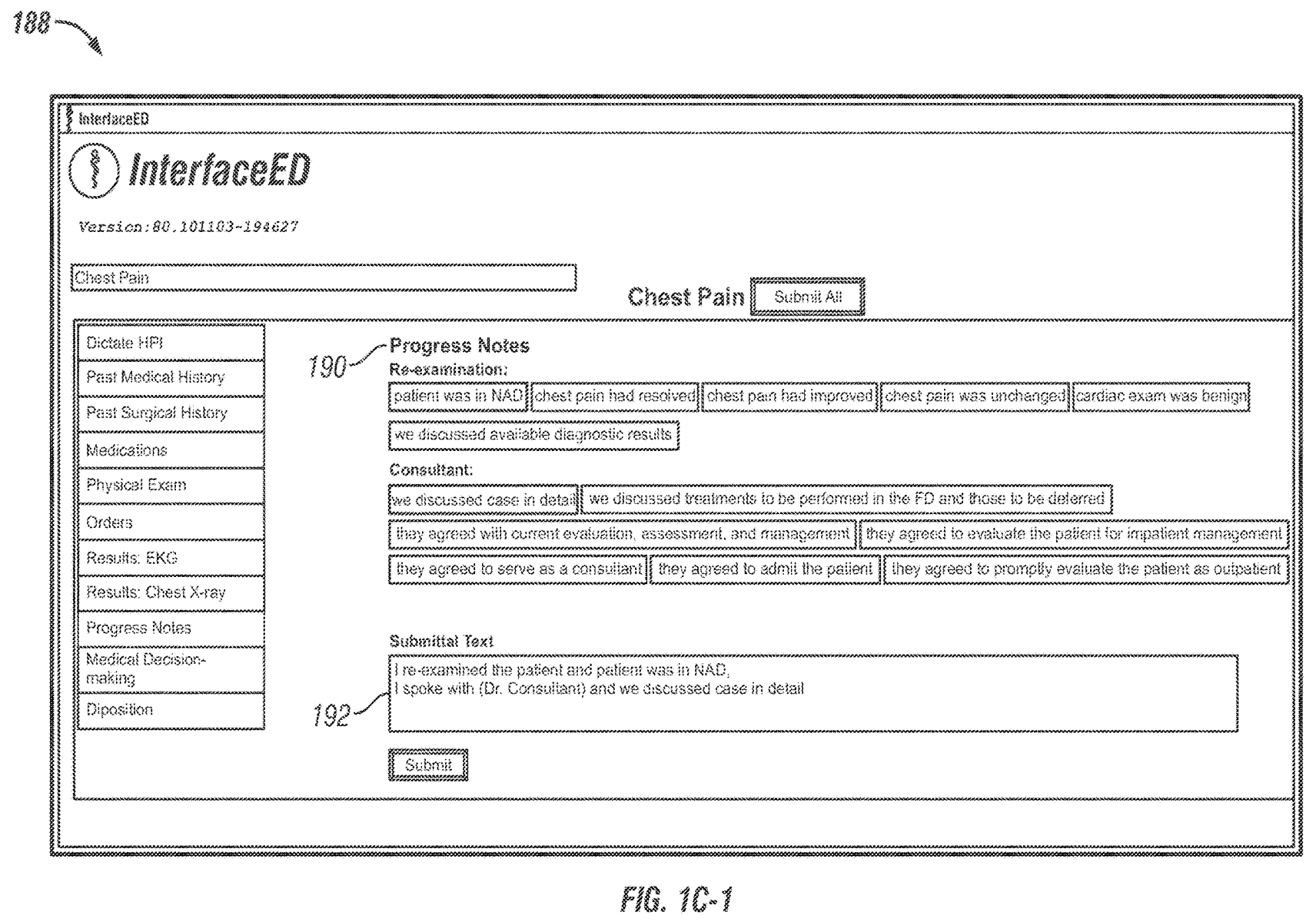

InterfaceED

Version: 80.101103-194627

Chest Pain | Chest Pain | Submit All

- Dictate HPI
- Past Medical History
- Past Surgical History
- Medications
- Physical Exam
- Orders
- Results: EKG
- Results: Chest X-ray
- Progress Notes
- Medical Decision-making
- Disposition 190 — Progress Notes:

Re-examination:
[patient was in NAD] [chest pain had resolved] [chest pain had improved] [chest pain was unchanged] [cardiac exam was benign]
[we discussed available diagnostic results]

Consultant:
[we discussed case in detail] [we discussed treatments to be performed in the ED and those to be deferred]
[they agreed with current evaluation, assessment, and management] [they agreed to evaluate the patient for inpatient management]
[they agreed to serve as a consultant] [they agreed to admit the patient] [they agreed to promptly evaluate the patient as outpatient]

Submittal Text:
I re-examined the patient and patient was in NAD. I spoke with (Dr. Consultant) and we discussed case in detail

192

[Submit]

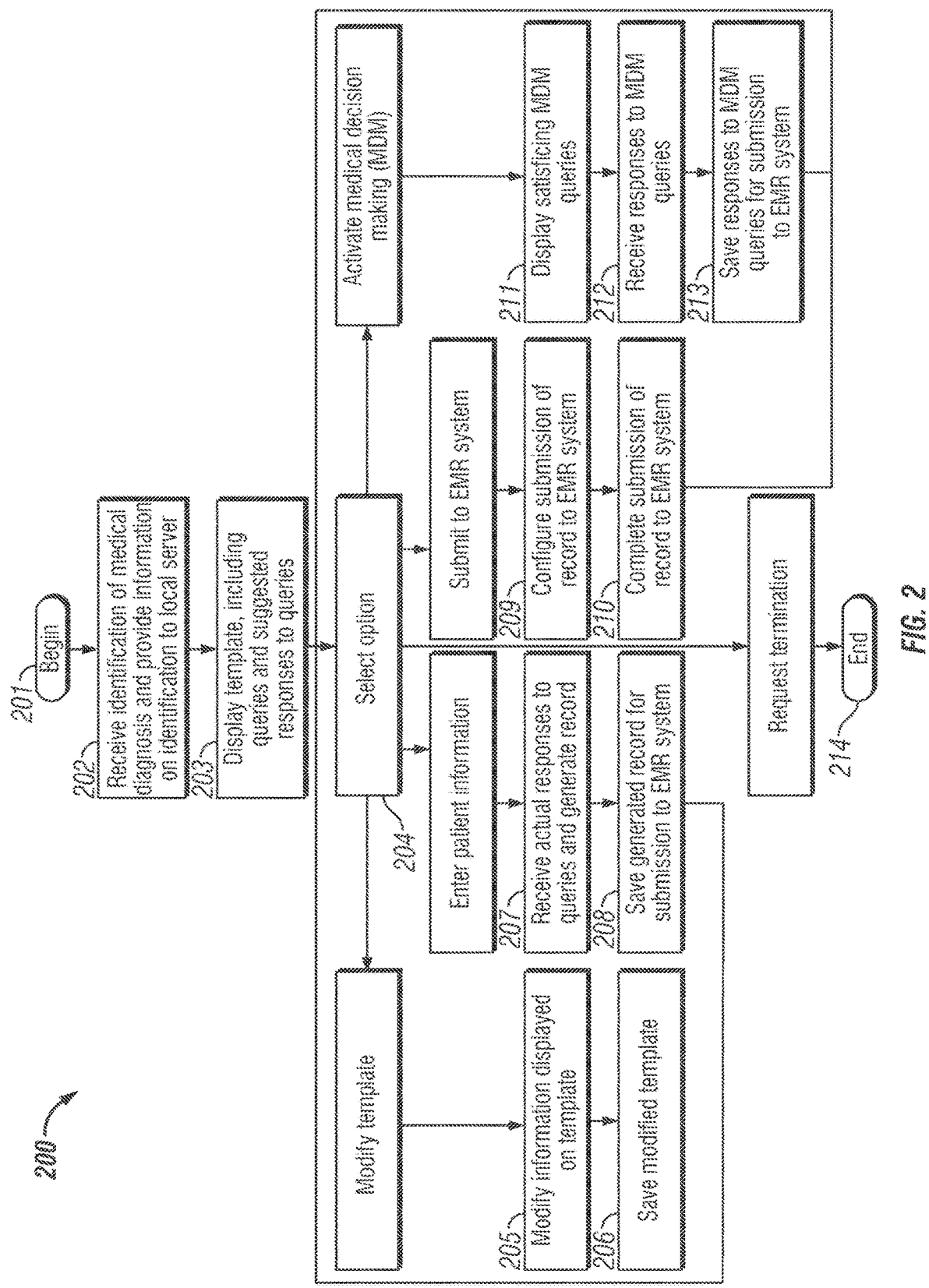

Pulmonary Embolus

Past Medical History — 342
Previous medical conditions:

| no dissectional aneurysm | no exertional syncope | no DVT/PE | no diabetes |
| no hypertension | no prior CVA | no connective tissue disease |

344  346

Submittal Text
Previous medical conditions : no prior CVA and no connective tissue disease.

312

Dictate HPI
Past Medical History
Past Surgical History
Medications
Physical Exam
Orders
Results: EKG
Results: Chest X-ray
Progress Notes
Medical Decision-making
Disposition Back to Modules List  Delete  Revert  Save  ☐ View Expanded  ☐ Edit Mode
Logout khoa

Pulmonary Embolus

Orders

Best practices:
CBC, Chem 7, Mag, AMI Panel, EKG, IV, Oxygen Monitor, Aspirin, NTG, PCXR — 306

Labs:
| CBC | Chem 7 | Mag | AMI Panel | D-dimer | BNP | PT/PTT | LFT | Lipase |

Orders:
| EKG | IV | Oxygen | Monitor | 500cc NS IV | 1L NS IV |

Medication:
| Aspirin | NTG | Morphine | Beta Blocker | ACE Inhibitor |

Imaging:
| PCXR | 2V CXR | CT Chest with IV contrast | CT Chest without IV contrast |

Submittal Text
Ordered CBC, Chem 7, Mag, AMI Panel, EKG, IV, Oxygen Monitor, Aspirin, NTG, PCXR. — 312

Sidebar:
- Dictate HPI
- Past Medical History
- Past Surgical History
- Medications
- Physical Exam
- Orders
- Results: EKG
- Results: Chest X-ray
- Progress Notes
- Medical Decision-making
- Disposition

[Back to Modules List] [Delete] [Revert] [Save]   ☐ View Expanded  ☐ Edit Mode
Logout khoa                                        ☐ Show debugging

Pulmonary Embolus

Disposition

Admission: (Patient is suitable for hospital admission)
- IV access established [ U T ]
- appropriate emergent interventions completed [ U T ]
- patient hemodynamically stable [ U T ]
- patient appropriate for inpatient management [ U T ]
- I personally discussed case with [Dr. Admission] and care was transferred [ U T ]

Discharge: (Patient is appropriate for outpatient management)
- patient has adequate social support [ U T ]
- Patient expressed understanding of detailed return precautions [ U T ]
- Patient expressed understanding of diagnostic uncertainty [ U T ]
- Patient with adequate outpatient follow-up and understands importance of follow-up [ U T ]
- Patient unlikely to benefit from hospitalization [ U T ]
- Patient able to return easily if condition deteriorates [ U T ]
- Patient checked out AMA [ U T ] — 402

Submittal Text

*FIG. 3K*

Pulmonary Embolus

Disposition

Admission: (Patient is suitable for hospital admission)

IV access established [ ] [ ] appropriate emergent interventions completed [ ] [ ]
patient hemodynamically stable [ ] [ ]
patient appropriate for inpatient management [ ] [ ]
I personally discussed case with [Dr. Admission] and care was transferred [ ]

Discharge: (Patient is appropriate for outpatient management)

patient has adequate social support [ ] [ ]
Patient expressed understanding of detailed return precautions [ ] [ ]
Patient expressed understanding of diagnostic uncertainty [ ] [ ]
Patient with adequate outpatient follow-up and understands importance of follow-up [ ] [ ]
Patient unlikely to benefit from hospitalization [ ] [ ]
Patient able to return easily if condition deteriorates [ ] [ ]

Submittal Text

Patient is appropriate for outpatient management; patient checked out AMA

Pulmonary Embolus

Medical Decision-making
Intermediate CP because:
Symptoms are concerning for angina or anginal equivalent | history of MI | peripheral of cerebral vascular disease
history of CABG | prior aspirin use | prolonged rest angina, now resolved, with moderate or high likelihood of CAD
rest angina more than 20 minutes, or relieved with rest or sublingual NTG | nocturnal angina
new onset or progressive angina in past two weeks | age > 70
EKG with T-wave changes, pathological Q waves, or ST depressions | intermediate range cardiac biomarkers Admitting because:
evaluate for cardiac damage | consideration for urgent cardiac risk stratification | cardiac monitoring
Serial cardiac markers and EKG Differential:
STEMI | NSTEMI | High-risk Chest Pain | Pericarditis or Myocarditis | Pericardial Effusion or Tamponade
Aortic Dissection | Thoracic Aortic Aneurysm | Pulmonary Embolism | Pneumonia (Mild) | Esophagitis
Esophageal Perforation | Mediastinitis | GERD | Musculoskeletal Chest Pain | Pleurisy | Bronchitis Submittal Text
Intermediate CP because: symptoms are concerning for angina or anginal equivalent.
Admitting because: evaluate for cardiac damage.
Differential:
Not STEMI because: STEMI D1.
Not Pneumonia (Mild) because: normal pulse oxygen saturation.
Not Bronchitis because: no productive cough, no wheezing, or abnormal pulse oxygen saturation.

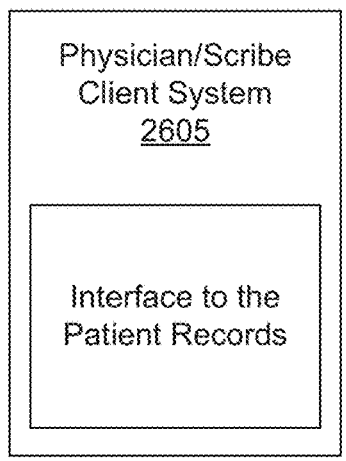
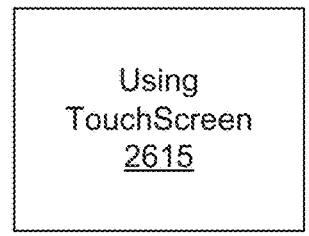
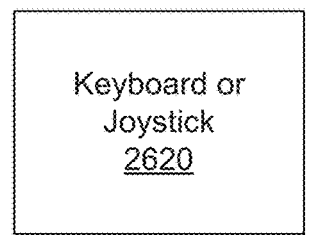
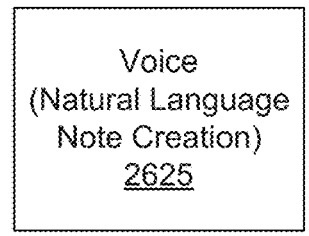
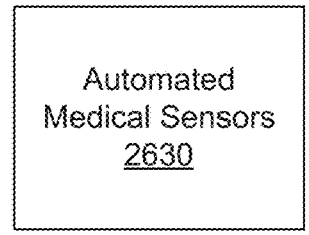
FIG. 26

ELECTRONIC MEDICAL RECORD INTERACTIVE INTERFACE SYSTEM

CROSS-REFERENCE TO RELATED APPLICATIONS

The present application is a continuation-in-part of U.S. patent application Ser. No. 13/187,394, filed Jul. 20, 2011, which claims the benefit of priority under 35 U.S.C. § 119 of U.S. Provisional Patent Application No. 61/366,135, filed Jul. 20, 2010, and U.S. Provisional Patent Application No. 61/421,169, filed Dec. 8, 2010, all of which are hereby incorporated by reference herein.

BACKGROUND

Healthcare systems that use electronic medical records provide large volumes of data relating to patient who have been evaluated at some point in their lives for a medical condition. Health care professionals (physicians, physicians assistants, nurses, medical support staff, emergency medical personnel, dentists, etc.) evaluating a patient may not have the time or resources to analyze all the information that is available on their computer systems. As an example, a health care professional reviewing a patient's medical records (electronic or otherwise) before diagnosing/treating the patient for a medical condition may be confronted with large volumes of data in the form of the patient's history of medical conditions, diagnoses, medications, treatments, etc.

In forming a diagnosis and/or treatment plan, a health care professional may need to review background medical materials from medical texts, medical reference manuals, Internet sources, etc. and/or information taken from other patients with similar or dissimilar conditions. The health care professional may be faced with cumbersome data structures of electronic medical records that are not in sync with real-life applications. As an example, electronic medical records may reside in a format that the health care professional cannot easily review on a personal computing device. Health care providers may be reluctant and/or resistant to using a system that requires significant expenditure of time away from patient care.

SUMMARY

Systems, methods, and computer-readable media described herein may provide computer-implemented tools to assist health care professionals in forming diagnoses and/or treatment plans for medical conditions. In various implementations, the systems, methods, and/or computer-readable media described herein may support automated agents that provide health care with automated diagnosis patient archetypes that the health care professionals can use as the basis of diagnosing and/or treating medical conditions. The automated agents may provide the health care professionals with a user interface that allows them to determine whether or not a patient's medical condition is sufficiently to medical conditions associated with an automated diagnosis patient archetype. In some implementations, the automated agents may automate treatment plans, such as supporting orders for prescriptions, laboratory tests, radiology orders, etc. The automated agents may further allow a health care professional to use information related to a confirmed or unconfirmed medical condition as the basis of later diagnoses/treatments.

BRIEF DESCRIPTION OF THE DRAWINGS

FIGS. 1B-1, 1B-2, 1C-1, 1C-2, 1D-1, and 1D-2 are exemplary screenshots illustrating the association between a user interface of the disclosed system and a user interface of an underlying EMR system.

FIG. 2 is an exemplary process for providing information on a medical diagnosis using the architecture of FIG. 1A.

FIG. 24 depicts an example of a customized graphical user interface displaying patient profile.

FIG. 26 depicts an example of different types of user interfaces used in the automated diagnoses system.

DETAILED DESCRIPTION

Figure 1A:
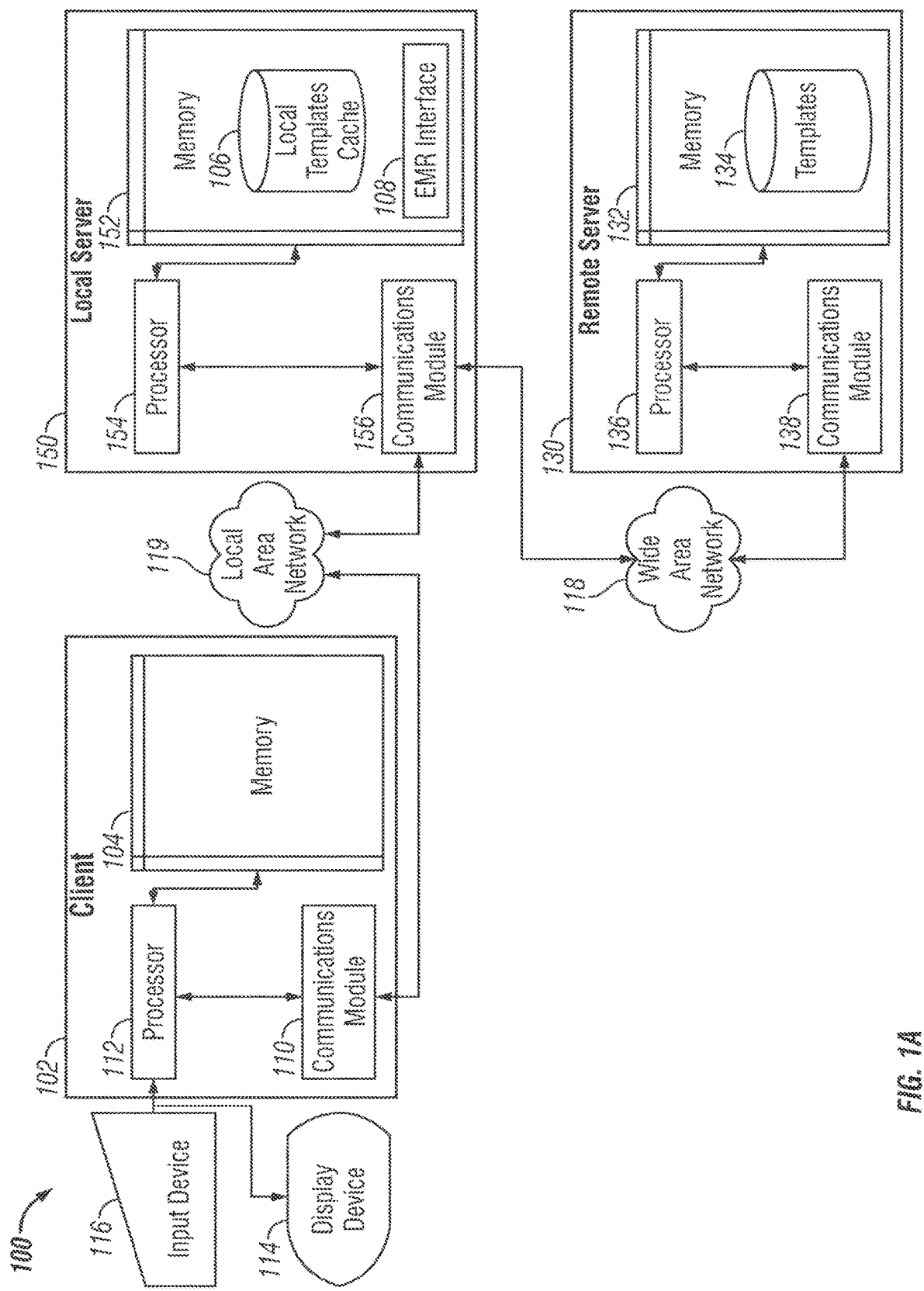
FIG. 1A illustrates an exemplary architecture for providing information on a medical diagnosis according to certain implementations.

FIG. 1A illustrates an exemplary architecture for providing information on a medical diagnosis according to certain implementations. The architecture 100 includes a client 102, a local server 150, and a remote server 130. The client 102 is connected to the local server 150 over a local area network 119, and the local server 150 is connected to the remote server 130 over a wide area network 118. The local area network 119 can be, for example, a private communications network, and the wide area network 118 can be, for example, the Internet.

The remote server 130 includes a processor 136, communications module 138, and memory 132, the memory 132 including a plurality of templates 134. The remote server 130 is configured for communication over the wide area network 118 (e.g., with local server 150) using a communications module 138. The communications module 138 can be, for example, a modem or Ethernet card. The processor 136 of the remote server 130 is configured to execute instructions, such as instructions physically coded into the processor 136, instructions received from software in memory 132, or a combination of both. For example, the processor 136 of the remote server 130 is configured to provide templates 134 to the local server 150, such as when the local server 150 sends a request for the templates 134 over the wide area network 118.

The local server 150 includes a processor 154, a communications module 156, and a memory 152, the memory including a local templates cache 106 and an EMR interface 108. The local templates cache 106 is configured to receive either a subset of the templates 134 stored on the remote server 130, or all of the templates stored on the remote server 130. In certain implementations, the templates stored in the local templates cache 106 are updated with the templates 134 stored on the remote server 130. The processor 136 of the local server 150 is configured to execute instructions, such as instructions physically coded into the processor 136, instructions received from software in memory 132, or a combination of both.

The client 102 includes a processor 112, a communications module 110, a memory 104, an input device 116, and a display device 114. The processor 112 of the client 102 is configured to execute instructions, such as instructions physically coded into the processor 112, instructions received from software in memory, or a combination of both. For example, the processor 136 is configured to display a template, including its queries and suggested responses, using the display device 114, and is configured to receive selections of suggested responses or manual user input using the input device 116. Exemplary display devices 114 include CRT or LCD monitors, and exemplary input devices 116 include keyboards, mice, touch screens, trackballs, and microphones.

The templates 134 stored in either the memory 132 of the remote server 130 and/or the local templates cache 106 of the local server 150 are each based on at least one medical diagnosis. As discussed herein, a medical diagnosis is an identification of a medical disease or injury, or an identification of a complaint of a medical disease or injury. Exemplary medical diagnoses include, but are not limited to, pulmonary embolus, pneumonia, appendicitis, diverticulitis, urinary tract infection, pyelonephritis, myocardial infarction, aortic dissection, cerebral vascular accident, transient ischemic attack, meningitis, and encephalitis. In certain implementations, a template may be temporarily stored in the memory 104 of the client 102 while it is displayed by the client. The templates are stored as data files. In certain implementations, each template includes at least one query associated with the medical diagnosis, at least one suggested response to the query, and an input field configured to receive an actual response to the query. As discussed herein, a query includes, but is not limited to, a prompt indicating a response is requested, clinical and/or other pertinent information entered in the input fields by the user, clinical and/or other pertinent information entered in the input fields by the automated response of the program, diagnostic and/or therapeutic interventions as related to the diagnosis, critical decision making as related to the diagnosis, medical decision making as related to the diagnosis, satisficing of alternative diagnoses, discussion of further medical care and clinical disposition. The suggested response is configured to be selected by a user (e.g., provider) for entry into the input field. The suggested response is based on, for example, at least one of a previously provided response to a query (e.g., because much of the documentation required by a patient encounter is constant and predictable), a user-defined suggested response (e.g., what a user believes a suggested response to the query should be), a facility policy (e.g., a response in accordance with the policies of the healthcare facility of the user), and a best practice (e.g., in accordance with the best practices of the healthcare facility of the user or standard of practice as defined by a larger healthcare body, such as the American College of Emergency Physicians, American Board of Emergency Medicine, American Medical Association, California Medical Association and equivalent state medical associations, American Hospital Association, American College of Cardiology, Association of American Medical Colleges, Accreditation Council for Continuing Medical Education, Accreditation Council for Graduate Medical Education, American Academy of Neurology, American Academy of Pediatrics, American Academy of Orthopedic Surgeons, American College of Surgeons, American Dental Association, American Health Care Association, American Health Lawyers Association). In certain implementations, the suggested responses are based on user-defined suggested responses that are received from various clients 102 that are connected over the wide area network 118 (e.g., from different healthcare facilities that are subscribed to a service that includes providing the templates 134).

In certain implementations, each of the templates 134 includes a plurality of queries associated with a medical diagnosis, at least one suggested response to each of the queries, and an input field, for each of the queries, configured to receive an actual response for each of the queries. The suggested response is configured to be selected by the user for entry into each of the input fields. In certain implementations, each template comprises a plurality of suggested responses to each query, and each of the suggested responses is configured to be selected by the user for entry into the input field. For example, one suggested response can be entered into each input field. In certain implementations, the suggested responses are configured to be selected by the user for simultaneous entry into the input field. For example, several suggested responses can be entered into each input field. The input field is configured to receive any text entered by the user, and is not limited to receiving suggested responses selected by the user. For example, the user can click on the input field using a mouse and begin typing text of his/her choosing. Exemplary templates 134 are illustrated in FIGS. 3A, 3B, 3C, 3D, 3E, 3F, 3G, 3H, 3I, 3J, 3K, 3L, 3M, 3N, 3O, 3P, and 3Q and will be described in further detail with reference to FIGS. 3A, 3B, 3C, 3D, 3E, 3F, 3G, 3H, 3I, 3J, 3K, 3L, 3M, 3N, 3O, 3P, and 3Q.

In certain implementations, each of the templates 134 is configured to include recently published information related to the medical diagnosis associated with the template. The recently published information can be retrieved, for example, from a medical database or website over the Internet (i.e., the wide area network 118). For example, if a selected template is associated with a diagnosis of pulmonary embolus, the selected template may include recent information (e.g., within the last 1, 2, 3, 6, or 12 months) on new surgical or drug treatments for pulmonary embolus.

In certain implementations, the design of each of the templates 134 is configured to be customizable. For example, each template can be customized based on a user's most often used preferences, intuitive design choices, site or facility look (e.g., logos and colors), and best practices.

The processor 112 of the client 102 is configured to receive, from a user, an input identifying a medical diagnosis and provide a template to be displayed on the display device 114 based on the identified medical diagnosis. The template can either be provided from the local templates cache 106 of the local server 150, or over the wide area network 118 from the templates 134 stored on the remote server 130. The processor 112 of the client 102 is also configured to receive responses to the queries in the template (e.g., via input device 116) and generate a record (e.g., that includes both the queries from the template and the received responses). The client 102 may thereafter store the record in memory 104 and/or send the record to the local server 150 over the local area network 119. The local server 150 is configured to use the EMR interface 108 in its memory 152 to convert the record into a format compatible with an EMR system, such as an EMR system in communication with the local server 150 for storing patient records for patients at a healthcare facility associated with the user. The EMR interface 108 allows the record to further interface with different types of EMR systems, such as an EDIS system, such as by converting the completed template into an EMR for storage in an EMR system. Therefore, compatibility between the completed template and an EMR system is addressed by the use of an appropriately configured EMR interface 108.

In certain implementations, the EMR interface 108 is configured to work with preexisting EMRs (e.g., including EMR systems) through the use of existing interface mechanisms, including, but not limited to, Application Program Interfaces (API) for the EMRs and the EMRs' own graphical user interfaces. In such cases, the EMR interface 108 can be considered to make the disclosed system "universally applicable" or "universally compatible" with such pre-existing EMRs. Information may be provided from the EMR to the EMR interface 108 synchronously, asynchronously, serially, and/or in parallel with other processes. In implementations of the disclosed system that use APIs, programmatic calls are generated by the EMR interface 108 that pass information to and from the EMR. Alternatively, if the provider does not want to use the disclosed system to enter information into the EMR, then the provider can enter information into the EMR directly, such as by disabling the EMR interface 108.

In certain implementations of the disclosed system that use GUIs to interface with the underlying EMR, such as with underlying EMRs that do not provide APIs, the EMR interface 108 implements screen scraping. The screen scraping interaction includes reading the screen of the underlying EMR, determining how to interact with the read screen, and executing keyboard, mouse, and other input instructions to provide information to the underlying EMR screen automatically using the EMR interface 108. For example, in certain implementations, the mouse instructions include cursor movements and clicks. The keyboard instructions include sending keystrokes, including shortcuts like cut and paste as allowed by an underlying operating system. In certain implementations, the EMR interface 108 implements image processing and/or recognition. Image processing and/or recognition includes optically visualizing data on a tangible medium, recognizing the content of the data on the tangible medium, and converting it to provide information to the underlying EMR screen using the EMR interface 108. For example, in certain implementations, optical character recognition may be applied to convert scanned images of handwritten, typewritten or printed text into machine-encoded text.

Figure 1B-1:
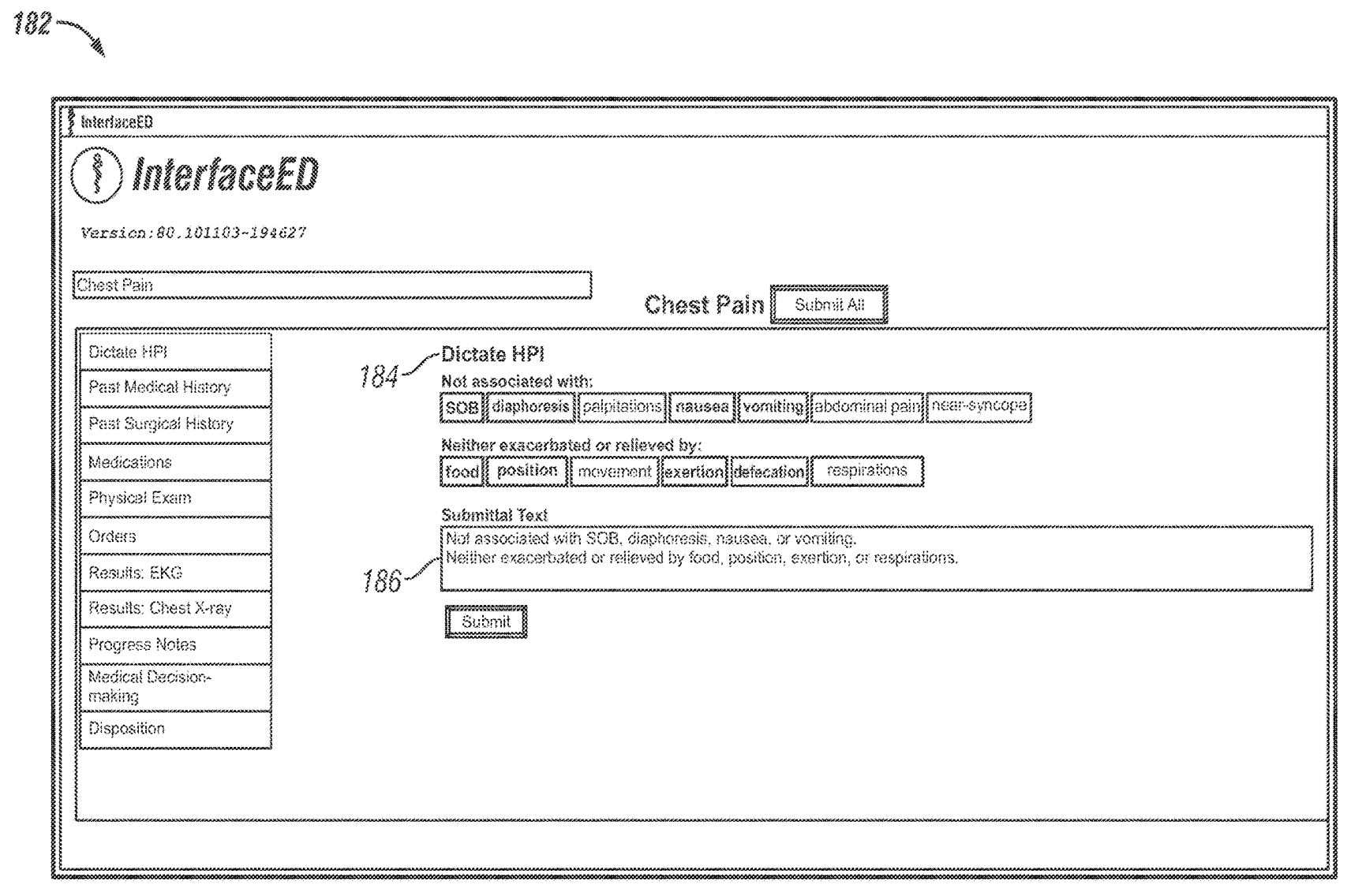
Figure 1B-2:
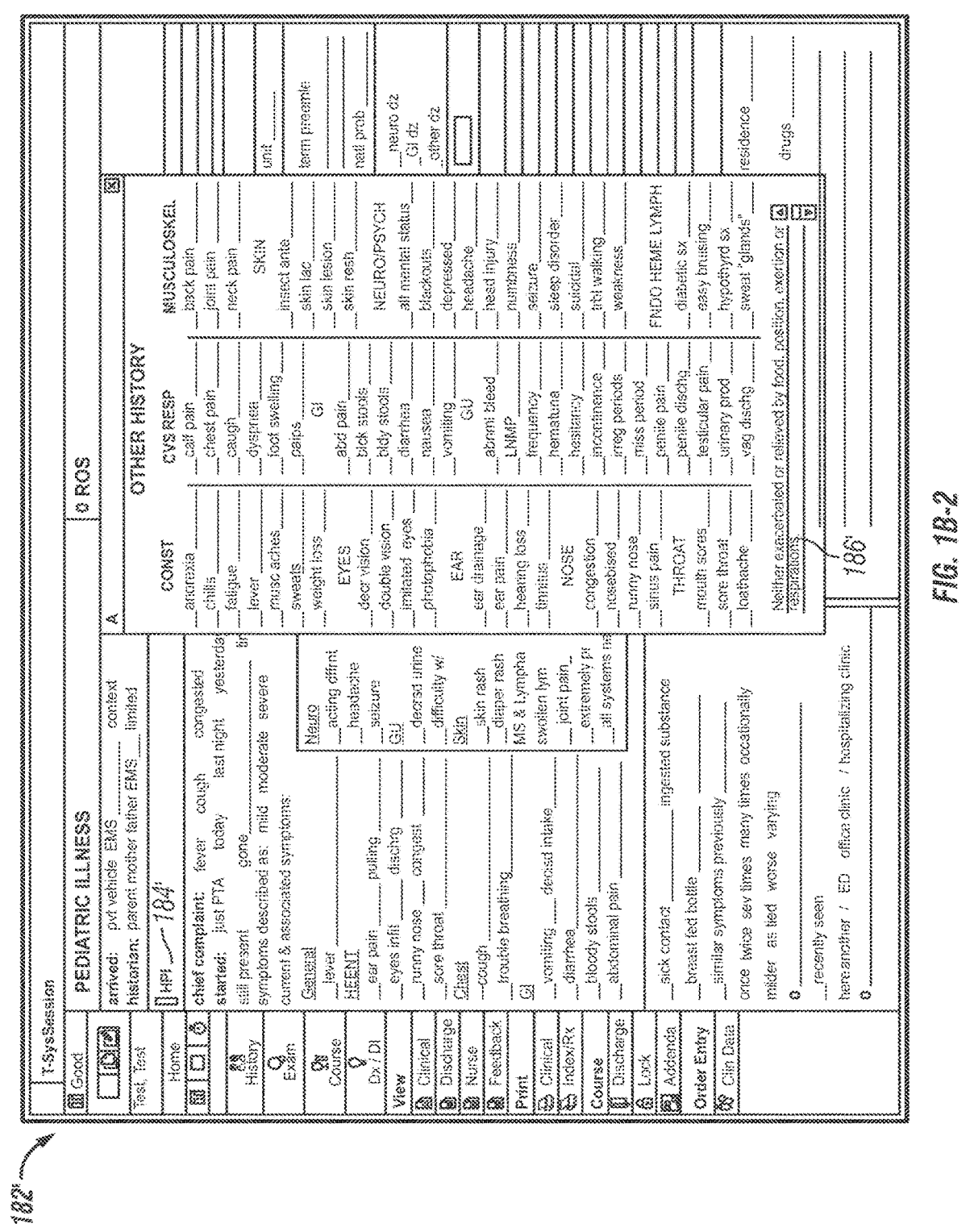

FIGS. 1B-1 and 1B-2 illustrate an exemplary screenshot 182 of a user interface for entering a history of patient information (HPI) using the disclosed system and an exemplary screenshot 182' of a user interface for entering a HPI using a conventional EMR system. The EMR interface 108 is configured to read the screen 182' of the underlying conventional EMR system and make associations with the disclosed system. For example, the EMR interface 108 is configured to associate the "Dictate HPI" query 184 of the disclosed system with the "HPI" entry point 184' of the underlying EMR system. Similarly, the EMR interface 108 is configured to associate the "Dictate HPI" input field 186 of the disclosed system with the "Other History" input field 186' of the underlying EMR system.

Figure 1C-2:
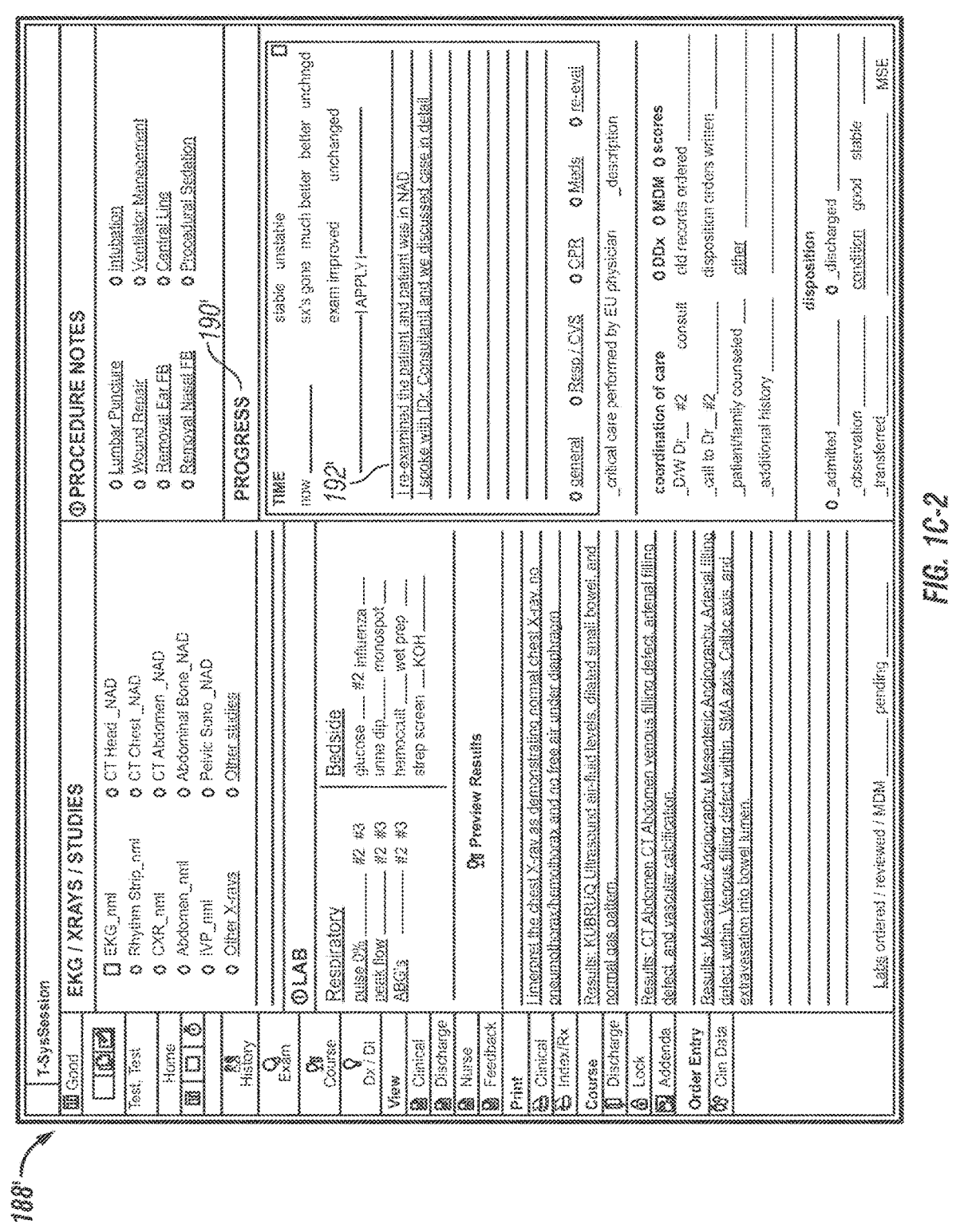

FIGS. 1C-1 and 1C-2 illustrate an exemplary screenshot 188 of a user interface for entering progress notes using the disclosed system and an exemplary screenshot 188' of a user interface for entering progress notes using a conventional EMR system. The EMR interface 108 is configured to read the screen 188' of the underlying conventional EMR system and make associations with the disclosed system. For example, the EMR interface 108 is configured to associate the "Progress Notes" query 190 of the disclosed system with the "Progress" entry point 190' of the underlying EMR system. Similarly, the EMR interface 108 is configured to associate the "Progress Notes" input field 192 of the disclosed system with the input field 192' of the underlying EMR system.

Figure 1D-2:
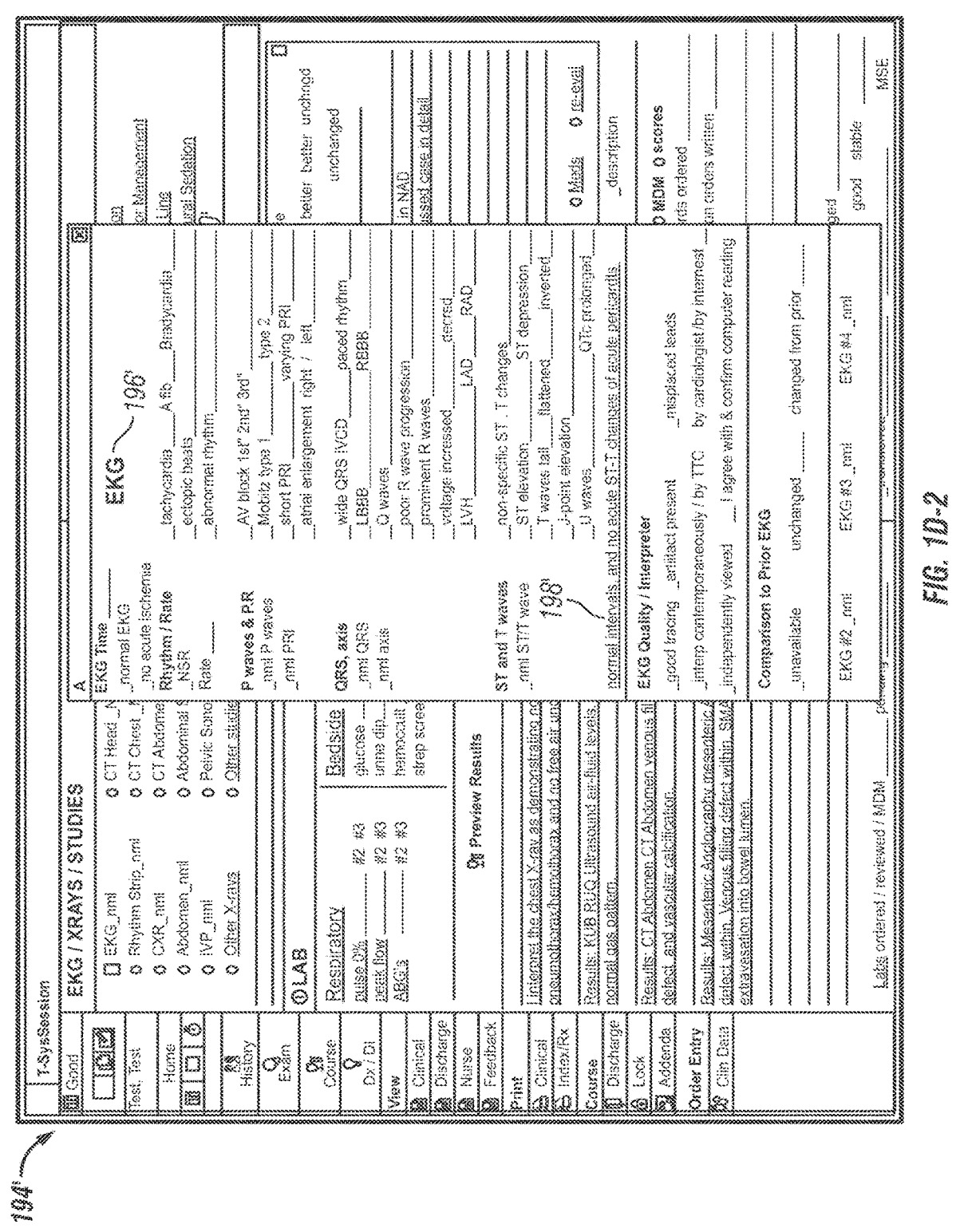

FIGS. 1D-1 and 1D-2 illustrate an exemplary screenshot 194 of a user interface for entering electrocardiogram (EKG) results using the disclosed system and an exemplary screenshot 194' of a user interface for entering EKG results using a conventional EMR system. The EMR interface 108 is configured to read the screenshot 194' of the underlying conventional EMR system and make associations with the disclosed system. For example, the EMR interface 108 is configured to associate the "Results: EKG" query 196 of the disclosed system with the "EKG" entry point 196' of the underlying EMR system. Similarly, the EMR interface 108 is configured to associate the "Results: EKG" input field 198 of the disclosed system with the input field 198' of the underlying EMR system.

In certain implementations, the processor 150 of the remote server 130 is similarly configured to receive, from a user, and over the local area network 119 and the wide area network 118, an input identifying a medical diagnosis. In certain implementations, the processor 150 of the remote server 130 is configured to provide a template to be displayed on the display device 114 of the client 102 based on the identified medical diagnosis. The template is provided from the templates 134 stored on the remote server 130. For example, if the appropriate template for the identified medical diagnosis is not available in the local templates cache 106, the appropriate template is provided from the templates 134 stored in the memory 132 of the remote server 130.

The architecture 100 of FIG. 1A is exemplary; other architectures are contemplated and can be used with the disclosure. For example, in certain implementations, the EMR interface 108 can be stored in the memory 104 of the client 102, thereby allowing the client 102 to process the generated records. By way of another example, in certain implementations, the EMR interface 108 and local templates cache 106 can be stored in the memory 104 of the client 102, thereby removing the need for the local server 150. In such cases, the communications module 102 of the client 102 can be directly connected to the communications module 138 of the remote server 130 over the wide area network 118.

FIG. 2 is an exemplary process 200 for providing information on a medical diagnosis using the architecture 100 of FIG. 1A. The process 200 begins from step 201 to step 202, where an identification of a medical diagnosis is received (e.g., at the client 102) and information on the identified medical diagnosis is provided (e.g., to the local server 150). In step 203, a template is displayed (e.g., from the local templates cache 106 and/or from local server 150) that is based on the identified medical diagnosis. In step 204, one of five options is selected.

If the user chooses to modify the template in step 204, then the modified template is displayed in step 205. At this step, the template can be modified 134 by the user editing the suggested responses (as will be described in more detail with reference to FIGS. 3I-3L). The modified template is saved (e.g., locally in the local templates cache 106 of the local server 150 and/or remotely along with the templates 134 on the remote server 130) in step 206. The process 200 then returns to step 204.

If the user chooses to enter patient information in step 204, then the process 200 proceeds to step 207 in which actual responses to queries in the template are received, and a record is generated. In step 208, the generated record is saved for later submission to the EMR system. The process 200 then returns to step 204.

If the user chooses to activate the Medical Decision Making process (e.g., Medical Decision Making queries) in step 204, then the process 200 proceeds to step 211. Medical Decision Making satisficing queries are displayed in step 211 and responses to the queries are received in step 212. As discussed herein, satisficing is a decision-making strategy that attempts to meet criteria for adequacy, rather than to identify an optimal solution. The responses are saved in step 213 for later submission to the EMR system. The process 200 then returns to step 204.

If the user chooses to submit a generated record (including responses to Medical Decision Making queries) to the EMR system in step 204, then the process 200 proceeds to step 209 in which the record submission is configured for the EMR system. For example, the user can choose to have the record submitted serially with other generated records (and/or individual response to queries), in parallel with other generated records, or manually. In step 201, the record is submitted to the EMR system using the EMR interface 108 based on the configuration of step 209. The submission of record to EMR is completed at step 210, the process 200 then returns to step 204.

Figure 3A:
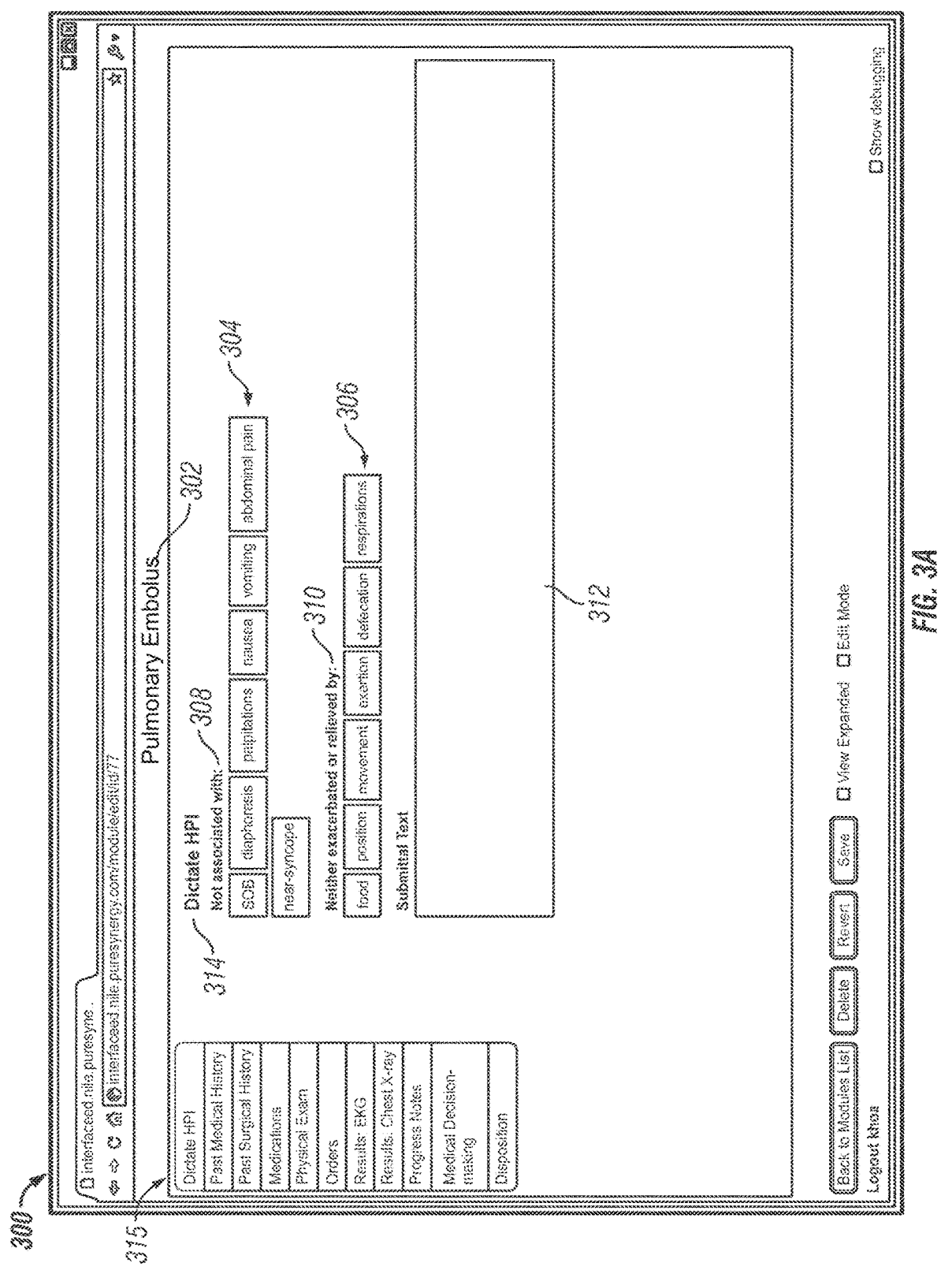
Figure 3B:
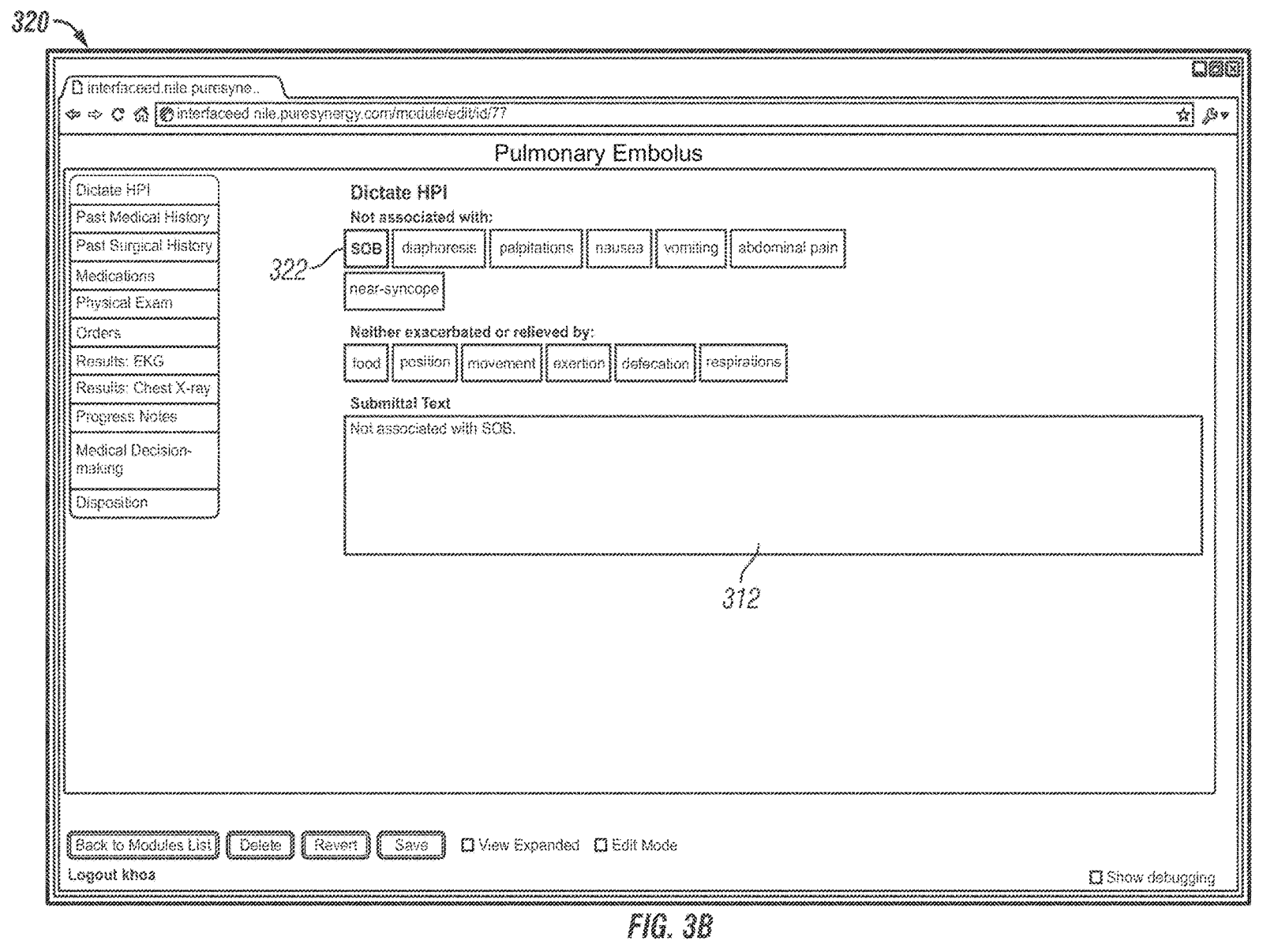
Figure 3C:
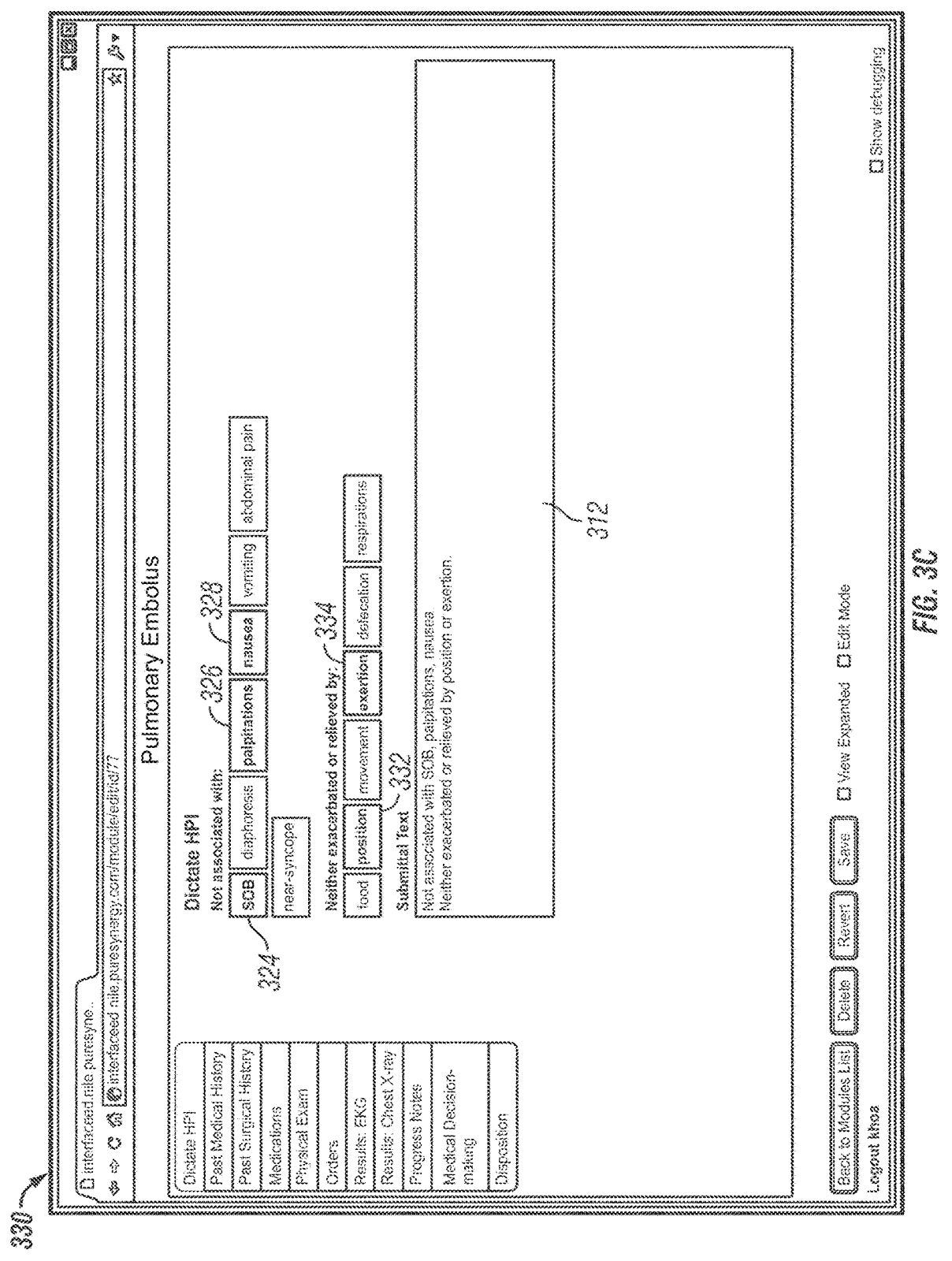
Figure 3E:
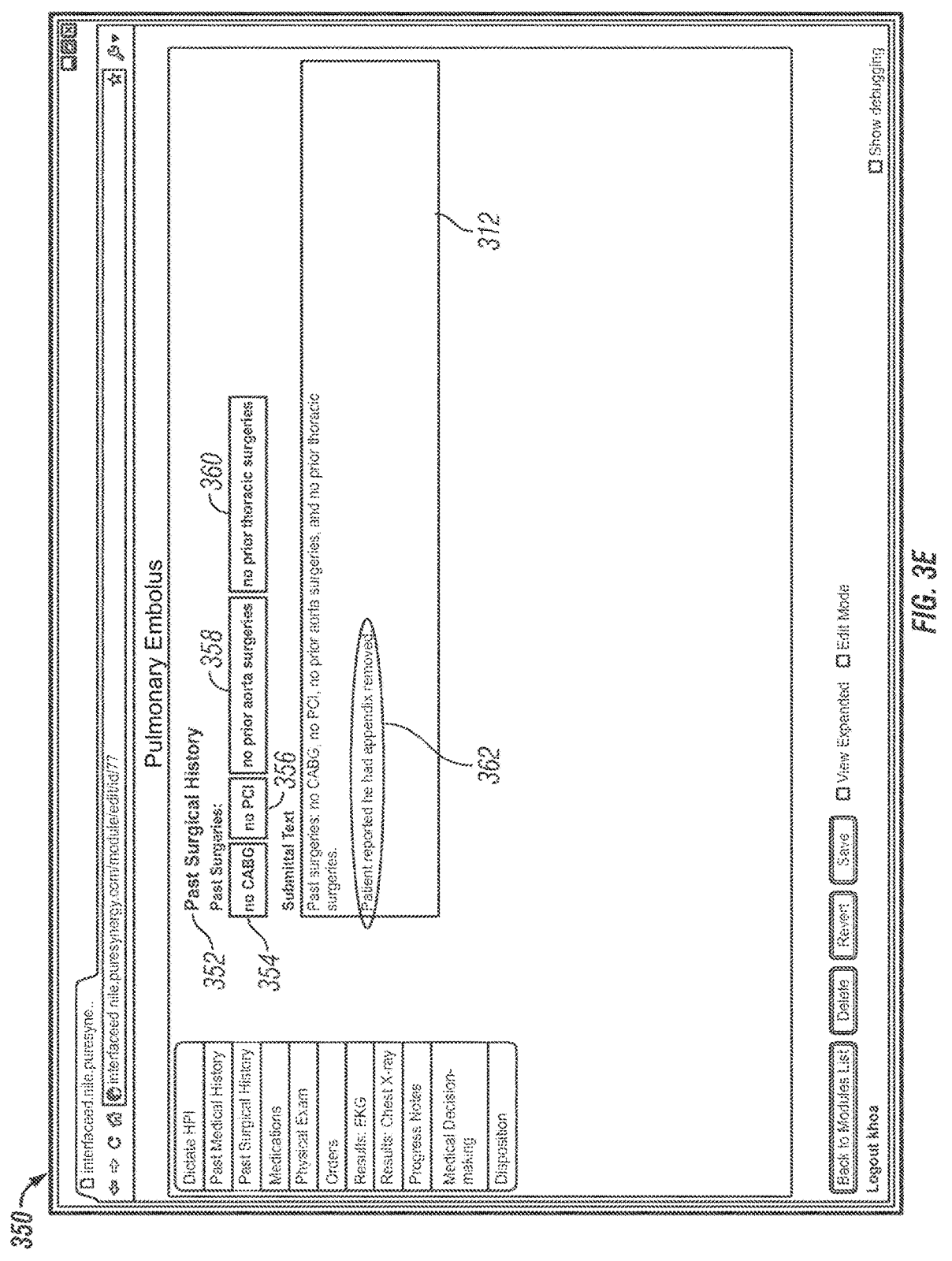
Figure 3F:
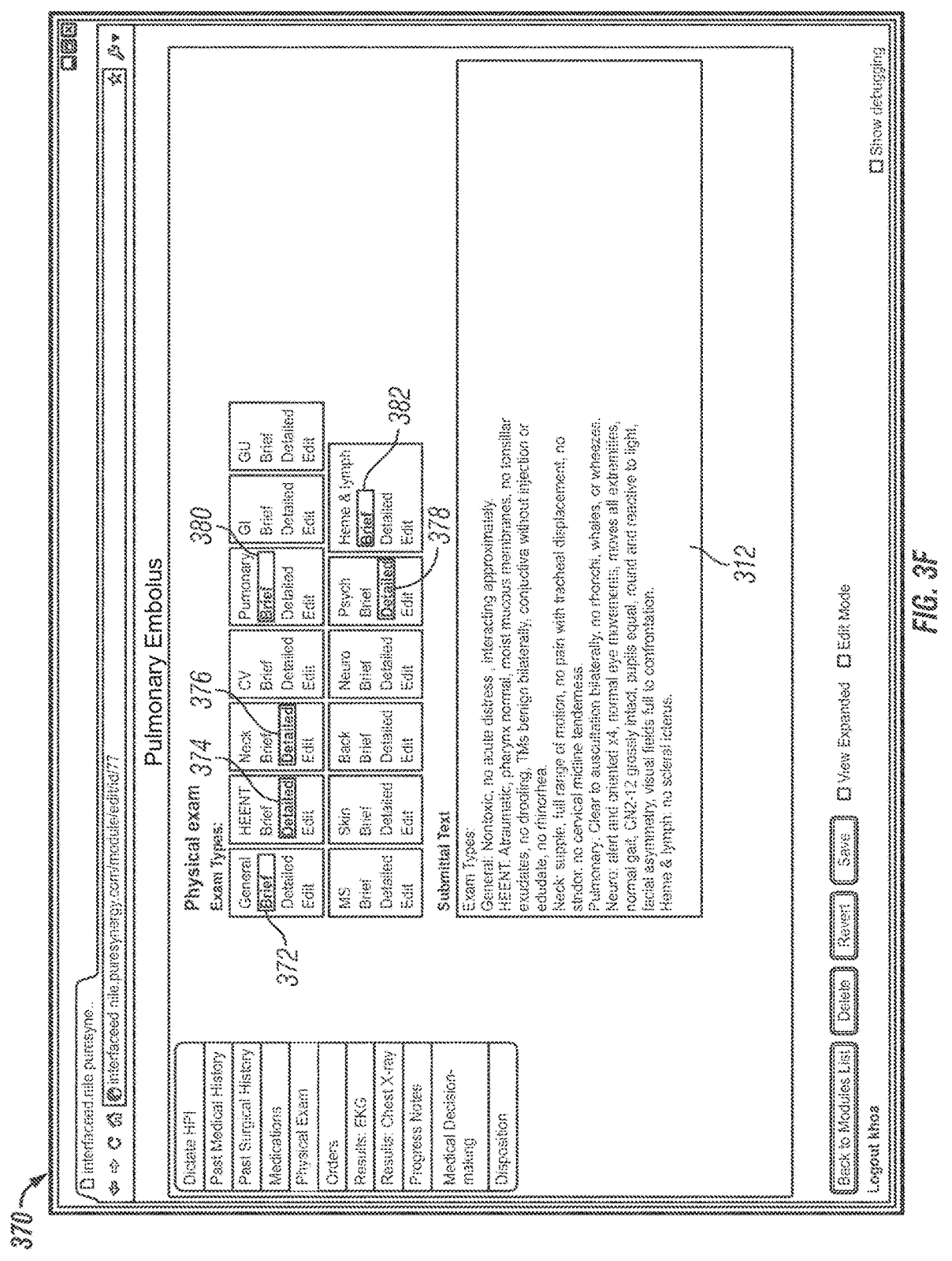
Figure 3H:
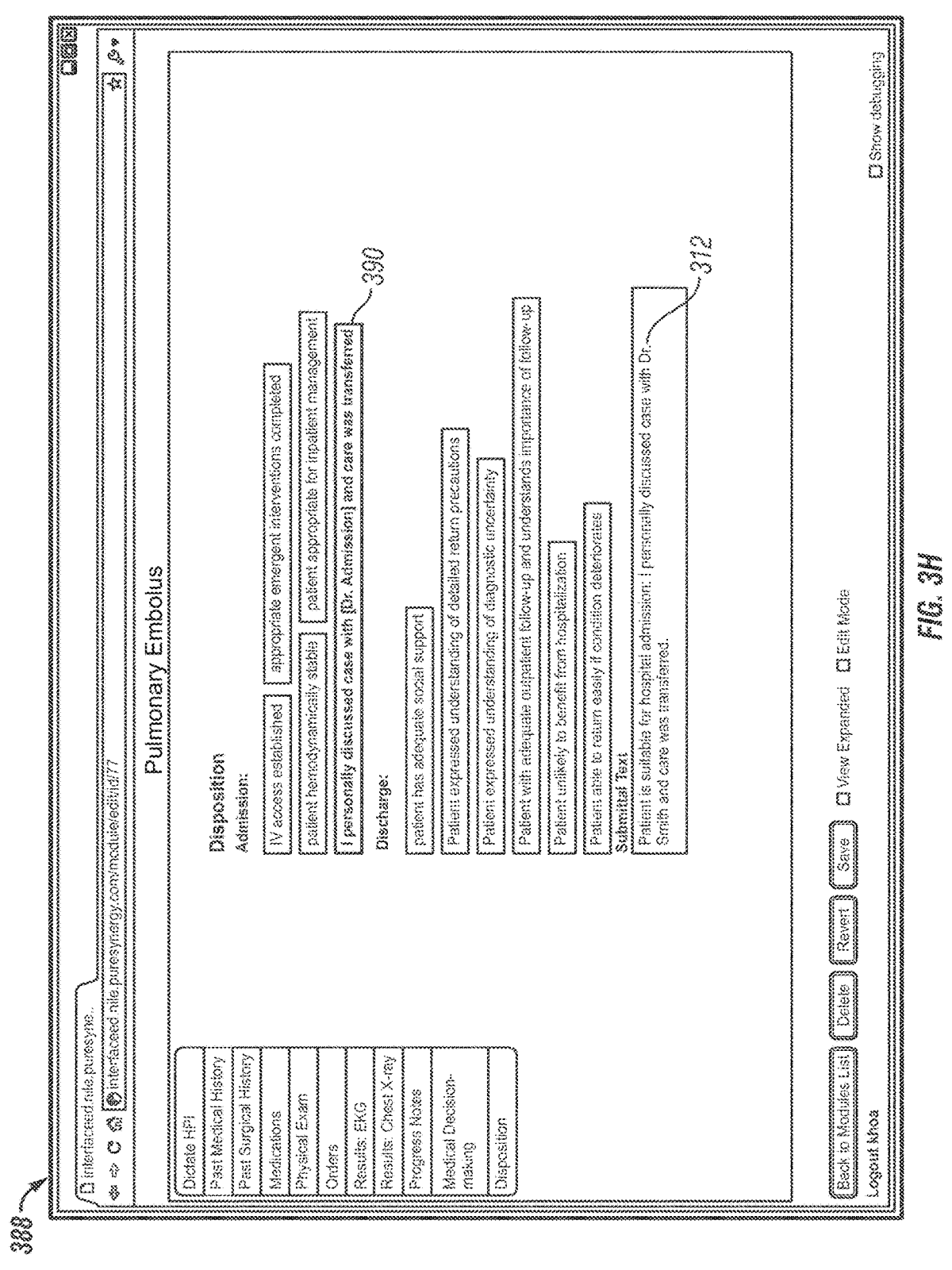
Figure 3I:
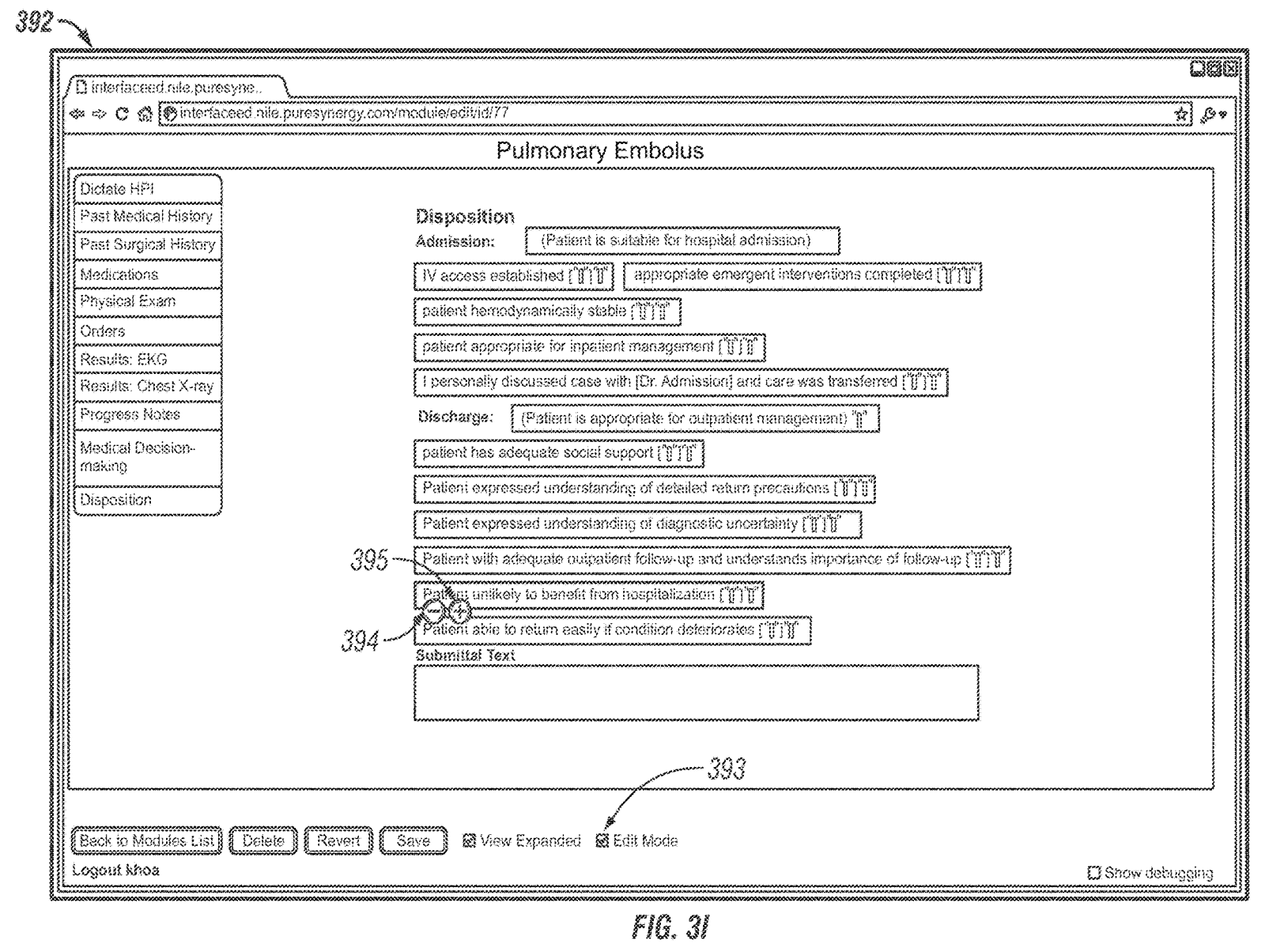
Figure 3J:
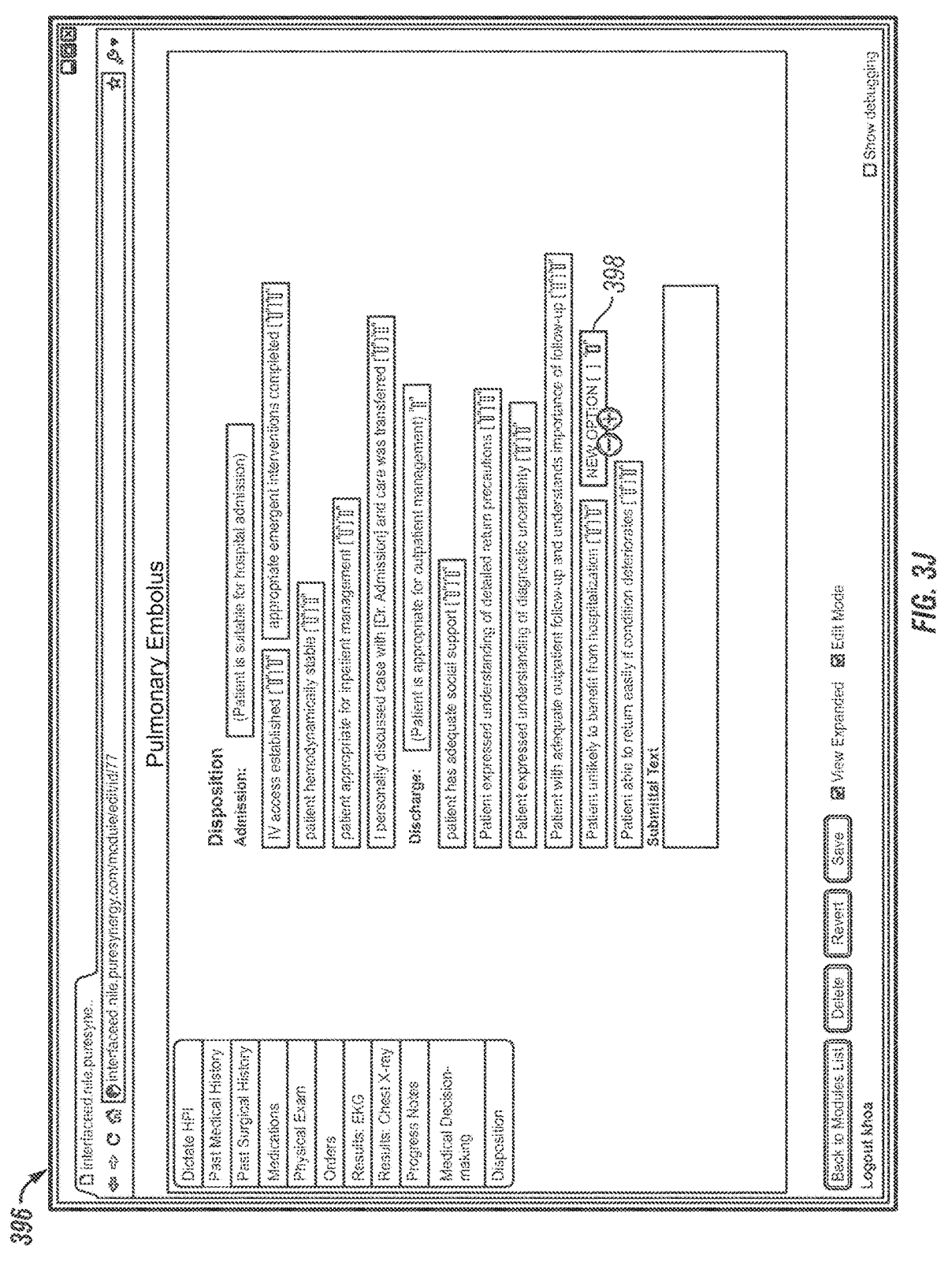
Figure 3M:
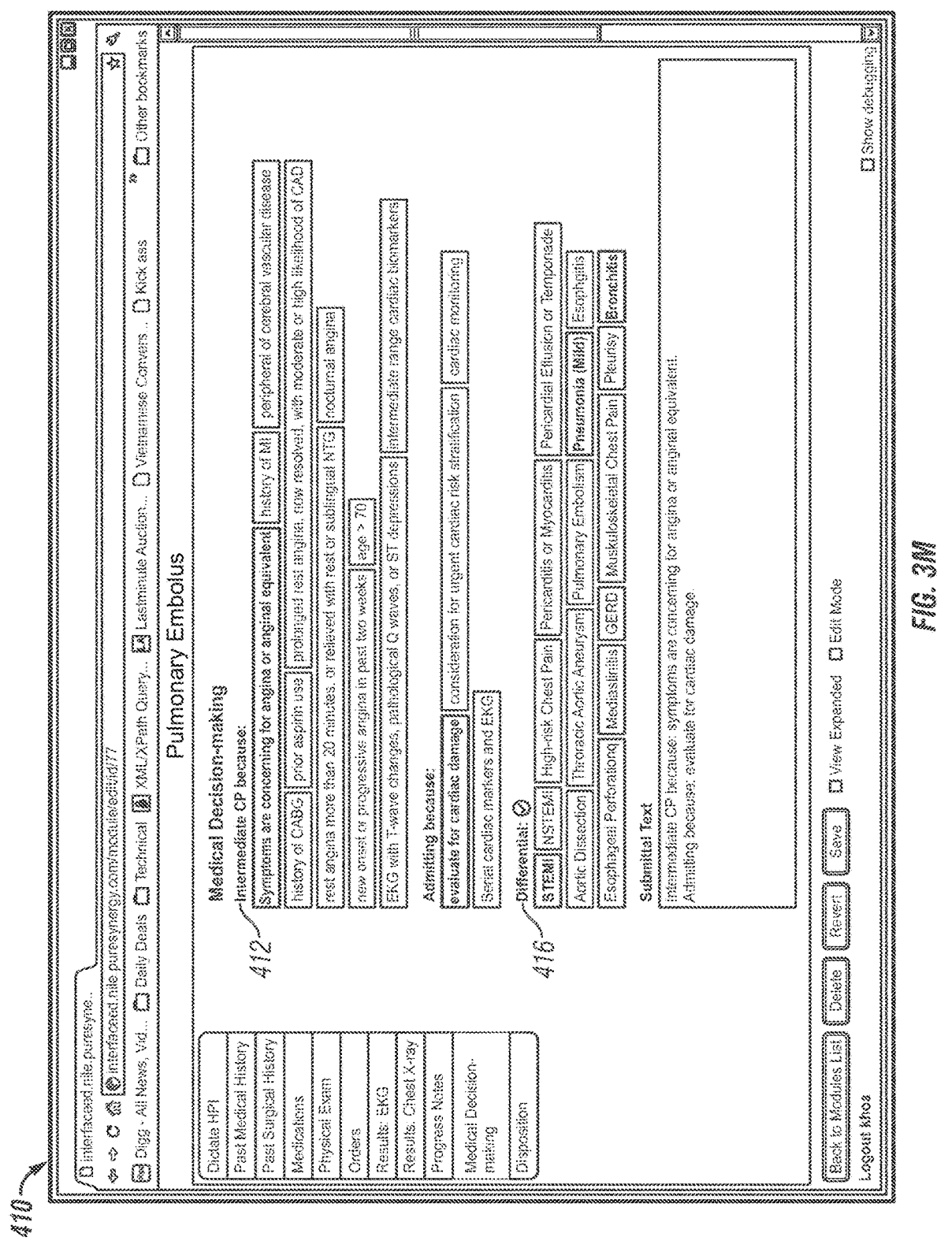
Figure 3W:
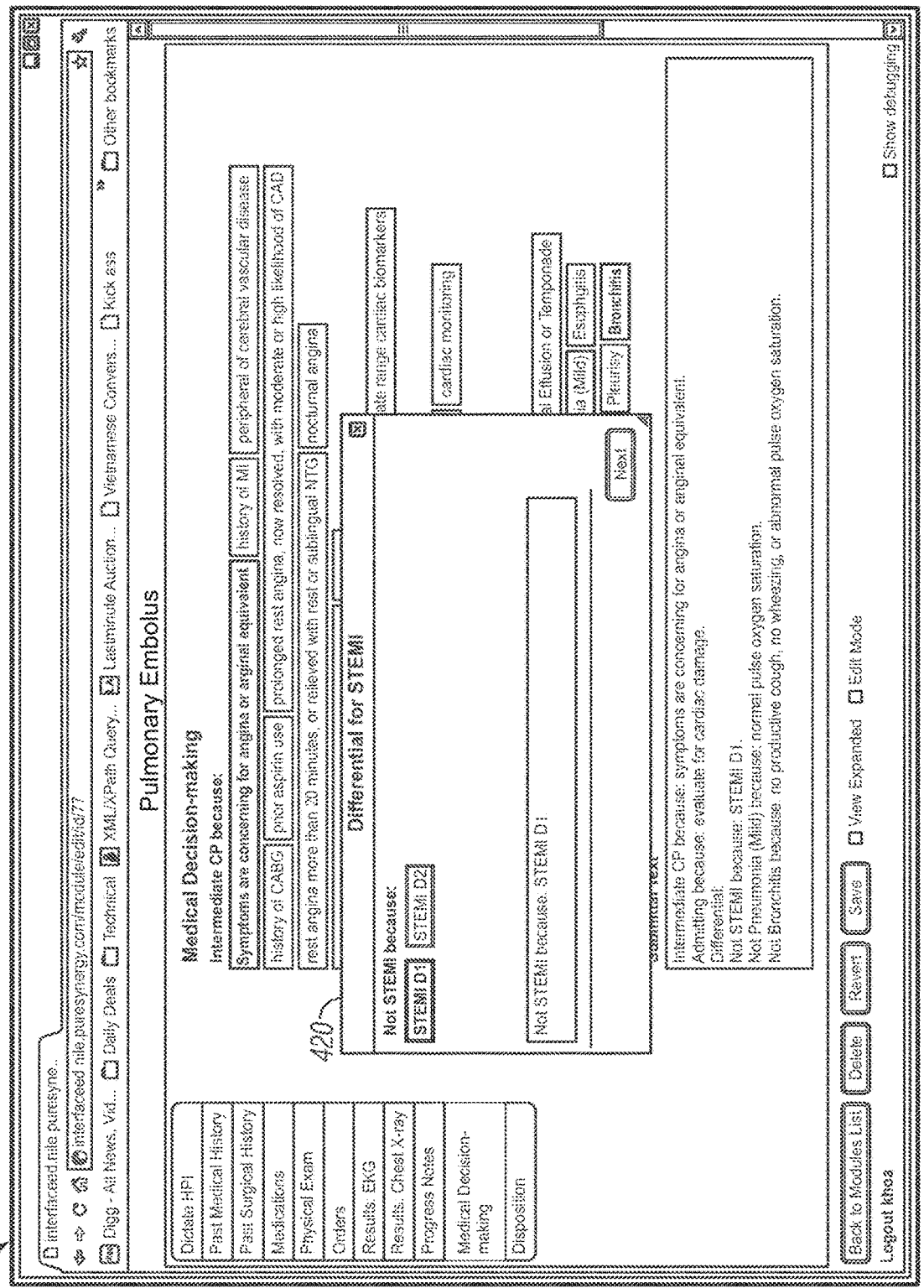
FIGS. 3A, 3B, 3C, 3D, 3E, 3F, 3G, 3H, 3I, 3J, 3K, 3L, 3M, 3N, 3O, 3P, and 3Q are exemplary screenshots that illustrate various steps for providing information on a medical diagnosis using the architecture of FIG. 1A.

FIGS. 3A-3L are exemplary screenshots that illustrate various steps for providing information on a medical diagnosis using the architecture 100 of FIG. 1A. FIG. 3A is an exemplary screenshot 300, from display device 114, of a template associated with a diagnosis of pulmonary embolus 302. The template is likely to be displayed to a user, such as a healthcare provider, during or after the user has completed a meeting with a patient. The diagnosis 302 is identified in the template. The template also displays a plurality of suggested responses 304 and 306 to the query "Dictate HPI" 314. The "Dictate HPI" 314 query is one of a plurality of queries 315 that is included in a template. Each of the plurality of queries 315 for each template can be selectively chosen for display, such as by the provider. In certain implementations, queries 315 are chosen for display if display of the queries will help the provider improve efficiency in entering patient information.

The suggested responses 304 and 306 to the "Dictate HPI" query 314 are divided into two categories 308 and 310 based on the content of the suggested responses 304 and 306. The categories are based on a previously provided response to the at least one query, a user-defined suggested response, facility policy, and a best practice. In the illustrated example, the suggested responses 304 for dictating a History of Present Illness (HPI) include that the illness is "not associated with" 308 the first category of suggested responses 304, and that the HPI is "neither exacerbated or relieved by" 310 the second category of suggested responses 306. The template also includes an input field 312 in which the actual response by the user will be entered.

FIG. 3B is an exemplary screenshot 320 of the template of FIG. 3A after a suggested response has been selected by the user. Specifically, the suggested response "SOB" 322, which stands for shortness of breath, has been selected by the user. After a suggested response 322 is selected by the user, such as by using a keyboard, mouse, pen, or voice command over input device 116, the processor 112 of the client 102 is configured to enter the selected suggested response into the input field 312, as illustrated. The entry, illustrated as "Not associated with SOB," is based on the selected suggested response "SOB" 322, but is more detailed than the selected suggested response 322. For example, instead of just entering the text "SOB" into the input field 312, the text "Not associated with SOB" is entered instead, thereby providing more information on what the selection of the suggested response 322 is intended to mean.

FIG. 3C is an exemplary screenshot 330 of the template of FIG. 3B after a plurality of suggested responses 324, 326, 328, 332, and 334 have been selected by the user. Specifically, the suggested responses "SOB" 322, "palpitations" 326, "nausea" 328, "position" 332, and "exertion" 334 have been selected by the user. As the suggested responses 324, 326, 328, 332, and 334 are selected by the user, the processor 112 of the client 102 is configured to enter the selected suggested responses 324, 326, 328, 332, and 334 together (or "simultaneously") into the input field 312, as illustrated. The entry, illustrated as "Not associated with SOB, palpitations, or nausea. Neither exacerbated or relieved by position or exertion," is based on the selected suggested responses 324, 326, 328, 332, and 334, but is more detailed than the selected suggested responses 324, 326, 328, 332, and 334, and is in a grammatical format that combines the selected plurality of suggested responses. For example, instead of just entering the text "SOB palpitations nausea position exertion" into the input field 312, the text "Not associated with SOB, palpitations, or nausea. Neither exacerbated or relieved by position or exertion," is entered instead, thereby providing more information on what the selection of the suggested responses 324, 326, 328, 332, and 334 is intended to mean.

FIG. 3D is an exemplary screenshot 340 of the template of FIGS. 3A-3C after a plurality of suggested responses 344 and 346 have been selected by the user in response to a query 342 regarding past medical history. Specifically, the suggested responses "no prior CVA" 344 and "no connective tissue disease" 346 have been selected by the user. (CVA stands for "Cerebrovascular accident.") As the suggested responses 344 and 346 are selected by the user, the processor 112 of the client 102 is configured to enter the selected suggested responses 344 and 346 simultaneously into the input field 312, as illustrated. The entry, illustrated as "Previous medical conditions: no prior CVA and no connective tissue disease," is based on the selected suggested responses 344 and 346, but is more detailed than the selected suggested responses 344 and 346, and is in a grammatical format that combines the selected plurality of suggested responses 344 and 346.

FIG. 3E is an exemplary screenshot 350 of the template of FIGS. 3A-3D after a plurality of suggested responses 354, 356, 358, and 360 have been selected by the user in response to a query 352 regarding past surgical history and after the user has provided his own input in response to the query 352. Specifically, the suggested responses "no CABG" 354, "no PCI" 356, "no prior aorta surgeries" 358, and "no prior thoracic surgeries" 360 have been selected by the user. As the suggested responses 354, 356, 358, and 360 are selected by the user, the processor 112 of the client 102 is configured to enter the selected suggested responses 354, 356, 358, and 360 simultaneously into the input field 312, as illustrated. The entry, illustrated as "Past surgeries: no CABG, no PCI, no prior aorta surgeries, and no prior thoracic surgeries," is based on the selected suggested responses 354, 356, 358, and 360, but is more detailed than the selected suggested responses 354, 356, 358, and 360, and is in a grammatical format that combines the selected plurality of suggested responses 354, 356, 358, and 360. The input field 312 also includes text entered manually by the user, for example, using a keyboard, namely the text "Patient reported he had appendix removed" 362.

FIG. 3F is an exemplary screenshot 370 of the template of FIGS. 3A-3E after a patient's physical exam information is entered, in response to a physical exam type query 372, into the input field 312 using suggested responses. Specifically, the suggested responses "brief" 372 for a general exam, "detailed" 374 for a HEENT exam, "detailed" 376 for a neck exam, "brief" 380 for a pulmonary exam, "detailed" 378 for a neurological exam, and "brief" 382 for a heme and lymph exam, have been selected by the user. (HEENT stands for "head, ears, eyes, nose and throat.") As the suggested responses 372, 374, 376, 378, 380, and 382 are selected by the user, the processor 112 of the client 102 is configured to enter the selected suggested responses 372, 374, 376, 378, 380, and 382 simultaneously into the input field 312, as illustrated. The entry reflects more detailed information for each exam than whether the exam was brief or detailed. For example, the brief 372 entry for the general exam states "General: nontoxic, no acute distress, interacting appropriately," while the detailed 374 entry for the HEENT exam states "HEENT: atraumatic, pharynx normal, moist mucous membranes, no tonsillar exudates, no drooling, TMs benign bilaterally, conjuctiva without injection or edudate, no rhinorhea."

FIG. 3G is an exemplary screenshot 384 of the template of FIGS. 3A-3F in which a facility's best practices are identified in the suggested responses. Specifically, a suggested response 386 is provided in the template that is based on the best practices of the user's healthcare facility. As the suggested response 386 is selected by the user, the processor 112 of the client 102 is configured to enter the selected suggested responses 386 into the input field 312, thereby reflecting the facility's best practices.

FIG. 3H is an exemplary screenshot 388 of the template of FIGS. 3A-3G in which a suggested response 390, after entered into the input field 312, is configured to be edited. Specifically, the "[Dr. Admission]" portion of the suggested response 390 is configured to be edited in the input field 312 by selecting that portion (e.g., with a mouse click) and typing text (e.g., the admitting doctor's name) to replace that text.

FIG. 3I is an exemplary screenshot 392 of the templates of FIGS. 3A-3H after an editing mode has been entered. The editing mode is entered by the selecting the "Edit Mode" check box 393. Editing mode allows the template to be modified by a user, such as a healthcare provider or a system administrator. In editing mode, two buttons 394 and 395 are displayed, a subtraction button 394 represented by a subtraction sign, and an addition button 395 represented by an addition sign. Selection of the subtraction button 394 (e.g., by clicking the button with a mouse) removes an associated suggested response, and selection of the addition button 395 adds a new suggested response 398, as illustrated in the screenshot 396 of FIG. 3J. This feature may be used, for example, when a user finds that a suggested response he/she uses in responding to a query for a medical diagnosis is not present in the template. The new suggested response 398 can be edited as illustrated in the screenshot 400 of FIG. 3K, wherein the new suggested response 402 has been edited to read "Patient checked out AMA." Thereafter, when edit mode is exited, as illustrated in the screenshot 404 of FIG. 3L, the newly added suggested response 406, upon selection, causes certain text, namely "Patient is appropriate for outpatient management: Patient checked out AMA," to be entered into the input field 312.

FIG. 3M is an exemplary screenshot 410 of a Medical Decision Making (MDM) query. In certain implementations, each template includes a MDM query. The MDM query is configured to provide criteria for satisficing the provider's selected diagnosis. The satisficing criteria facilitate the consideration and exclusion of competing diagnoses (e.g., diagnoses that would replace the selected diagnosis). In certain implementations, the MDM query of each template is not required to be displayed to the provider. In certain implementations where the MDM query is displayed, the MDM query required to be completed by the provider. Activation of the MDM query facilitates the provider in both documenting the decision making process for the selected diagnosis, and improving the accuracy of the selected diagnosis, thereby improving patient care. The MDM interface prompts a provider to provide positive reasons 412 to support his/her diagnosis/diagnoses. In certain implementations, the provider also selects from a list of competing diagnoses in a "Differential" section 416 that may be eliminated from consideration for the patient complaint.

Figure 3P:
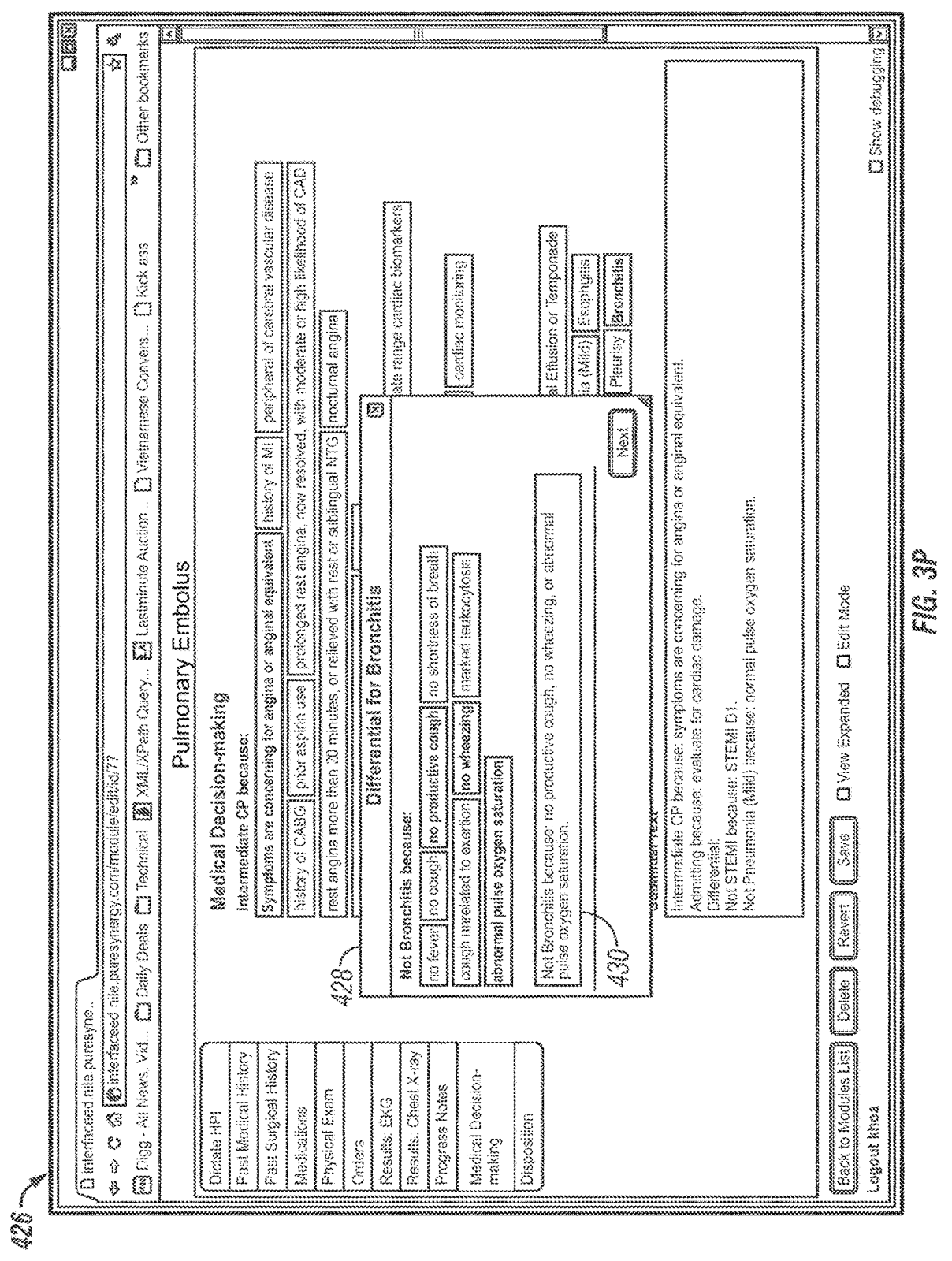

FIGS. 3N, 3O, and 3P are exemplary screenshots 418, 422, and 426 of prompts 420, 424, and 428 displayed in response to the eliminated diagnoses selected in the Differential section 416 of FIG. 3M. In certain implementations, for each eliminated diagnosis that is selected, a prompt 420, 424, and 428 is displayed for the provider to enter reasons why the provider selected the diagnosis to be eliminated. In FIG. 3N, the prompt 420 is for the eliminated diagnosis "STEMI." In FIG. 3O, the prompt 424 is for the eliminated diagnosis "Pneumonia (mild)." In FIG. 3P, the prompt 426 is for the eliminated diagnosis "bronchitis." As discussed above, after a suggested response 428 is selected by the user (e.g., provider), such as by using a keyboard, mouse, pen, or voice command, the processor 112 of the client 102 is configured to enter text indicative of the selected suggested response into an associated input field 430, as illustrated.

FIG. 3Q is an exemplary screenshot 432 of the MDM interface of FIG. 3M after text indicative of the provider's selections have been entered into an associated input field 434. Specifically, the text in the associated input field 434 includes a description of the eliminated diagnoses that were selected by provider after prompting by the disclosed system.

Figure 4:
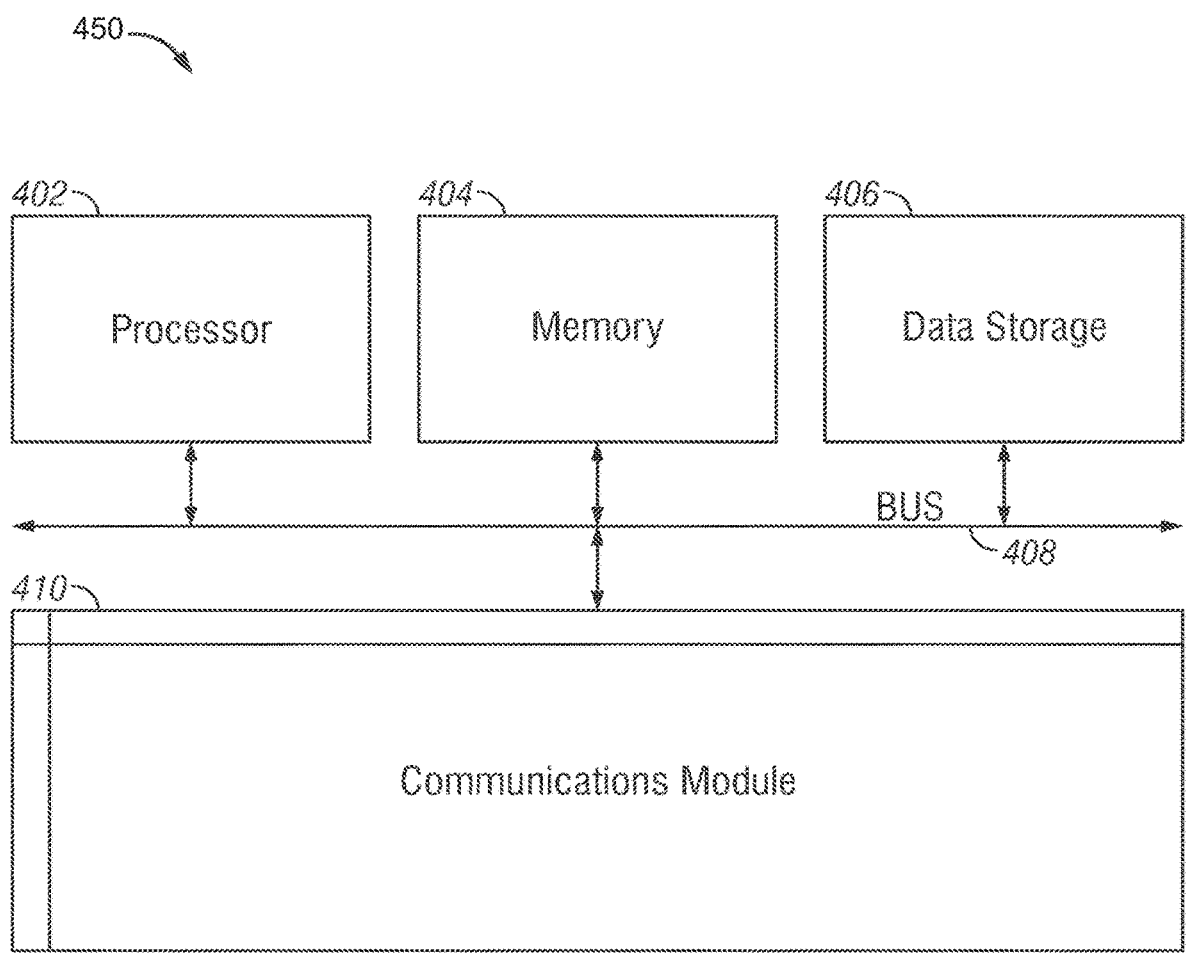
FIG. 4 is a block diagram illustrating an example of a computer system with which the client, the local server, or the remote server illustrated in FIG. 1A can be implemented.

FIG. 4 is a block diagram illustrating an example of a computer system 450 with which the client 102, the local server 150, or the remote server 130 illustrated in FIG. 1A can be implemented. In certain implementations, the computer system 450 may be implemented using software, hardware, or a combination of both, either in a dedicated server, or integrated into another entity, or distributed across multiple entities.

Computer system 450 (e.g., client 102, the local server 150, or the remote server 130 from FIG. 1A) includes a bus 458 or other communication mechanism for communicating information, and a processor 452 (e.g., processor 112, 154, or 136 from FIG. 1A) coupled with bus 458 for processing information. By way of example, the computer system 450 may be implemented with one or more processors 452. Processor 452 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. Computer system 450 also includes a memory 454 (e.g., memory 104, 152, or 132 from FIG. 1A), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 458 for storing information and instructions to be executed by processor 452. The instructions may be implemented according to any method well known to those of skill in the art, including, but not limited to, computer languages such as data-oriented languages (e.g., SQL, dBase), system languages (e.g., C, Objective-C, C++, Assembly), architectural languages (e.g., Java), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 404 may also be used for storing temporary variable or other intermediate information during execution of instructions to be executed by processor 402. Computer system 450 further includes a data storage device 456 such as a magnetic disk or optical disk, coupled to bus 458 for storing information and instructions. Computer system 450 may be coupled via communications module 460 (e.g., communications module 110, 156, or 138 from FIG. 1A) to various devices (not illustrated). The communications module 410 can be any input/output module. In certain implementations not illustrated, the communications module 410 is configured to connect to a plurality of devices, such as an input device (e.g., input device 116 from FIG. 1A) and/or a display device (e.g., display device 114 from FIG. 1A).

According to one aspect of the present disclosure, the client 102, the local server 150, or the remote server 130 can be implemented using a computer system 450 in response to processor 452 executing one or more sequences of one or more instructions contained in memory 454. Such instructions may be read into memory 454 from another machine-readable medium, such as data storage device 456. Execution of the sequences of instructions contained in main memory 454 causes processor 452 to perform the process steps described herein. One or more processors in a multi-processing arrangement may also be employed to execute the sequences of instructions contained in memory 454. In alternative implementations, hard-wired circuitry may be used in place of or in combination with software instructions to implement various implementations of the present disclosure. Thus, implementations of the present disclosure are not limited to any specific combination of hardware circuitry and software.

The term "machine-readable medium" as used herein refers to any medium or media that participates in providing instructions to processor 452 for execution. Such a medium may take many forms, including, but not limited to, non-volatile media, volatile media, and transmission media. Non-volatile media include, for example, optical or magnetic disks, such as data storage device 456. Volatile media include dynamic memory, such as memory 454. Transmission media include coaxial cables, copper wire, and fiber optics, including the wires that comprise bus 458. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read.

The disclosed systems and methods provides a user interface for providing information on a medical diagnosis that addresses key issues in prior art EMRs that reduce productivity, change work flow, produce less useful clinical documentation, and create the tools to improve the end users' experience through a more robust interface. The disclosed systems and methods use a diagnosis driven protocol to provide a user interface that is matched to a healthcare provider's cognitive process, which results in a substantial increase in workflow efficiency. In certain implementations, the disclosed systems and methods result in an improved interaction between healthcare providers and EMRs, thereby creating workplace advantages and efficiencies by improving work flow efficiencies in medical departments and professional office settings, increasing professional reimbursement, decreasing time devoted directly to electronic documentation in the order of hours a day, improving quality of work life and job satisfaction, resulting in reduced staff turnover and greater group stability, increasing patient satisfaction, and increasing quality of care delivery and decreasing medical liability.

Figure 5:
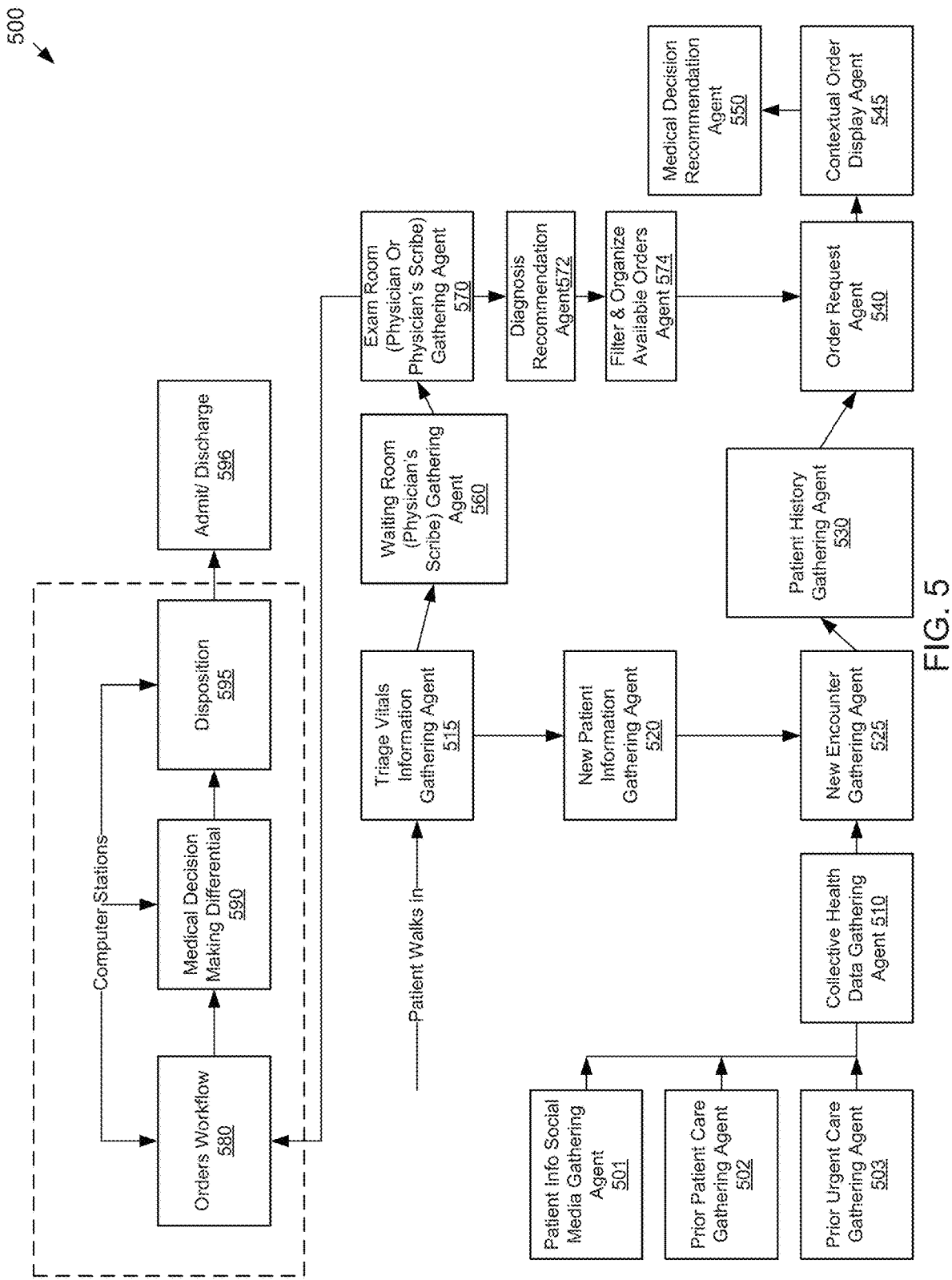
FIG. 5 depicts a diagram illustrating an example of a hospital facility environment.

FIG. 5 depicts a diagram illustrating an example of a hospital facility environment 500 using an automated diagnoses patient archetypes system. In the example of FIG. 5, the hospital facility environment 500 includes a patient information social media gathering agent 501, a prior patient care gathering agent 502, a prior urgent care gathering agent 503, a collective health gathering agent 510, a triage vitals gathering agent 515, a new patient information gathering agent 520, a new encounter gathering agent 525, a patient history gathering agent 530, an order request agent 540, a contextual order display agent 545, a medical decision recommendation agent 550, a waiting room gathering agent 560, an exam room gathering agent 570, a diagnosis recommendation agent 572, a filter & organize available orders agent 574, an orders workflow engine 580, a medical decision making differential engine 590, a disposition engine 585, and an admit/discharge engine 596. One or more of the "gathering agents" and the "engines" in the figure may be implemented using "engines" and "datastores" described herein.

A complete library of medical illnesses are used dynamically to create a super plurality of automated diagnosis patient archetypes. Each automated diagnosis patient archetype represents a hypothetical patient with a set of specific symptoms that point to a specific medical diagnosis. The specific symptoms including different attributes are stored in the automated diagnoses archetypes systems in the form of patient parameters. The automated diagnoses archetypes system creates a patient profile based on an actual patient. The patient profile can then be associated with plurality of automated diagnosis patient archetypes based on applicable matching between different patient parameters. The automated diagnoses archetypes system navigates the patient profile by narrowing the super plurality of automated diagnosis patient archetypes based on comparing applicable patient parameters to generate an applicability score.

In some implementations, patient records can be pulled using an application programing interface to collective health gathering agent 510 from different sources, including but not limited to information on patient information social media gathering agent 501, prior patient care gathering agent 502 and prior urgent care gathering agent 503. New encounter gathering agent 525 depicts a stage to get information regarding the current illness when a patient walks in to a hospital facility. The first stage for the care is to get patient's vital signs for triage decision at triage vitals gathering agent 515. The system puts in new patient information at 520 followed by current illness information at new encounter gathering agent 525. The patient is requested to submit patient information on history of present illness, review of the system, past medical history, family history and social history at 530. The requested patient information can also be automatically pulled using the application programming interface at 510. The next stage of processing is based on requested orders at 540. Selected order results are displayed contextual based on relevance to a given medical diagnosis.

The physician's scribe in a waiting room related to the waiting room gathering agent 560 may request additional patient information that is relevant to a particular illness. The physician examines the patient in the exam room related to the exam room gathering agent 570. Based on a created patient profile and actual physical examination, the physician selects a dynamic medical diagnosis by the diagnosis recommendation agent 572 for the patient profile. An emphasized order list is generated based on the selected dynamic medical diagnosis by the diagnosis recommendation agent 572 and a subset of automated diagnosis patient archetypes associated with the patient profile. The physician can then request orders based on an already filtered and organized list and recommendations from the automated diagnoses system.

One or more computer stations for the nurses, scribes and physicians include orders workflow engine 580, medical decision making differential engine 590 and disposition 595. The physician can confirm the final medical decision using the medical decision recommendation agent 550 and get support for admit or discharge decision by the admit/discharge engine 596. The triage vitals gathering agent 515, Waiting room gathering agent 560 and exam room gathering agent 570 could access the automated diagnoses system using mobile devices including mobile phones, smartphones, tablets or laptops. The actual movement of the patient through different stages in a hospital facility is depicted logically in the automated diagnoses system. The automated diagnoses system includes super plurality of automated diagnosis patient archetypes based on different medical illnesses. For example, the super plurality of automated diagnosis patient archetypes includes automated diagnosis patient archetypes for both males and females including, for example, "pregnancy archetype" and/or "prostate cancer archetype." Based on current patient parameter and profile, the a subset from the plurality of automated diagnosis patient archetypes can be quickly associated based at least upon whether the patient is male or female. Thus, the initial physician diagnosis can safely be applied to only a subset of the plurality because the super plurality will clearly not be applicable. The automated diagnoses system could even have an alert that says, "you just diagnosed a man with pregnancy" by verifying that all patient parameters in the profile help establish an applicability score that ranks the automated diagnosis patient archetypes.

The social media information at 501, for example, could include past and present global positioning system ("GPS") information. For example, if the past GPS history shows that the patient has traveled to a country where malaria is prevalent, the automated diagnoses archetypes system associates the automated diagnosis patient archetype that has those parameters and also automatically places emphasis on orders that would validate the same diagnosis. The prior patient care gathering agent 502 or the prior urgent care gathering agent 503 could be pulled by an automated agent from the same facility or one or more remote locations.

Another example of relevant social media information would include the time period in which the patient heavily uses social media and the average number of hours in a day that are used in sending or responding to social media communication. For example, a patient who is a heavy user of social media may be suffering from carpal tunnel syndrome. Many hours on some of the social media websites promote psychological disorders including depression symptoms. The automated diagnoses archetypes system attempts to build a complete picture of information surrounding a given patient that in turn helps a physician make the appropriate and correct diagnosis.

Figure 6:
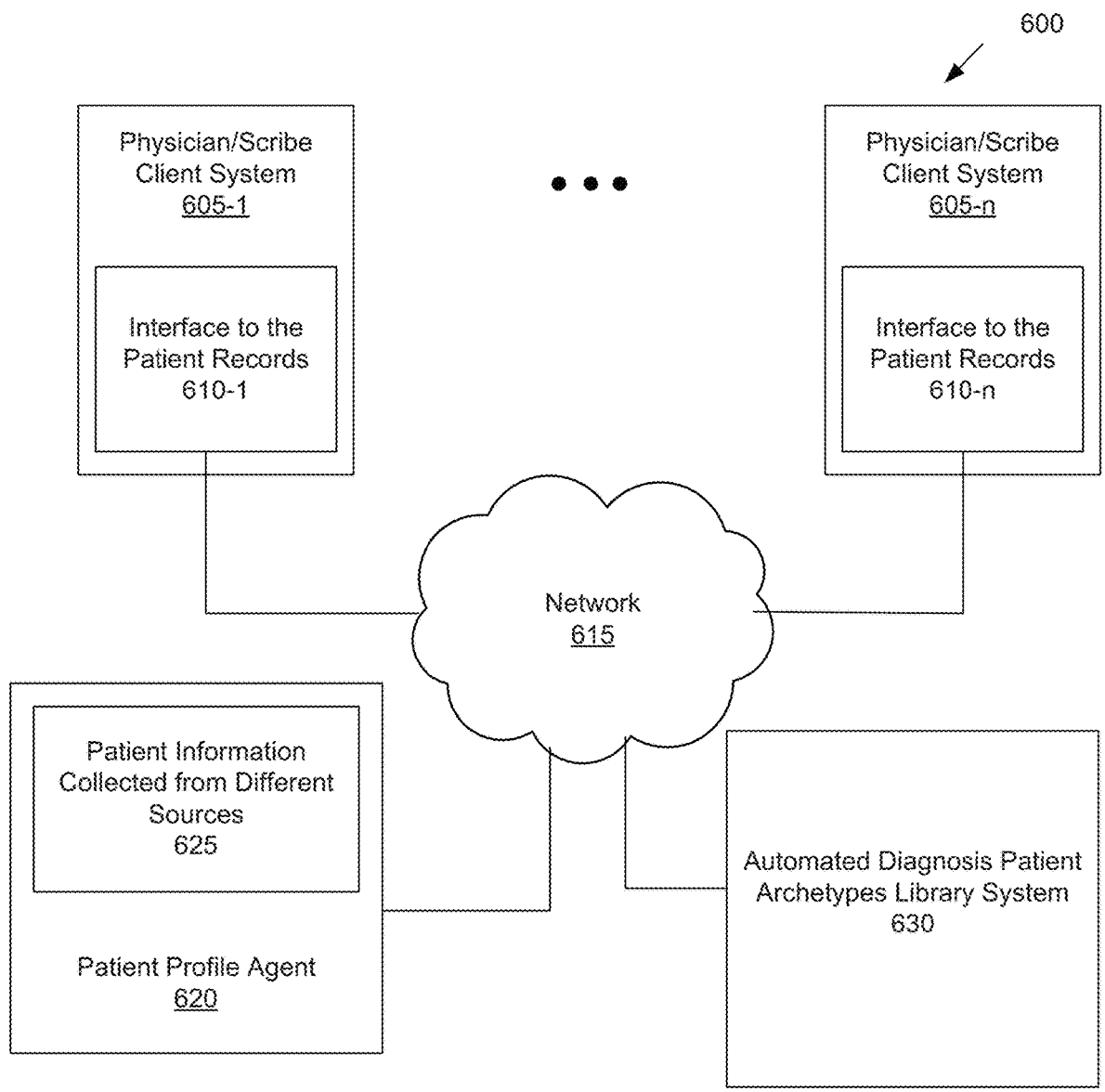
FIG. 6 is a diagram illustrating an example of an automated diagnosis patient archetypes system 600.

FIG. 6 is a diagram illustrating an example of an automated diagnosis patient archetypes system 600, according to some implementations. In the example of FIG. 6, the automated diagnosis patient archetypes system 600 includes physician/scribe client system(s) 605, a network 615, a patient profile agent 620, and an automated diagnosis patient archetypes library system 630. In the example of FIG. 6, the physician/scribe client system(s) 605, the patient profile agent 620, and the automated diagnosis patient archetypes library system 630 may be coupled to one another over the network 615. The components in FIG. 6 may be coupled to one another in other ways not explicitly shown.

In a specific implementation, physician/scribe client system(s) 605-1 to 605-n each include a customized user interface 610-1 to 610-n to interact with the automated diagnoses archetypes system.

Different implementations described herein include components or structures to perform the described functionality. An automated agent as used in here refers to a software or hardware component that may include a dedicated or shared processor and, typically, firmware or software modules executed by the processor. Depending upon implementation-specific or other considerations, an automated agent can be centralized or its functionality distributed. An automated agent may include special purpose hardware, firmware, or software embodied in a computer-readable medium for execution by the processor.

A "datastore," as used in this disclosure, can be implemented as software embodied in a physical computer-readable medium on a general- or specific-purpose machine, in firmware, in hardware, in a combination thereof, or in an applicable known or convenient device or system. Datastores in this disclosure are intended to include any organization of data, including tables, comma-separated values (CSV) files, traditional databases (e.g., SQL), or other applicable known or convenient organizational formats. Datastore-associated components, such as database interfaces, can be considered "part of" a datastore, part of some other system component, or a combination thereof, though the physical location and other characteristics of datastore-associated components is not critical for an understanding of the techniques described in this disclosure. Datastores can include data structures. As used in this disclosure, a data structure is associated with a particular way of storing and organizing data in a computer so it can be used efficiently within a given context. Data structures are generally based on the ability of a computer to fetch and store data at any place in its memory, specified by an address, a bit string that can be itself stored in memory and manipulated by the program. Thus some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures for creating and manipulating instances of that structure.

As used here, a computer-readable medium is intended to include all mediums that are statutory (e.g., in the United States, under 35 U.S.C. 101), and to specifically exclude all mediums that are non-statutory in nature to the extent that the exclusion is necessary for a claim that includes the computer-readable medium to be valid. Known statutory computer-readable mediums include hardware (e.g., registers, random access memory (RAM), non-volatile (NV) storage, to name a few), but may or may not be limited to hardware.

Network 615 can be different wireless and wired networks available to connect different computer devices including client and server systems. In an implementation, network 615 is publically accessible on the internet. In an implementation, network 615 is inside a secure corporate wide area network. In an implementation, network 615 allows connectivity of different systems and devices using a computer-readable medium. In an implementation, the route optimization and schedule coordination system allows user on the client system or the activity provider to set privacy settings that allow data to be shared among select family and friends, but the same data is not accessible publically by others. In an implementation, network 615 includes connectivity through a computer-readable medium.

The network can include internal networks of an organization including local area network ("LAN") or wide local area network ("WLAN"). In one implementation, the network 615 includes networks of more than one organization. In one implementation, the network 615 includes the internet. Those skilled in the art would understand that the client and server systems include a computing processor that may include a central processing unit ("CPU") within physician/scribe client system(s) 605, patient profile agent 620 that works with patient information collected from different sources using different gathering agents 625 and library of automated diagnosis patient archetypes library system 630 that carry out the instructions of a computer program by performing the basic arithmetical, logical, and input/output operations. The network communications may include wireless communications as well as wired communications. The network 615 may be a group of two or more computer systems (e.g., a smartphone, mobile, tablet) interconnected by communication paths. The application of the client system includes a plugin to interface to the automated diagnosis, patient profile and super plurality library of automated diagnosis patient archetypes systems that may be a program and/or a group of programs designed for a user of the client system to communicate. The operating system of the systems may be the low-level software that supports the basic functions (e.g., scheduling tasks, controlling peripherals) of the client and/or server systems, according to one implementation.

The physician/scribe client system(s) 605 may have different customized user interface and access control depending on whether the physician/scribe client system(s) 605 is designed for use by a scribe, nurse, physician or another employee of the organization. An organization, for example a hospital facility, may configure different display views and give customized rights to the client-system interface with the automated diagnoses archetypes system based on an organization's priorities, projects and current milestones. The interface would be compatible with and implement authentication and encryption systems to work seamlessly with the health care records systems and built-in safe guards.

The automated diagnoses archetypes system includes mechanics to control confidential content by encrypting each patient profile and associated automated diagnosis patient archetypes with confidential information with a secure code that can be decrypted with valid client recipients who also have authorized codes. For each client-system, policies can be set at the time of installing the automated diagnoses archetypes system interface. The automated diagnoses archetypes system and corresponding environment automatically adheres to the policy. Policy parameters can include whether a given user profile is allowed to view order lists, select orders for a given patient, view or input patient confidential information and see the ranking of automated diagnosis patient archetypes.

Different implementations described herein include automated agents, components or structures to perform the described functionality. An automated agent as used in here refers to a software or hardware component that may include a dedicated or shared processor and, typically, firmware or software modules executed by the processor. Depending upon implementation-specific or other considerations, an automated agent can be centralized or its functionality distributed. An automated agent may include special purpose hardware, firmware, or software embodied in a computer-readable medium for execution by the processor.

In various implementations, the modules of the automated diagnosis patient archetypes system 600 may implement automated agents that identify one or more automated diagnosis patient archetypes for a patient's medical condition. An "automated diagnosis patient archetype," as used herein, may refer to a library of medical conditions that is used to segment patients according to market segmentation variables. Though automated diagnosis patient archetypes may segment patients in a variety of ways, in some implementations, the automated diagnosis patient archetype may segment individuals based on one or more of geographic data, demographic data, psychographic data, and behavioristic data. In some implementations, the automated agents described herein may narrow a super plurality of automated diagnosis patient archetypes to match a patient profile based on information collected from different sources. Relevant sources of information may include, but need not be limited to: information collected from an interview with the patient, information related to prior patient care, prior urgent care, social media, and family social history, etc. Based on these and potentially other sources of information, the patient profile may be mapped to relevant automated diagnosis patient archetypes.

In some implementations, one or more automated agents may be employed to customize a user interface on a digital device of the health care professional. The user interface may allow the health care professional to select order selections, to support eliminating a false positive in the proper subset of the plurality of patient persons, to support eliminating a false negative in the plurality of automated diagnosis patient archetypes, and/or to increase a predicted applicability of a set of automated diagnosis patient archetypes to the patient profile. The user interface may receive from the health care professional a "confirmed dynamic physician diagnosis," or a diagnosis made by the health care professional based on the extent the medical condition matches or does not match with proposed diagnoses associated with a specific automated diagnosis patient archetype. In various implementations, a subset of automated diagnosis patient archetypes ranking may be updated based on order results received from the health care professional (e.g., orders made by the health care professional as part of a treatment plan for a diagnosis for a specific medical condition diagnosed using an automated diagnosis patient archetype). In some implementations, the automated agents described herein may make confirmed dynamic physician diagnosis may be made available to other health care professionals, including health care professionals that may treat the patient at a later date and/or health care professionals that may treat other patients for similar medical conditions.

Figure 7:
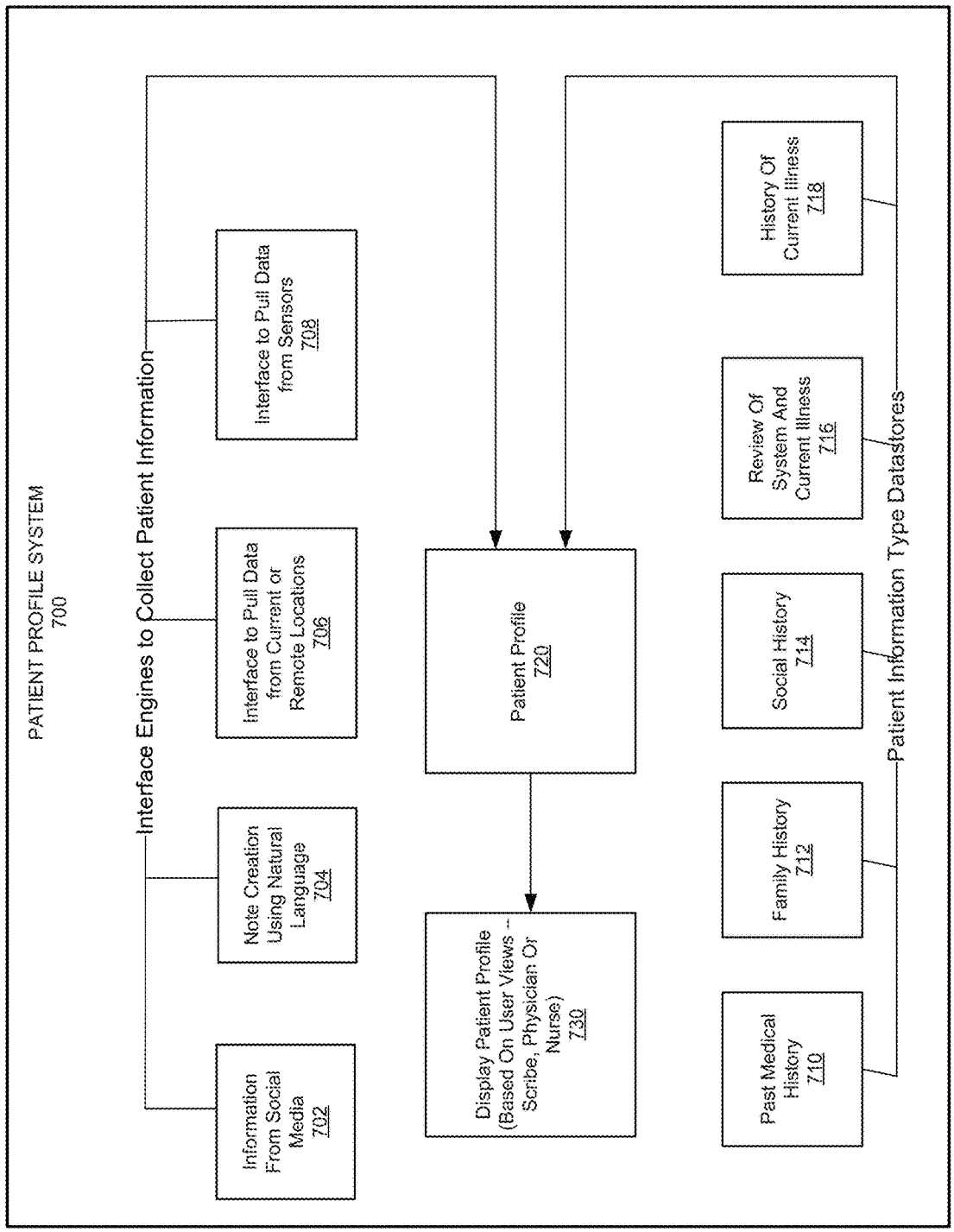
FIG. 7 depicts a diagram illustrating an example of a patient profile system.

FIG. 7 depicts a diagram illustrating an example of a patient profile system 700, according to some implementations. The patient profile system 700 may include a social media information engine 702, an NLP note creation engine 704, a remote location interface engine 706, a sensor data interface engine 708, a past medical history datastore 710, a family history datastore 712, a social history datastore 714, a system/current illness datastore 716, a current illness history datastore 718, a patient profile engine 720, and a patient profile display engine 730 One or more of the components in the figure may be coupled to one another or to modules not explicitly shown.

The patient profile system 700 may be associated with collecting data of a patient. The patient may be currently requesting medical diagnosis at a location that implements that automated diagnoses archetypes system. The patient profile system 700 may use automated agents to automatically pull or receive automatically pushed information associated with the patient from different sources. One or more automated agents may use application programming interfaces to interact with different sources. Patient information from social media information engine 702 may be received from an interface into the automated diagnoses archetypes system. Another automated agent uses an interface that receives information from a patient interview using automated note creation using NLP note creation engine 704. An remote location interface engine 706 uses an interface to receive information from hospital records at the current location of the patient. In a specific implementation, the remote location interface engine 706 uses an interface to receive information from one or more remote locations that the patient has visited in the past prior to his or her current visit.

The sensor data interface engine 708 may use an interface to receive data from health sensors connected to the patient. For example, a patient may be using a health band or watch that automatically monitors his or her heart rate, sleep and walking habits. The sensor data interface engine 708 can pull such current or past information if available for a health sensor that the patient uses routinely. In another implementation, the sensor data interface engine 708 may receive information from a health sensor that is given to the patient at the hospital to automatically get information on his vital signs and upload the data to the automated diagnoses archetypes system. In one implementation, the health sensor may be an internet device with network connectivity capable of uploading patient information.

Implementations of the present disclosure are not limited to the specific automated agents interfaces or combination of the interfaces described herein. A person of ordinary skill in the art would understand the disclosure to include automated agents with interfaces to receive information from different types of sources including processing information from computer or non-computer based systems. Such interfaces could include gathering of patient associated information with the use of optical scanner technology, image, audio or video processing or computer based databases.

The types of patient information that can be received by the automated diagnoses archetypes system includes, for example, past medical history datastore 710, family history datastore 712, social history datastore 714, review by the system/current illness datastore 716 and history of current illnesses in the current illness history datastore 718. The automated diagnoses archetypes system creates a complete and a comprehensive patient profile in the patient profile engine 720 using one or more automated agents with interfaces to receive information from different sources. A customized user interface on a display configured by the patient profile display engine 730 is used to display the patient profile. In one implementation, the customized user interface is modified based on whether the user is a scribe, a physician, a nurse or some other employee of the facility. The display generated can emphasize patient parameters that are of relevance to the current illness of the patient.

In one implementation, the automated diagnoses archetypes system generates displays with information in a human-readable form that emphasizes information related to patient parameters that is of relevance to the current illness of the patient. In one implementation, the emphasis is based on one or more of the following: highlighting the text, changing the color, italicizing the text, or reordering the list. In one implementation, the user of the system can customize the display emphasis style based on his or her personal preference.

Figure 8:
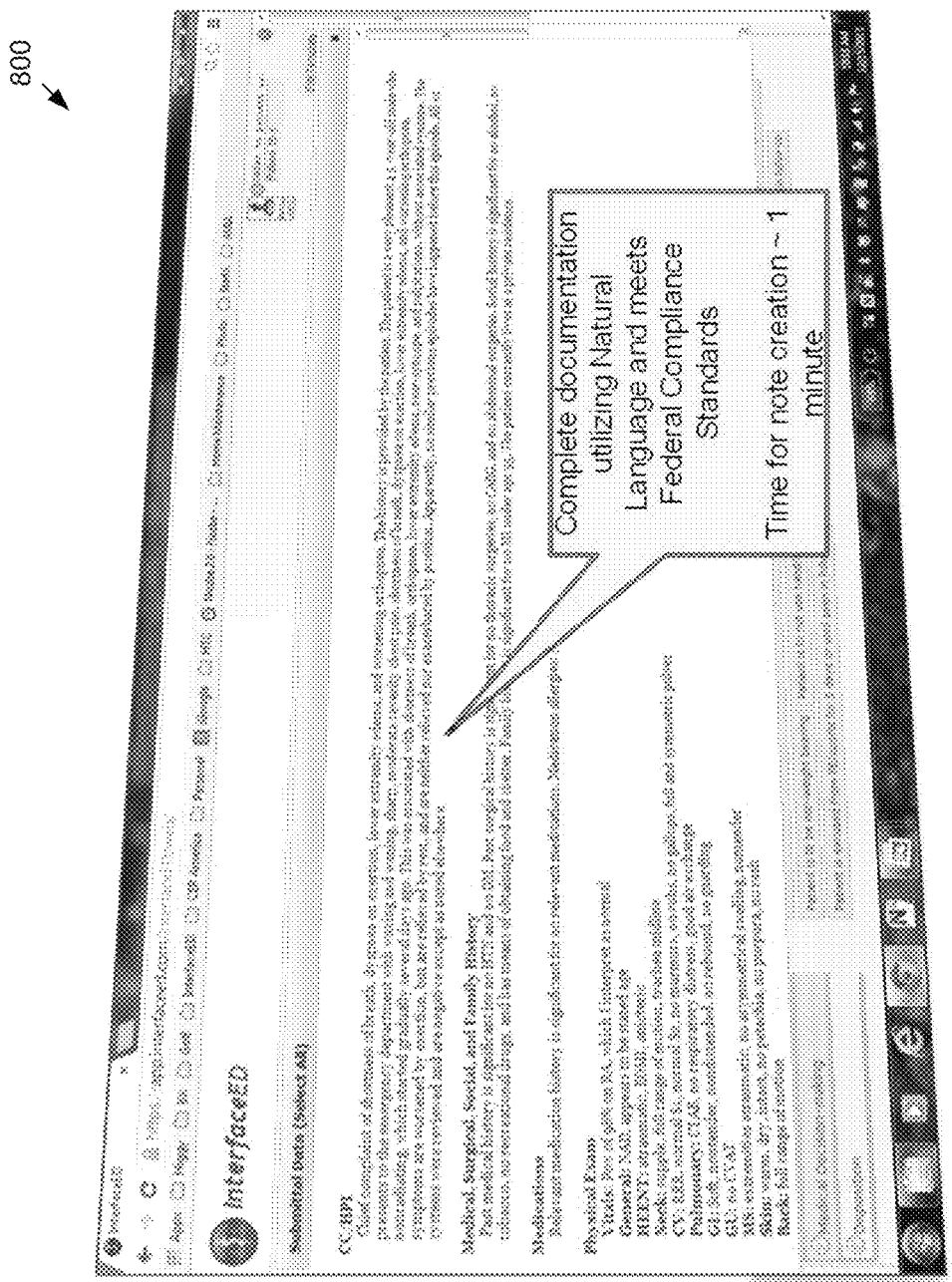
FIG. 8 is an example of a screenshot used to receive patient records using natural language note creation.

FIG. 8 is an example of a screenshot 800 showing use of an automated gathering agent with an interface used to receive patient records using natural language note creation. For example, if the patient complains of shortness of breath, the automated gathering agent will pull up related notes on symptoms that go with shortness of breath including for example text related to different pains associated with shortness of breath including, for example, "waxing and waning, sharp, moderate severity pain."

Figure 9:
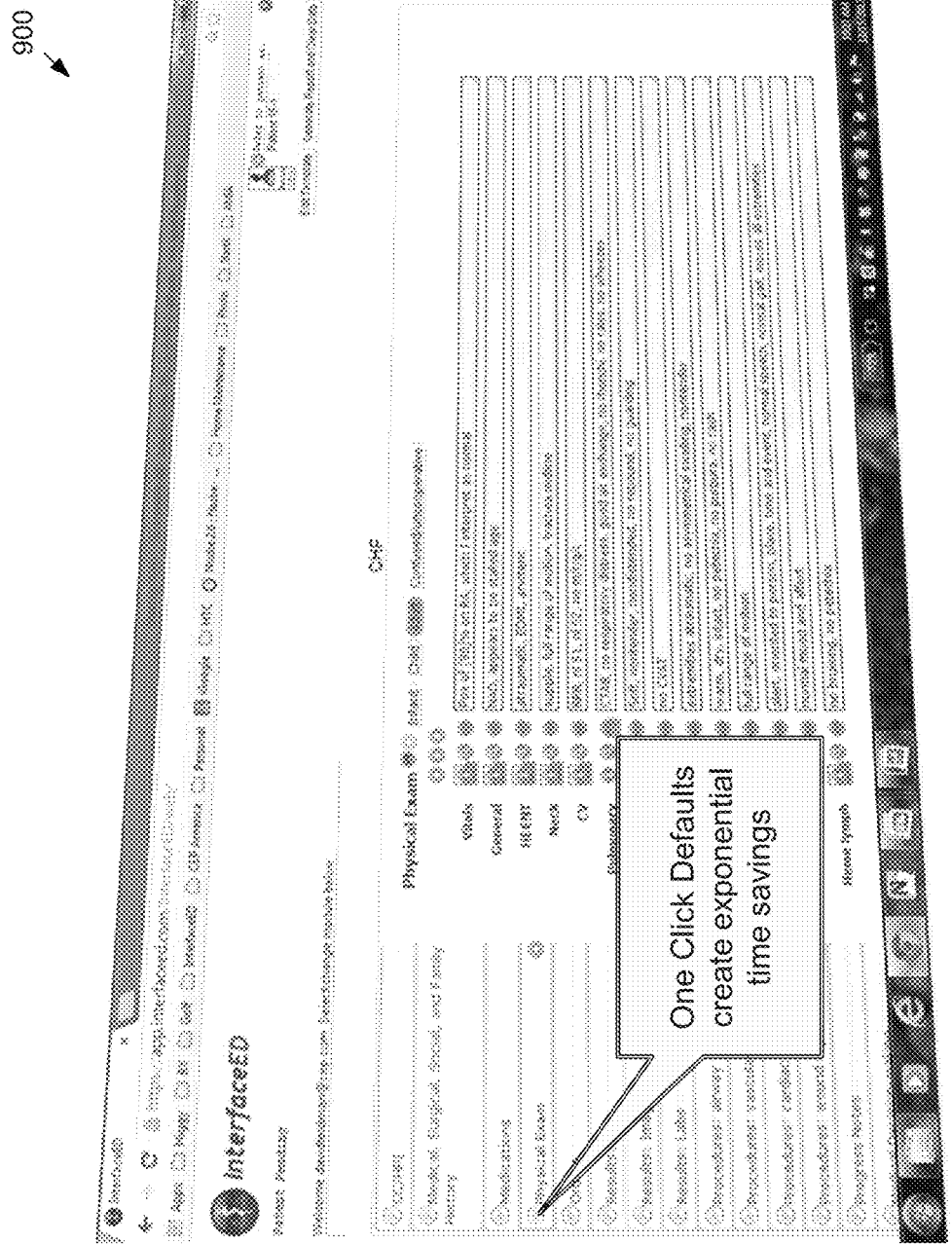
FIG. 9 is an example of a screenshot used to receive patient records.

FIG. 9 is an example of a screenshot 900 used to receive patient records. One click selection of the user interface with radio buttons on the left side of the screen show an example of inputting patient information. Patients and care givers who are conducting patient interviews want to input patient information into the system as fast and efficiently as possible. The screenshot in FIG. 9 shows that the automated diagnoses archetypes system is designed with a smooth flow that allows quick and fast inputs including using single click instead of double clicks and avoiding confirming inputs at each stage that unnecessarily slow down the system. For example, a single screen at the very end can ask the user to confirm all the data that is input with a double click.

Figure 10:
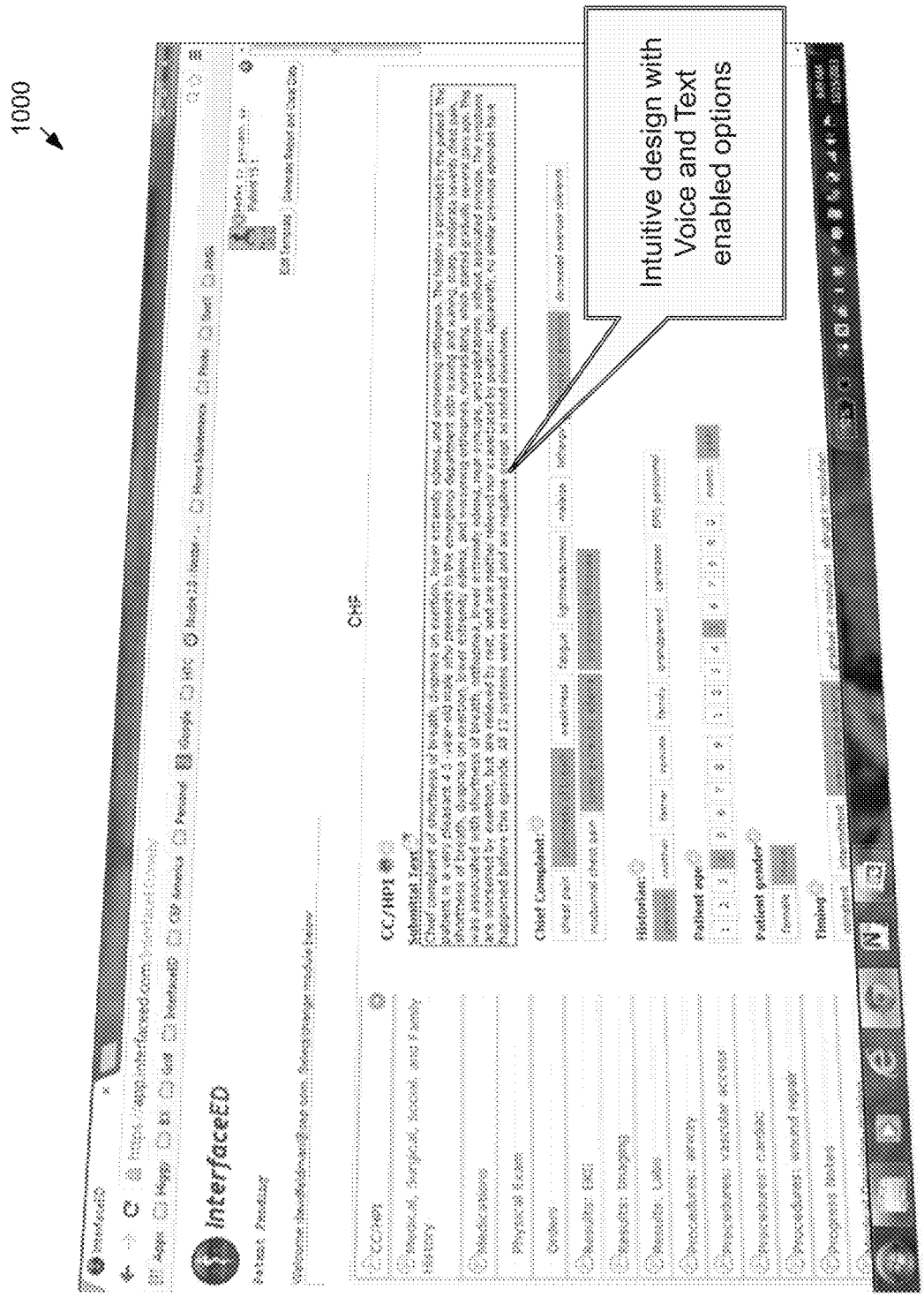
FIG. 10 is an example of a screenshot used to receive patient records.

FIG. 10 is an example of a screenshot 1000 used to receive patient records. The automated gathering agent using an interface to translate voice into text. The software can record patient responses and translate them directly into computer text thereby saving a scribe, physician, nurse or an employee time in typing the information. In one implementation, the interface allows both voice and text input simultaneously. The voice recognitions systems have evolved to include simple voice to text translation as well as invoking different commands on the computer. When in a paragraph writing mode, the voice recognition system translates voice to text. Using automated voice translation, allows the users hands to be free to do simultaneous testing and perform other actions at the same time. This results in overall efficient use of the time and decreases the inefficient time a physician spends with the patient.

Figure 11:
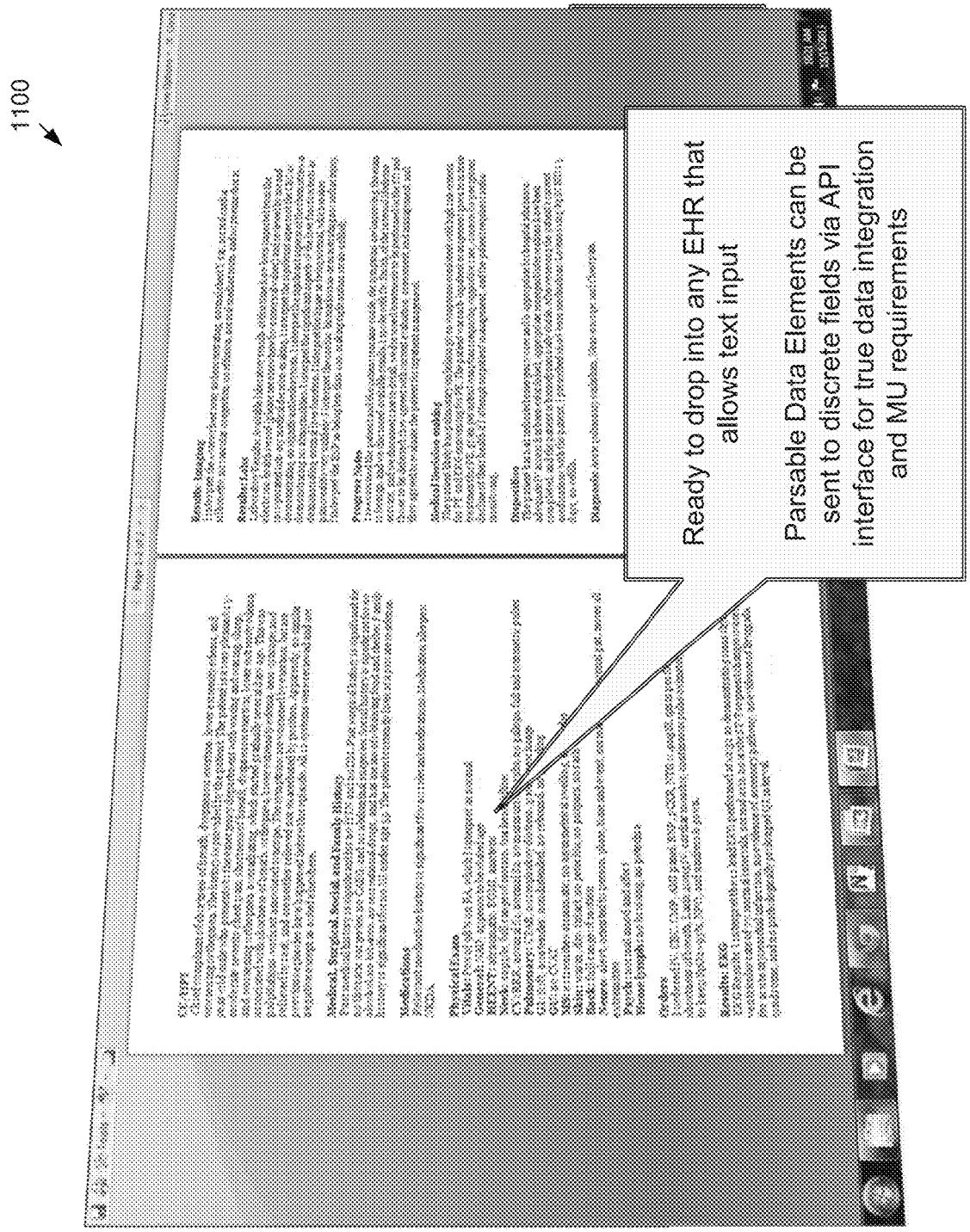
FIG. 11 is an example of a screenshot used to receive patient records.

FIG. 11 is an example of a screenshot 1100 used to receive patient records. The automated agent uses an interface that pulls text from readily available information texts related to different symptoms and illnesses. In one implementation, the text is further divided into different attributes that can be parsed and uploaded into different fields of a data store. In one implementation, the text used is part of an extensible markup language (XML). In one implementation, the text is part of an applicable programming interface (API). For example with the use of the parsable data elements, data can be uploaded with compatible computer systems in no time and without requiring additional processing. This saves time and resources in terms of work for administrative personnel who handle Information Technology ("IT") systems.

Figure 12:
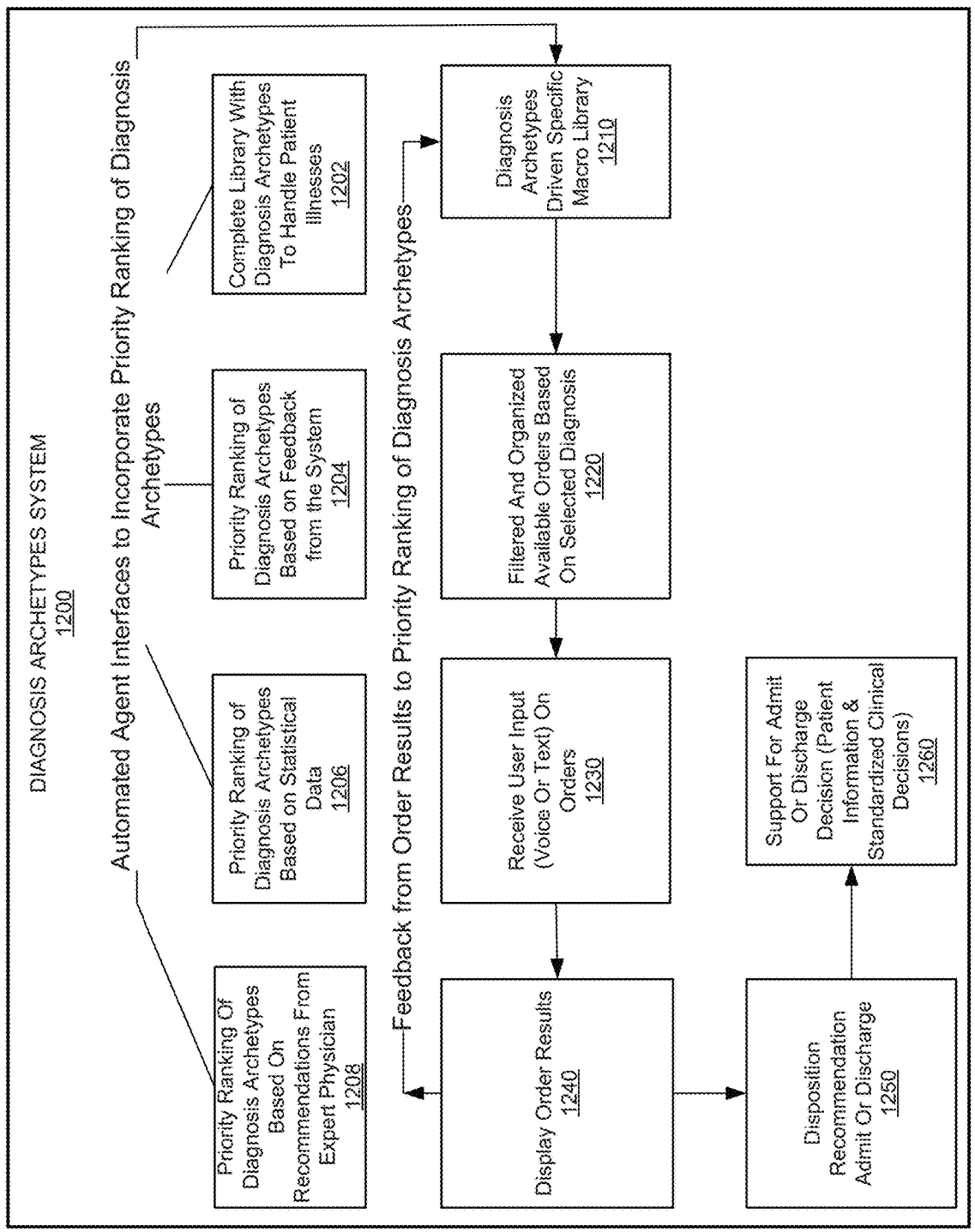
FIG. 12 depicts an example of a diagnosis based automated diagnosis patient archetypes system.

FIG. 12 depicts an example of an automated diagnoses archetypes system 1200. A complete library with super plurality of diagnosis automated diagnosis patient archetypes 1202 depicting hypothetical patients with different illnesses is used. The digital library has the potential to analyze all different permutations and combinations of different illnesses. For example, a patient may have two or more illnesses. The symptoms of such a state are automatically generated in a hypothetical automated diagnosis patient archetype. A person of ordinary skill in the art would understand that the automated diagnosis patient archetypes assist a physician to visualize the information in the computer world in a manner similar to the real world. Automated diagnosis patient archetypes could be implemented in a variety of different ways, including, for example one or more of the following, using database structures, object oriented programing, virtual objects or automation tools.

The automated diagnoses archetypes system creates an applicability score based on comparing patient parameters between the actual patient profile and the automated diagnosis patient archetypes from the super plurality of hypothetical diagnoses archetypes in the library. An automated agent 1204 uses an interface to generate the applicability score or priority ranking based on feedback from the automated diagnoses archetypes system itself. The system learns from its past decisions and evolves to create a feedback that is based on selections in the past. By adjusting itself and learning with each patient encounter, overtime, the system builds up its knowledge and becomes more accurate as to prioritizing different patient parameters, generating applicability scores and ranking different automated diagnosis patient archetypes for a given patient profile.

An automated agent 1206 uses an interface to generate applicability score based on statistical data. Statistical data can be based on the current physician's past selections into the system or generated based on all the physician's use of the system at a given location or remote locations. Statistical data parameters may be customized by an individual user of the system. For example if a user regards physician A to be an expert in a given field for a specific illness, the user of the system may be interested to view physician A's choices in the past for different types of symptoms. The automated diagnoses archetypes system automatically generates this applicability score and gives feedback based on such a selection.

An automated agent 1208 uses an interface to generate applicability score based on recommendations from an expert physician. The system may request feedback on different illnesses from an expert physician that may then be relied upon to generate applicability scores. For example, advances in medicine may enable the system to feed updates or additional approaches that could be mapped by an expert physician. A savvy user may prefer to create his or her own recommendations library based on customized practices that he or she prefers.

Implementations of the present disclosure are not limited to the specific automated agents interfaces or combination of the interfaces described herein. A person of ordinary skill in the art would understand the disclosure to include automated agents with interfaces to receive policies and recommendations from different types of sources including processing information from computer or non-computer based systems. Such interfaces could include gathering of diagnosis associated information from published medical journals, clinical trials and researches and other experimental medical databases.

Based on the generated applicability score, the automated diagnoses archetypes system selects a subset of the super plurality archetypes for further processing at an automated agent 1210. For example, automated diagnosis patient archetypes that can only be related to a male patient are eliminated when the patient is a female. The system by narrowing the automated diagnosis patient archetypes continues to work towards processing and matching the patient profile to a hypothetical automated diagnosis patient archetype. The active subset of automated diagnosis patient archetypes are then used by an automated agent 1220 to emphasize order selections that would help eliminate false positive automated diagnosis patient archetypes as well as eliminate false negatives and invoke automated diagnosis patient archetypes that have been eliminated or increase the current applicability score for a particular automated diagnosis patient archetype.

A user of the system does not have to manually analyze the huge amount of meta-data associated with the patient and speculate on the possibilities of what additional information is needed or missing. The system gives recommendations using different customized user interface emphasis techniques. An automated agent 1230 can then receive user input on different order selections using voice or text commands. The voice or text commands would be associated with a user profile. For example, a scribe may have a different level of authority to invoke order selections than a physician or nurse user.

The automated diagnoses system may be integrated to automatically receive order results from different tests conducted at the same or remote locations. An automated agent 1240 displays order results using contextual relevance for a given patient profile. For example, order results that have red flags in them are given higher visual priority. Normal or routine results are given priority based on the context. A normal result of a patient parameter may help rule out or reduce an applicability score of an automated diagnosis patient archetype and hence would be prioritized earlier in the list with emphasis.

Based on the applicability score, a user may narrow it further by making his or her final selections or request further narrowing of the subset of patient profiles using feedback from the system based on the order results. The automated agent 1210 processes the additional information from the order results to further narrow or revise the subset of automated diagnosis patient archetypes. As shown in FIG. 12, the subset of automated diagnosis patient archetypes can go through multiple iterations through automated agents at 1220, 1230 and 1240. An automated agent 1250 confirms the final disposition based on the applicability scores of the automated diagnosis patient archetypes that have the highest scores. The automated diagnoses archetypes system includes the support for the medical decision including the admit or discharge decision. Automated agent 1260 generates supporting information is automatically provided for any confrontational decision including patient parameter information, standardized clinical decisions and support from other data that is available to the system.

Figure 13:
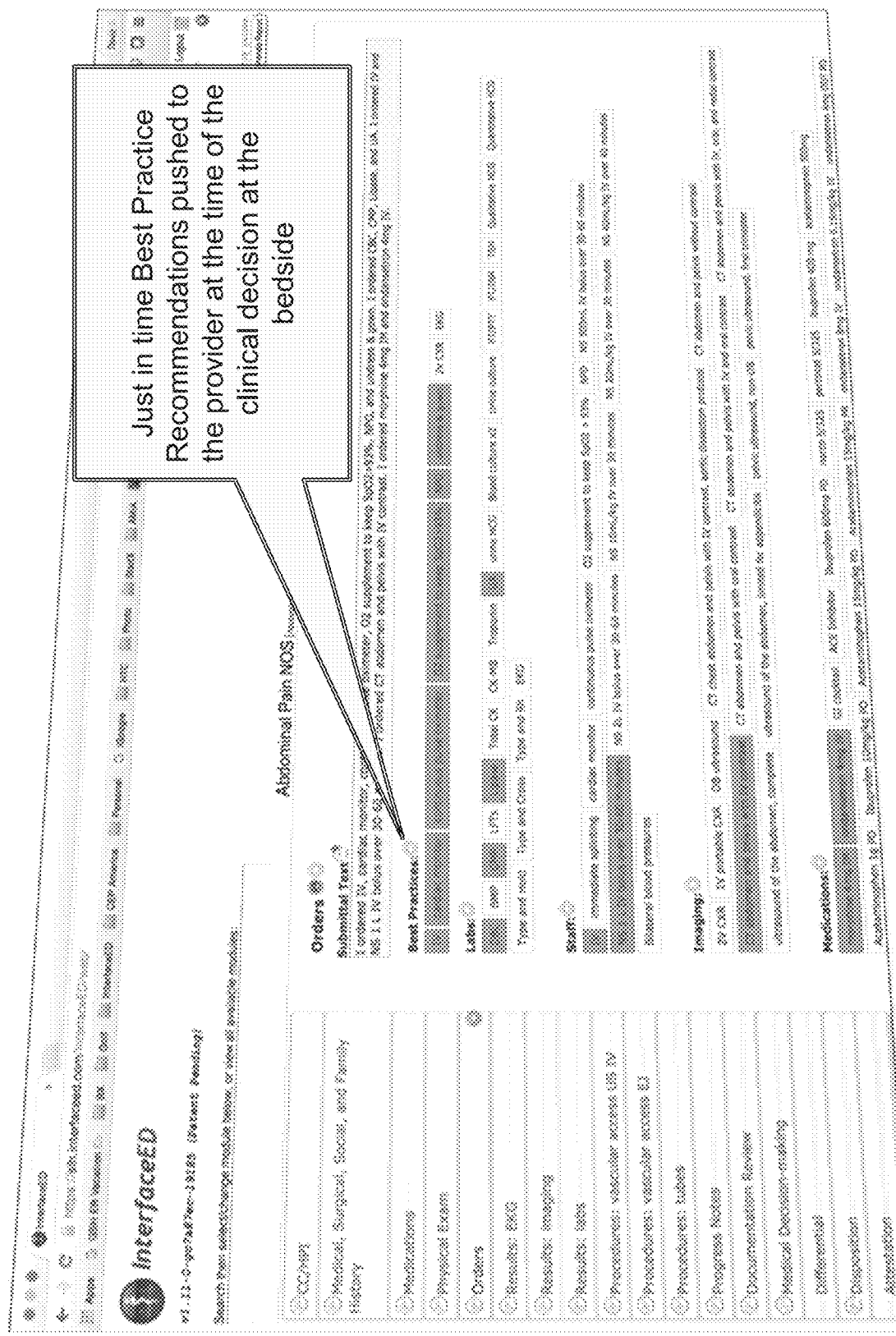
FIG. 13 is an example of a screenshot used to emphasize orders based on an automated agent ranking of different automated diagnosis patient archetypes.

FIG. 13 is an example of a screenshot used to emphasize orders based on an automated agent ranking of different automated diagnosis patient archetypes. For example, if the patient has a diagnosis that requires IV, cardiac monitor, continuous pulse orders, those orders are highlighted. The ones that are not of significance or relevant to the priority ranked diagnoses archetypes are not highlighted. A physician can select either highlighted or non-highlighted order base d on his or her own independent analysis. The automated diagnoses archetypes systems makes it easy and convenient for the physician to select the highlighted orders that are most likely to lead to relevant and significant results.

Figure 14:
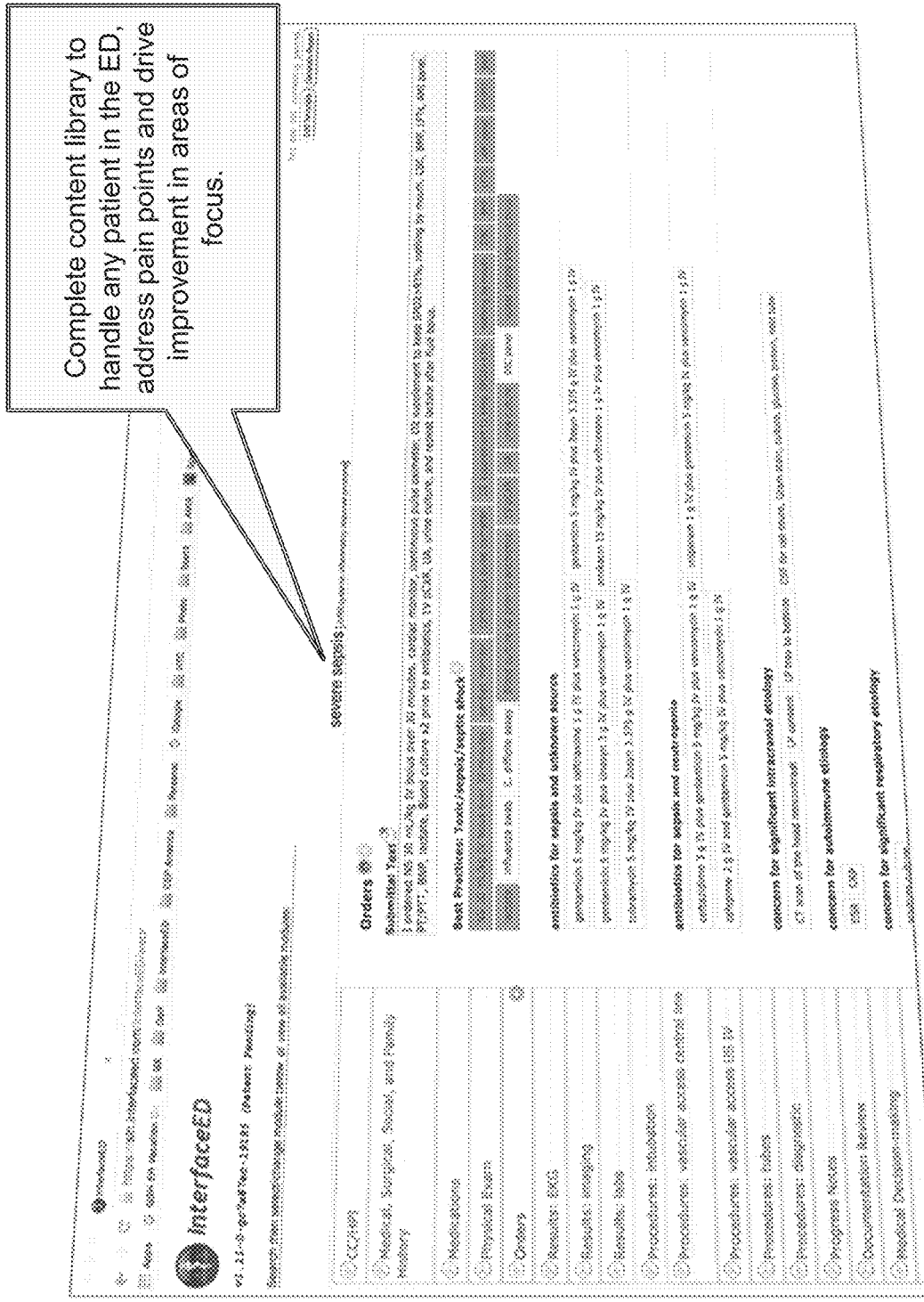
FIG. 14 is an example of a collection of automated diagnosis patient archetypes based on different medical diagnosis.

FIG. 14 is an example of a collection of automated diagnosis patient archetypes based on different medical diagnosis showing emphasis for different orders. For example, more than one diagnosis can be in play at the same time with respect to selecting orders. The system gives highlighted orders recommendation based on a given diagnosis. The automated diagnoses archetypes system has a complete collection of all illnesses and allows orders input related to more than one diagnosis at the same time.

Figure 15:
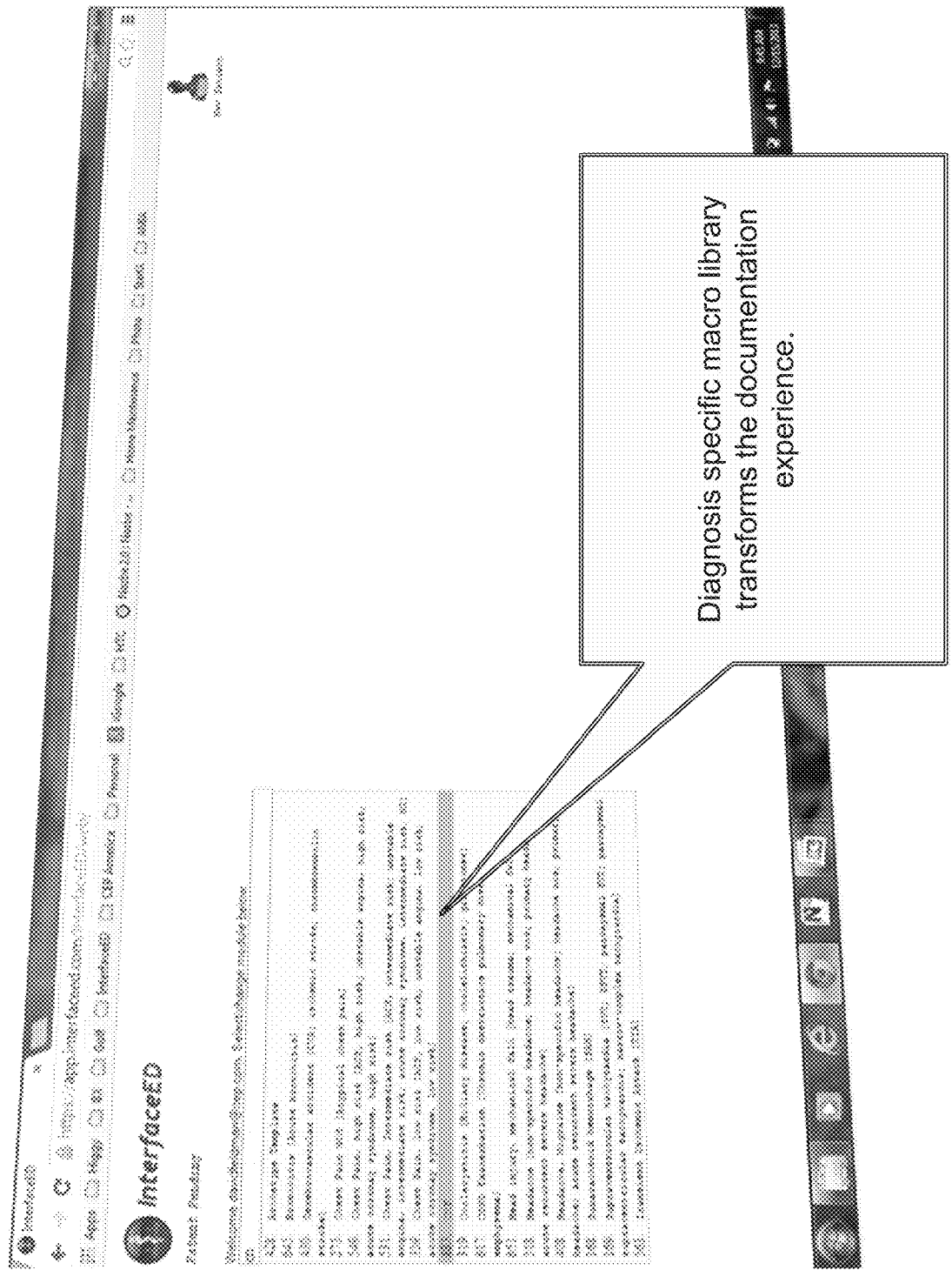
FIG. 15 is an example of a collection of automated diagnosis patient archetypes based on different medical diagnosis.

FIG. 15 is an example of a collection of automated diagnosis patient archetypes based on different medical diagnosis. For a given diagnosis archetype in play, the associated symptoms, orders and patient care are tied together giving a comprehensive and efficient display that serves a quick reference guide for the physician. Time in searching and navigating through vast amount of information available is optimized because the automated diagnoses archetypes system compiles information based on relevance including user interfaces and displays that are optimized for efficient look up, search, edits and revisions.

Figure 16:
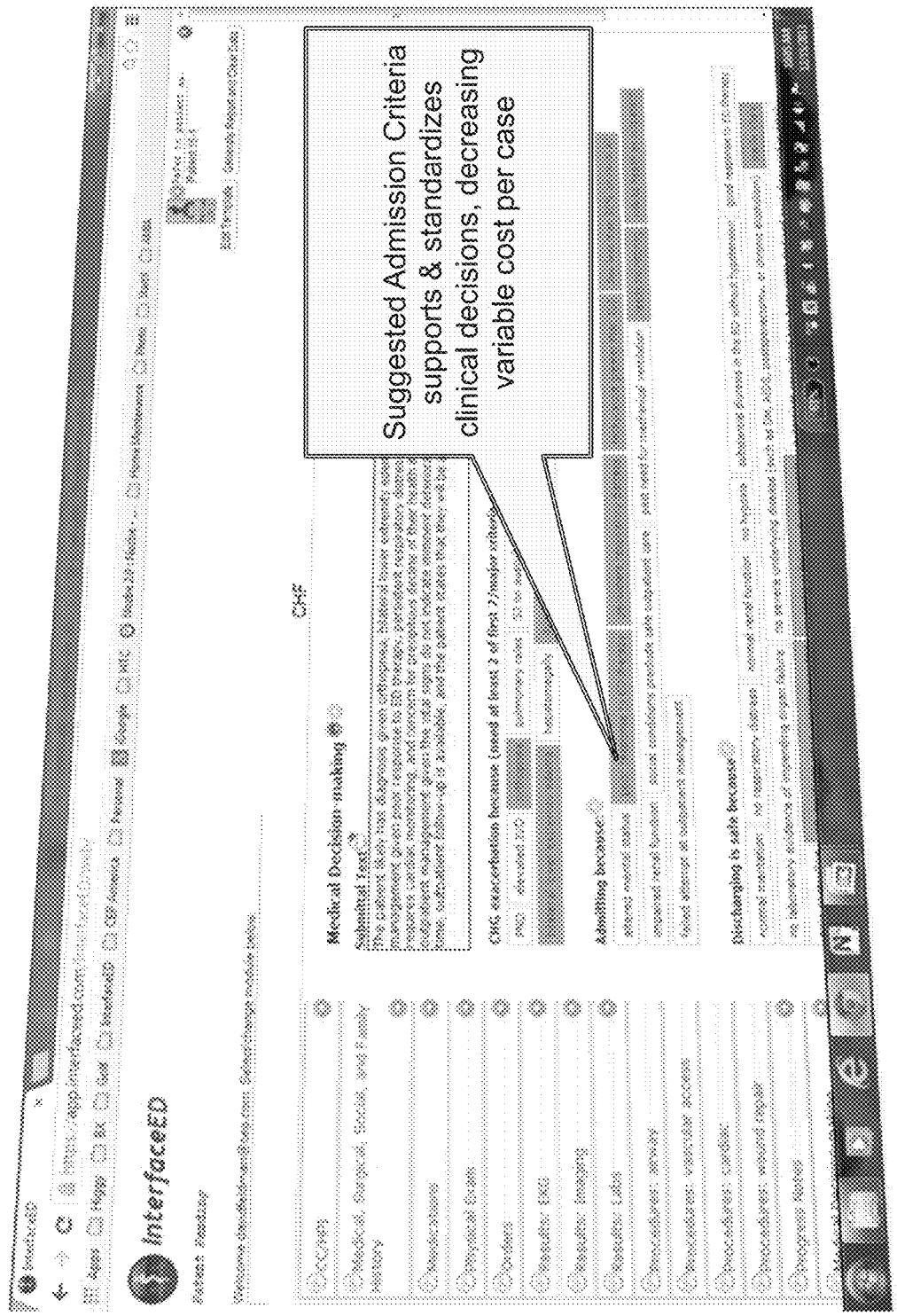
FIG. 16 is an example of a screenshot depicting support for admit or discharge decision.

FIG. 16 is an example of a screenshot depicting support for admit or discharge decision. A physician has to compile supporting data before he or she can make an admit or discharge decision. Many times, the physician has to navigate through different patient records to compile a list of supporting facts and order results. The automated diagnoses archetypes system compiles this information and makes it available for easy reference and use for the physician at the time of admit or discharge decision. By enabling this information to flow seamlessly through the system, the automated diagnoses archetypes systems saves physician time in looking up information that is already there in the system.

Figure 17:
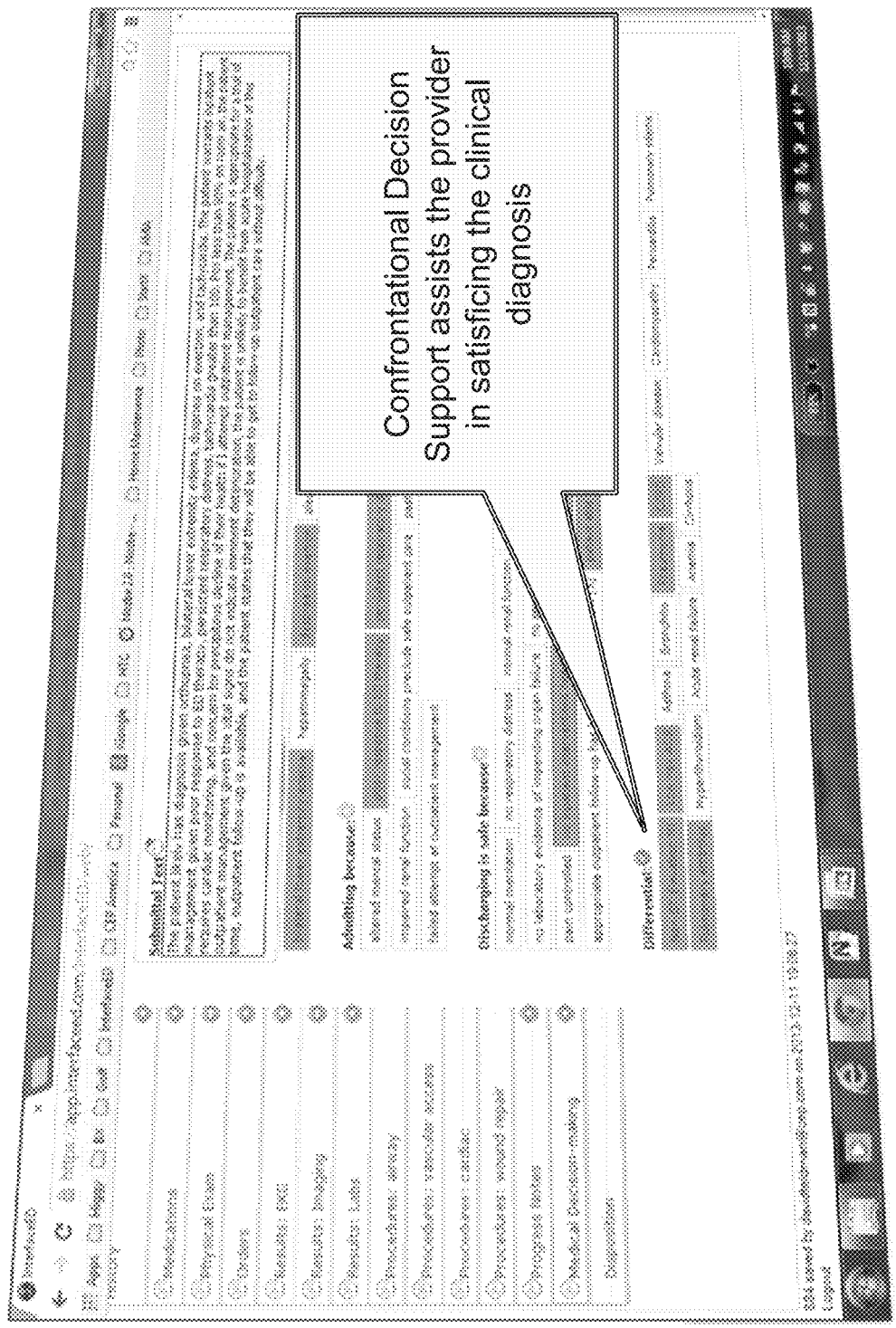
FIG. 17 is an example of a screenshot depicting support for a dynamic physician's diagnosis.

FIG. 17 is an example of a screenshot depicting support for a dynamic physician's diagnosis. Many times the physician has to make a confrontational decision that requires additional support in terms of clinical history or order results. The automated diagnoses archetypes system provides this information to back up physician decisions.

Figure 18:
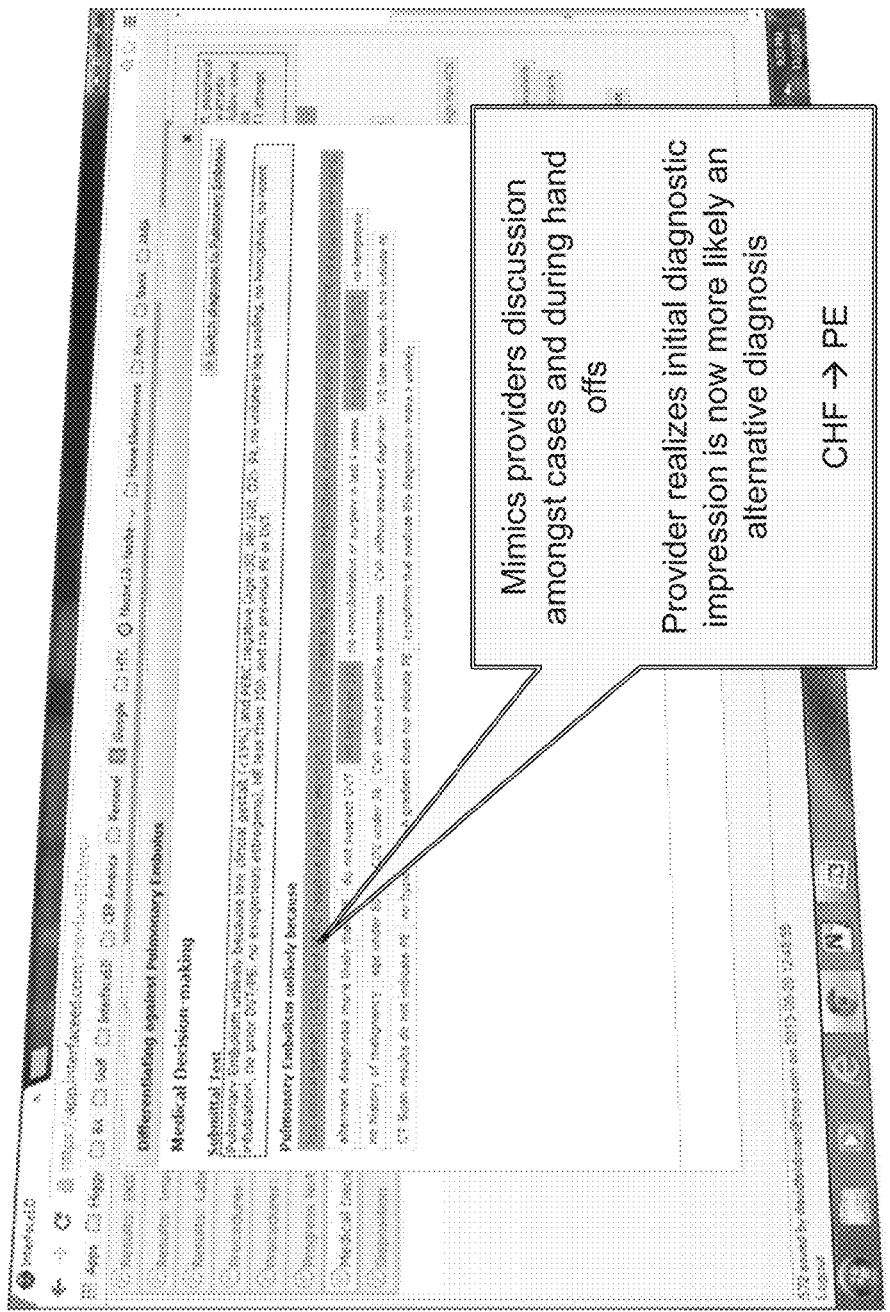
FIG. 18 is an example of a screenshot depicting support for a dynamic physician's diagnosis.

FIG. 18 is an example of a screenshot depicting support for a dynamic physician's diagnosis. For example, the automated diagnoses archetypes system mimics the discussion among different physicians on a case. The automated diagnoses archetypes system allows for different interactions including interactions with more than one diagnosis. Such a system in many instances can generate different and flexible diagnosis recommendations that would simulate different physician opinions and discussion. The physician using the system can then make an intelligent choice that has solid basis on the facts.

Figure 19:
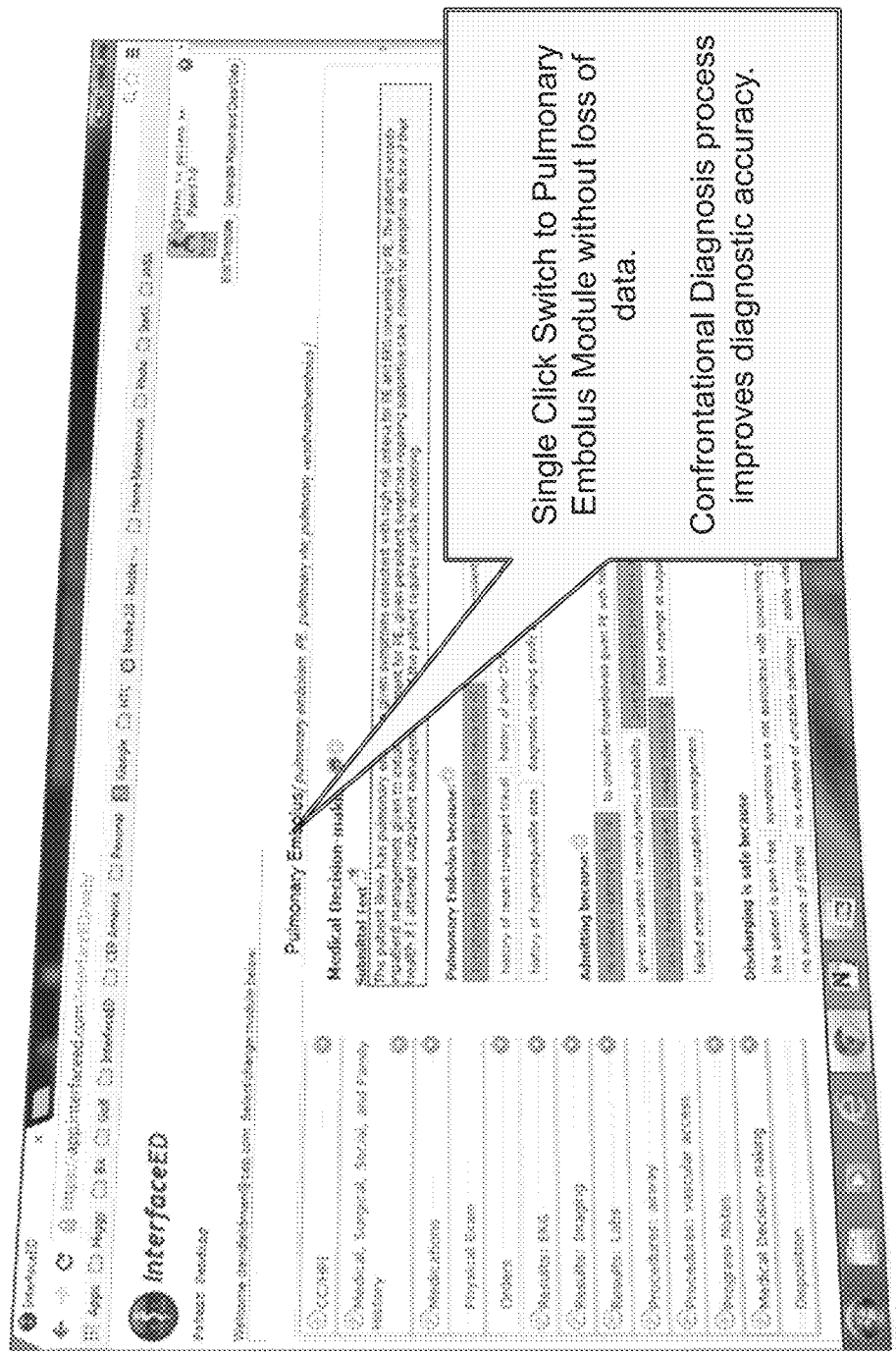
FIG. 19 is an example of a screenshot depicting support for a dynamic physician's diagnosis.

FIG. 19 is an example of a screenshot depicting support for a dynamic physician's diagnosis. At any given time or flow in the system, the physician may change his or her primary opinion on the diagnosis that is most relevant to a given patient. The automated diagnoses archetypes system allows such a switch without losing information that is associated and saved with an older diagnosis. By allowing more than one diagnosis and single click switch to change the highest priority on any of the diagnosis, the physician is able to navigate the support on any confrontational decisions seamlessly.

Figure 20:
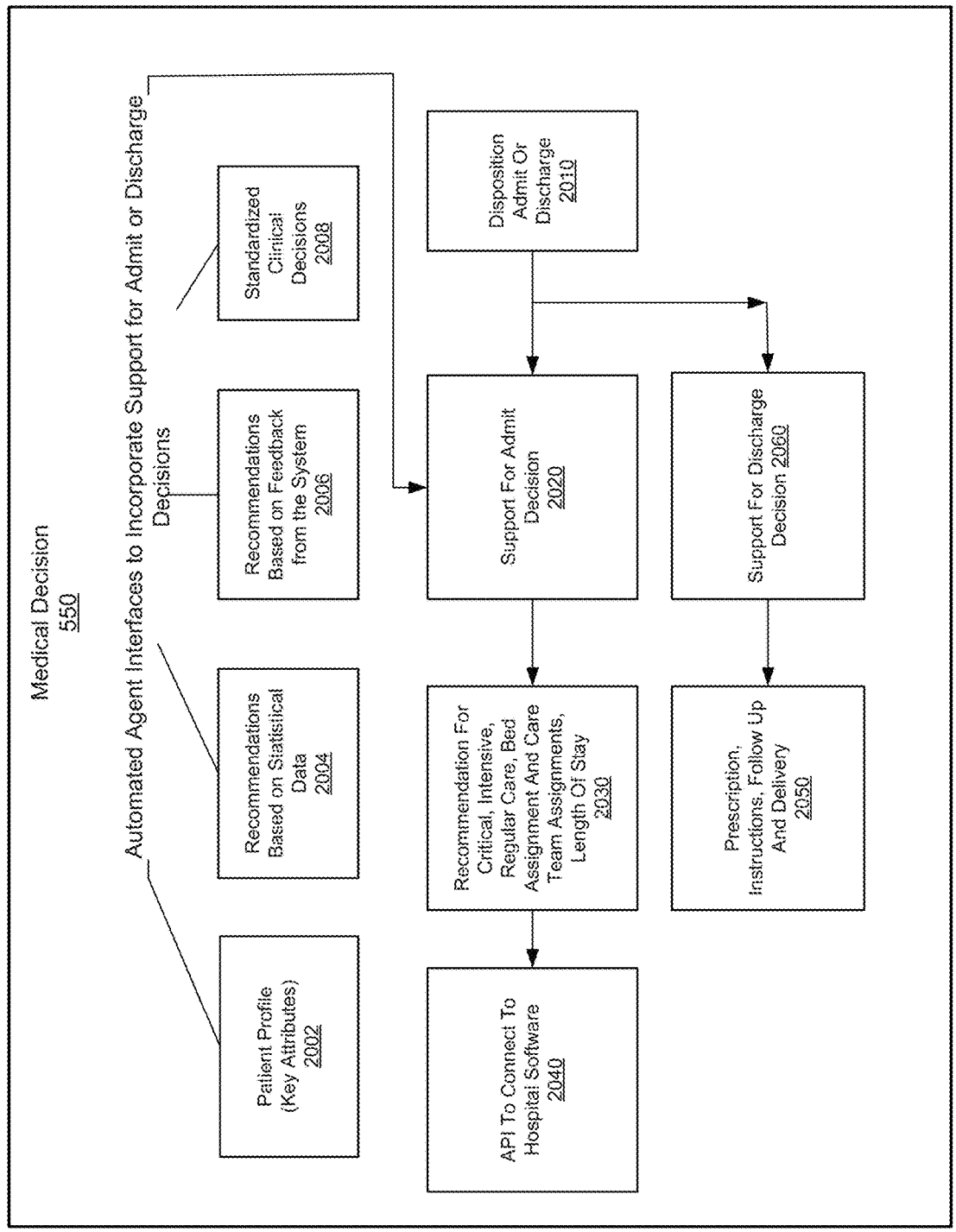
FIG. 20 is an example of a system depicting medical decision.

FIG. 20 is an example of a system depicting an automated agent for confirming a medical decision for the patient profile. An automated agent 2002 filters and organizes patient parameters information that is relevant to the medical decision by the medical decision recommendation agent 550. An automated agent 2004 filters and organizes contextual data from the statistical data fields that is relevant to the medical decision. Another automated agent 2006 filters and organizes data from the feedback of the use of the automated diagnoses system itself. Automated agent 2008 filters and organizes clinical decisions that support the medical decision. Based on the medical decision, the patient disposition decision regarding admit or discharge can also be made using an automated agent at 2010. The support data gathered from different automated agent interfaces is then collected and reported at automated agent 2020 that supports admit decision. In one implementation, the automated diagnoses archetypes system includes an automated agent 2030 that provides recommendation for critical, intensive or regular care, selects parameters for bed assignment, care team assignments and length of stay based on the patient profile.

In one implementation, a similar support data is gathered from different automated agent interfaces, collected and reported to an automated agent 2060 that supports discharge decision at 2060. An automated agent 2050 may also recommend prescription, instructions and follow up actions and delivery of those actions at the time of discharge. An automated agent 2040 may provide the available processed information to another application software using an application programming interface ("API") or other known techniques including push/pull, XML etc. Such interfaces are compatible with pre-existing software and computer systems. For example, the automated diagnoses system is compatible with ontology system providers SNOMED CT and LOINC.

Figure 21:
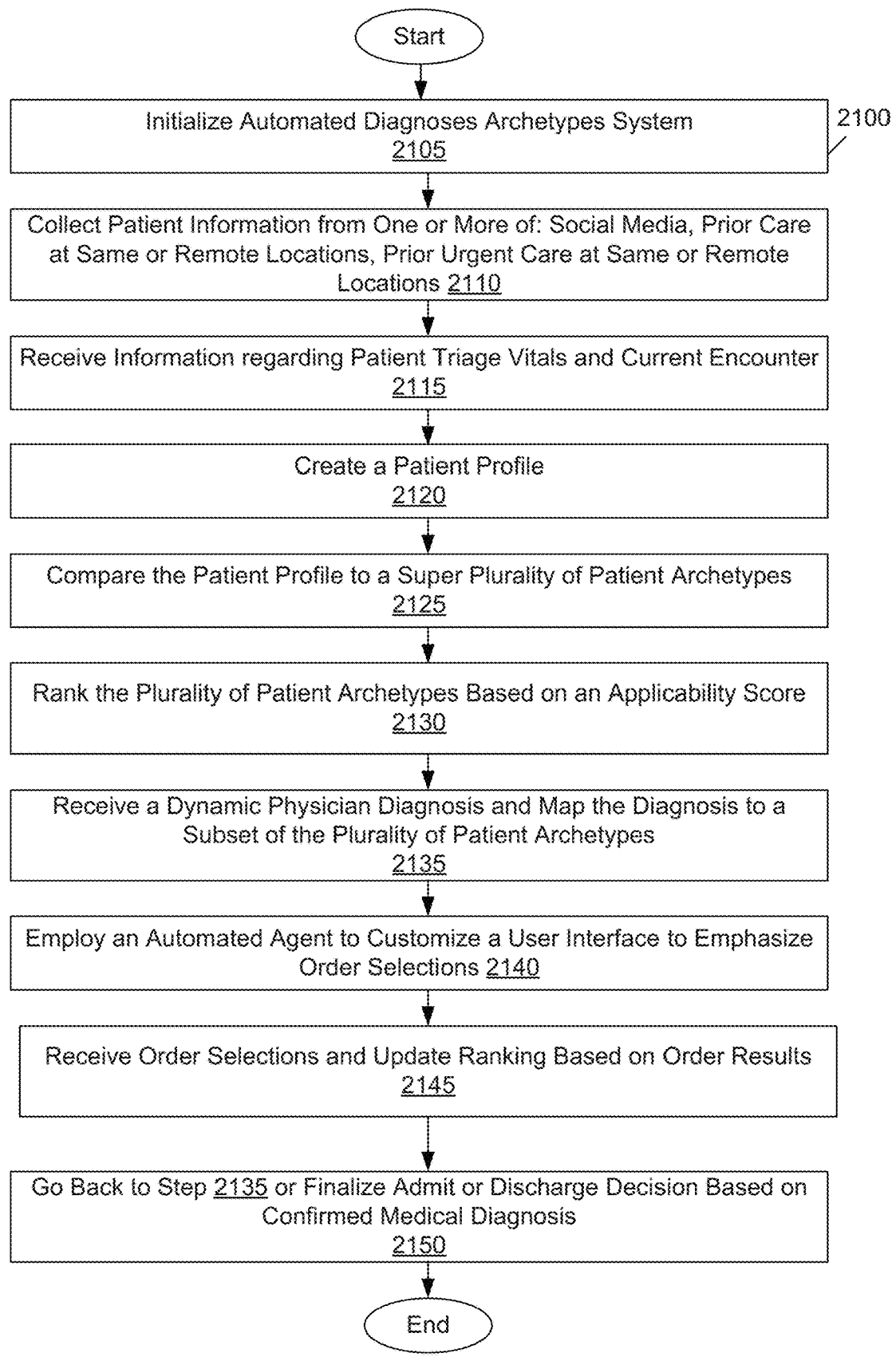
FIG. 21 depicts a flowchart of an example of a method of automated diagnoses based on automated diagnosis patient archetypes that help prioritize health data that is relevant to a dynamic physician's diagnosis.

FIG. 21 depicts a flowchart 2100 of an example of a method of automated diagnoses based on automated diagnosis patient archetypes that help prioritize health data that is relevant to a dynamic physician's diagnosis. At block 2105, the automated diagnoses archetypes system is initialized. At block 2110, automated agents collect information from different sources to for the patient profile. The sources could be at the current location or one or more remote locations. Examples of sources include information from social media, prior care, or prior urgent care. At block 2115, the automated agent receives information regarding patient triage vitals and current illness or encounter. Information regarding current encounter may be received using patient interview. The automated diagnoses archetypes system provides automated agents for note creation using voice or text. In one implementation the user interface on the computer system for getting data on current encounter is optimized based on initial feedback on symptoms. For example, such a user interface may use auto-fill text fields, one click mouse options for different data fields or use a library of already compiled intake notes that can be modified faster than creating the notes from scratch. At block 2120, the automated diagnoses archetypes system creates a comprehensive patient profile by compiling and processing information received from all of the different sources. At block 2125, the patient profile is compared to a super plurality of automated diagnosis patient archetypes. The comparison is based on mapping or identifying relevant patient parameters for a given illness. At block 2130, the automated diagnoses archetypes system generates an applicability score for each of the automated diagnosis patient archetypes and subsequently ranks the automated diagnosis patient archetypes based on the applicability score. For example, some of the automated diagnosis patient archetypes would clearly not be applicable for a given patient profile. Such automated diagnosis patient archetypes could be given a zero applicability score. A subset of the automated diagnosis patient archetypes would be selected for further processing. At block 2135, an automated agent receives a dynamic physician diagnosis and maps the diagnosis to a subset of the plurality of automated diagnosis patient archetypes for further processing. At block 2140, an automated agent is employed to customize a user interface to emphasize different order selections based on current active subset of automated diagnosis patient archetypes. At block 2145, the automated diagnoses archetypes system receives selection of orders and queues the system to wait for order results. Once the system receives order results, the automated diagnoses archetypes system updates the applicability score and ranking of the active subset of the automated diagnosis patient archetypes. At block 2150, the active subset of automated diagnosis patient archetypes is further narrowed based on the order results and updated applicability scores. The user can then finalize the medical diagnoses or go back to block 2135 to order more tests and investigate the patient profile further.

Figure 22:
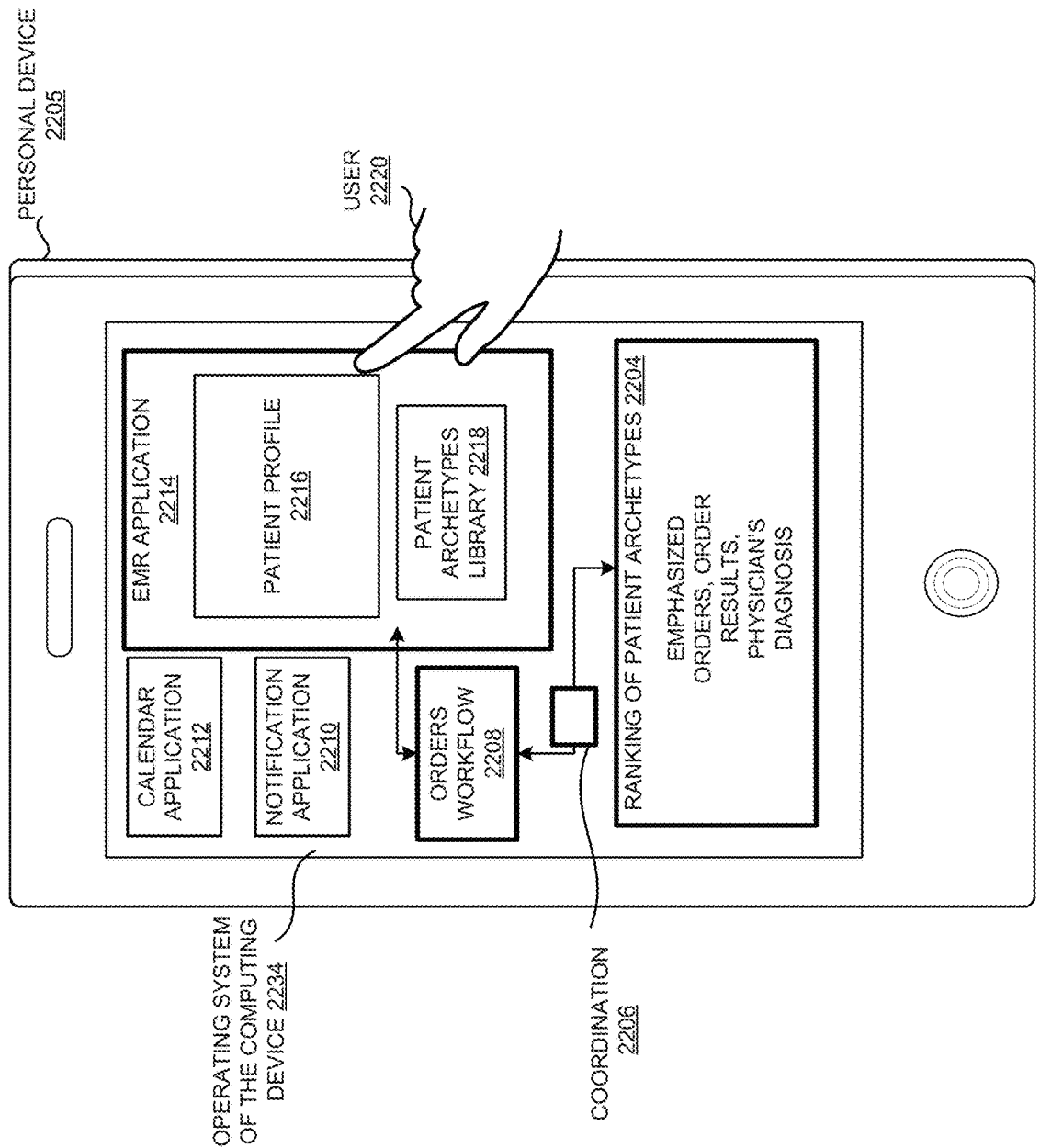
FIG. 22 depicts an example of a personal device that has an application interface to interact with the automated diagnoses based on automated diagnosis patient archetypes system.

FIG. 22 depicts an example of a personal device that has an application interface to interact with the automated diagnoses based on automated diagnosis patient archetypes system. The physician/scribe client system(s) 605 can be installed on a personal device 2205. The personal device 2205 has an operating system 2234. The operating system 2234 has different applications including the client interface to the automated diagnoses archetypes system. The calendar application 2212 may be integrated with the appointments or patient walk-ins. The notification application 2210 may be integrated with the alerts from the automated diagnoses archetypes system. For example, an alert on the archetype device could notify the user when an order result is posted or received on the system. The orders workflow 2208 could be used to interface with the user and the automated diagnoses archetypes system to make order selections. The electronic medical records application 2214 includes interfaces to the patient profile automated agent 2216 and automated diagnosis patient archetypes library 2218. The active set of automated diagnosis patient archetypes based on applicability score for a given patient can be viewed and further narrowed using the automated agent 2204 and selecting one or more medical diagnoses. The personal device 2205 promotes overall coordination and compatibility between different applications using the automated agent 2204. The user 2220 can select, view, modify different aspects of the automated diagnoses archetypes system on his personal device.

Figure 23:
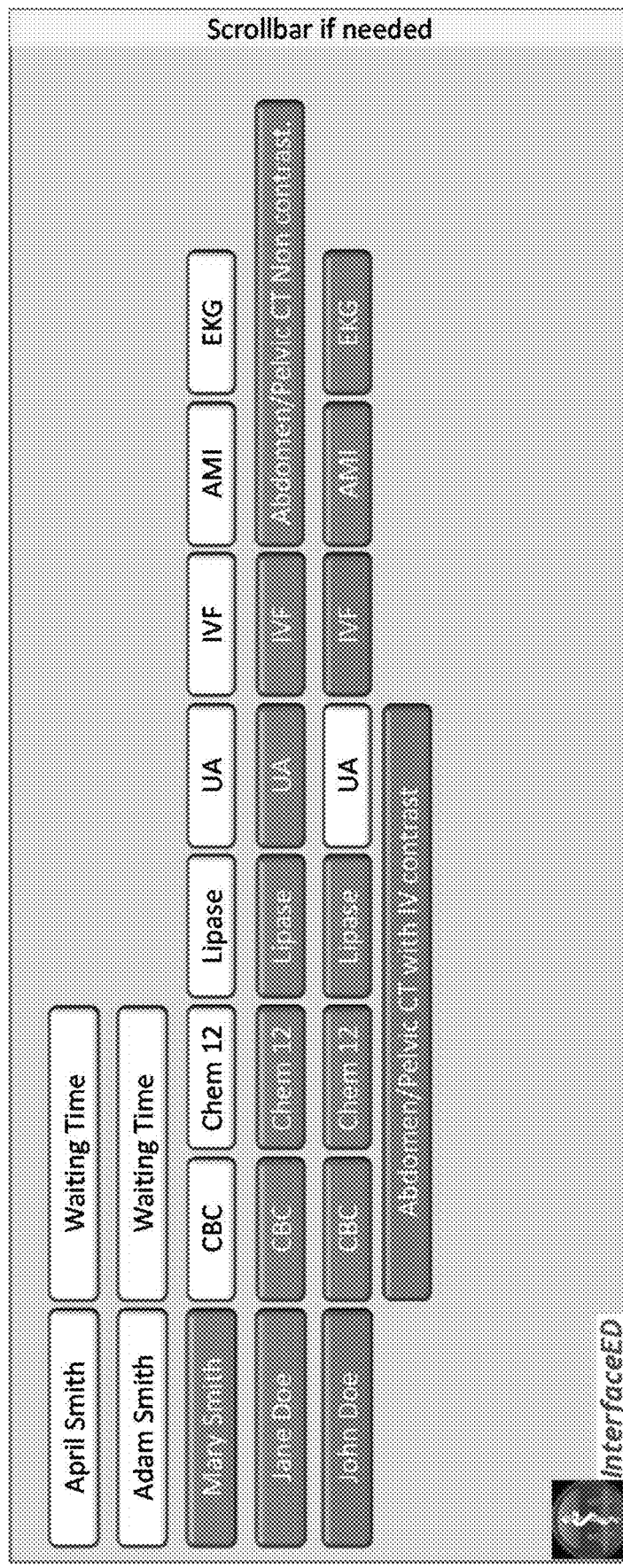
FIG. 23 depicts a screenshot of a dashboard of an automated diagnoses system.

FIG. 23 depicts a screenshot of a dashboard of an automated diagnoses system. The example dashboard shows different rows of patients outlined and the corresponding stage of processing the patient encounter. The dashboard also highlights the orders that have been placed into the system and are waiting results. Based on order results, the corresponding panes change color to green or red depending on whether a result is favorable or alarming. If a result is alarming, the red pane switch allows the physician to quickly focus and review such an order result. The dashboard gives a one line summary of what is going on currently with a patient.

Figure 24:
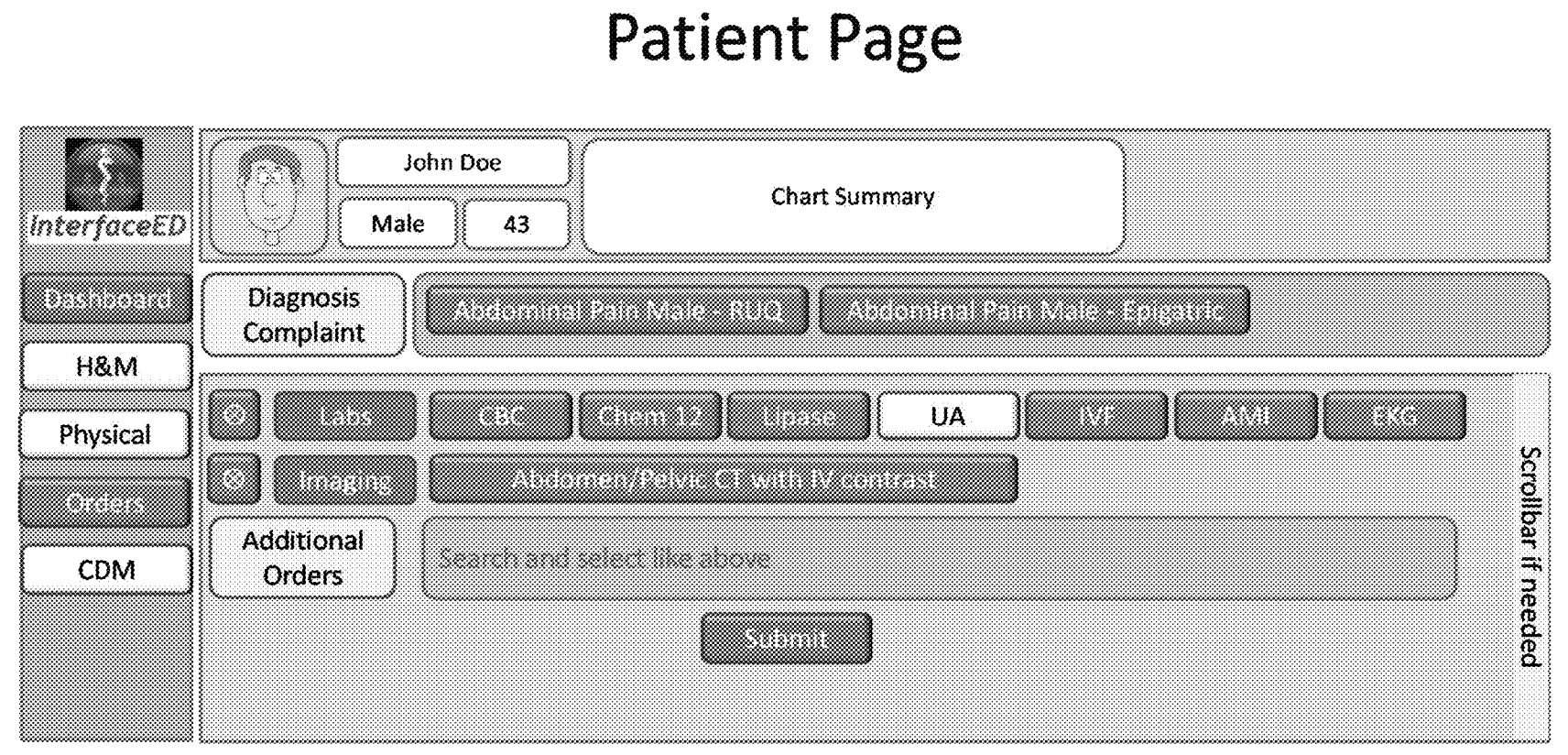

FIG. 24 depicts an example of a customized graphical user interface displaying patient profile. For example, a detailed view of a selected patient shows additional options with regards to care and orders. The detailed user interface screen for a patient is also highlighted based on priority, significance and relevance to the current patient encounter.

Figure 25:
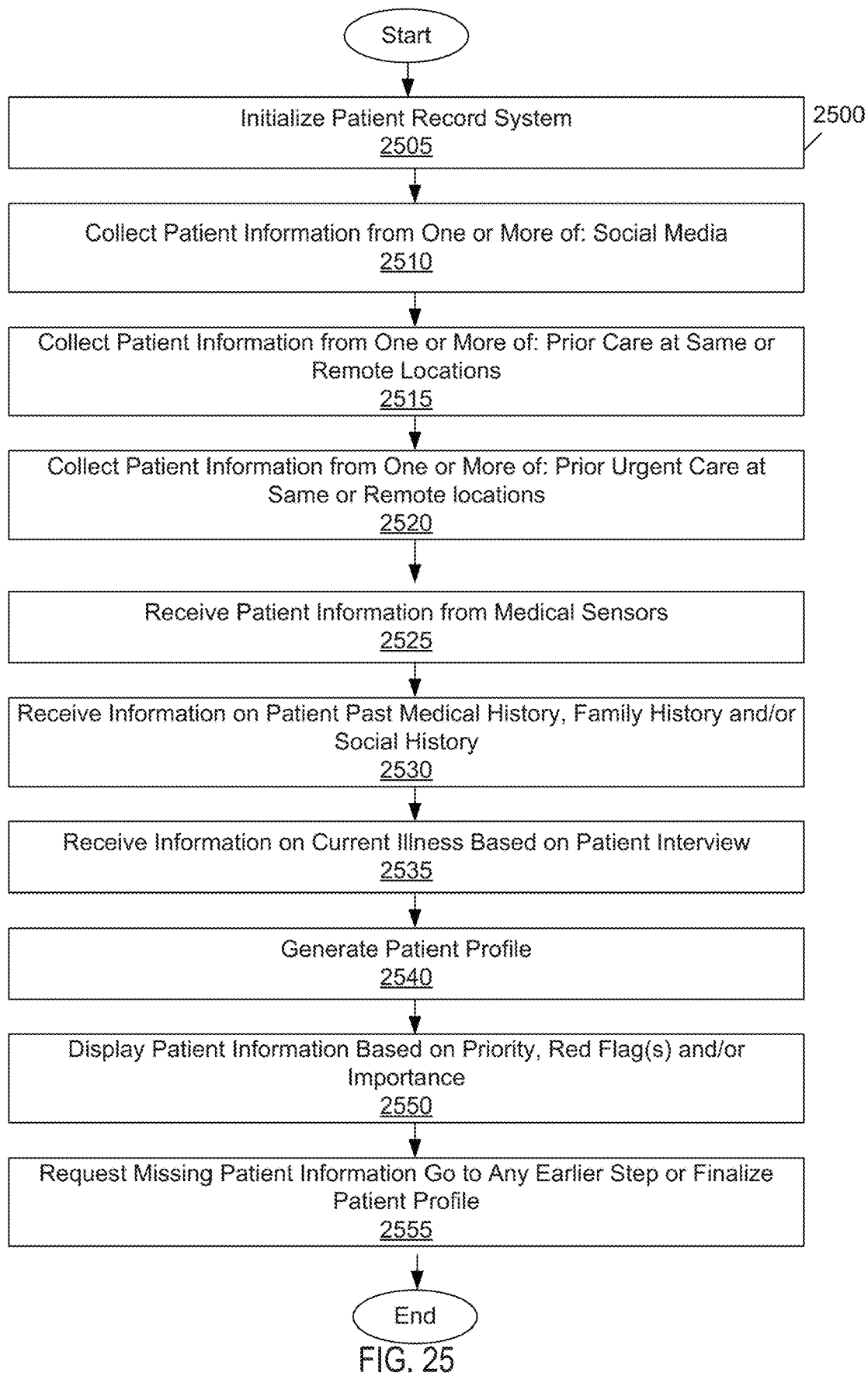
FIG. 25 depicts a flowchart of an example of a method to receive patient information.

FIG. 25 depicts a flowchart 2500 of an example of a method to receive patient information. At block 2505, the patient record system is initialized. At block 2510, an automated agent collects patient information from one or more of social media networks. At block 2515, an automated agent collects patient information from one or more same or remote locations where the patient previously had received care. At block 2520, an automated agent collects patient information from one or more of the same or remote locations where the patient previously had received urgent care. At block 2525, an automated agent receives patient information from different medical sensors. For example, one type of medical sensor may be a health band or a smart watch that monitors heart rate, walking trends and blood sugar on a regular basis. In one implementation, the medical sensor may be given to the patient at the location. At block 2530, an automated agent receives information on patient past medical history, family history and/or social history. In one implementation, the automated agent using application programming interface under the health information exchange act to receive patient's electronic medical records. At block 2535, an automated agent receives information on current illness based on patient interview. The automated agent may use automated note creation using voice, text or a combination of voice and text inputs to create records relating to current patient illness. At block 2540, the automated diagnoses archetypes system generates a patient profile based on patient parameters compiled from information collected from one or more of the previous blocks. At block 2550, the patient profile is displayed using a customized user interface that shows information based on contextual relevance to the current illness. Sensitive information may be marked as red flags and/or information may be prioritized based on relevance and/or importance. At block 2555, the automated diagnoses system may request additional information by going to block 2555 or finalize the patient profile.

FIG. 26 depicts an example of different types of user interfaces used in the automated diagnoses archetypes system. The client system 2605 includes the interface to the automated diagnoses archetypes system. A user 2610 may be a scribe, physician, nurse, patient or any other employee who has access to the system. The user may use an automated agent integrated with touchscreen 2615, a keyboard or joystick 2620, voice with natural language note creation 2625, or medical sensors 2630. Implementations of the present disclosure are not limited to the specific automated agents interfaces or combination of the interfaces described herein. A person of ordinary skill in the art would understand the disclosure to include automated agents with interfaces to receive information from different types of sources including processing information from computer or non-computer based systems. Such interfaces could include gathering of patient associated information with the use of optical scanner technology, image, audio or video processing or computer based databases.

Figure 27A:
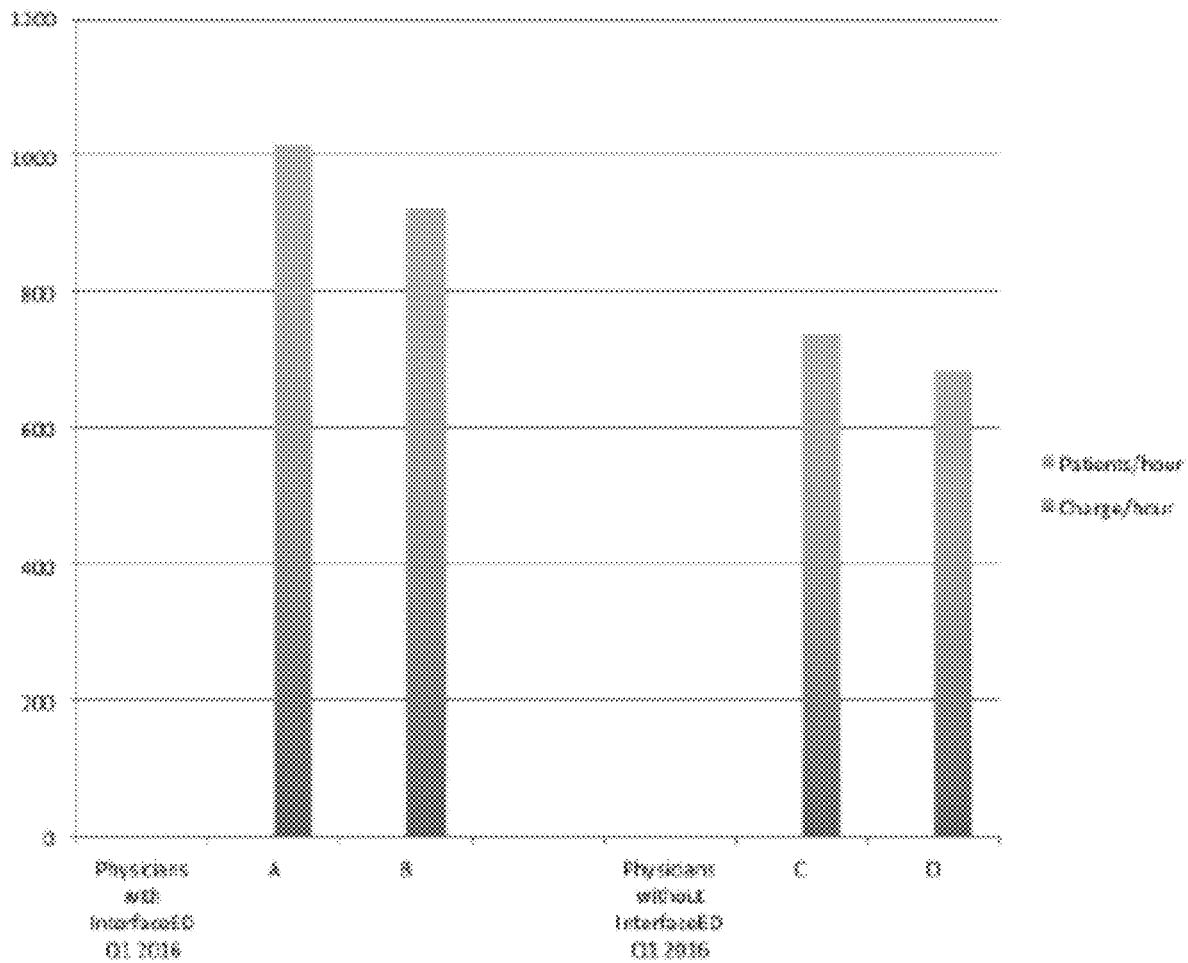
FIGS. 27A, 27B, 27C, 27D and 27E show examples of reports of comparing physician efficiency when using the systems and methods described herein.
Figure 27B:
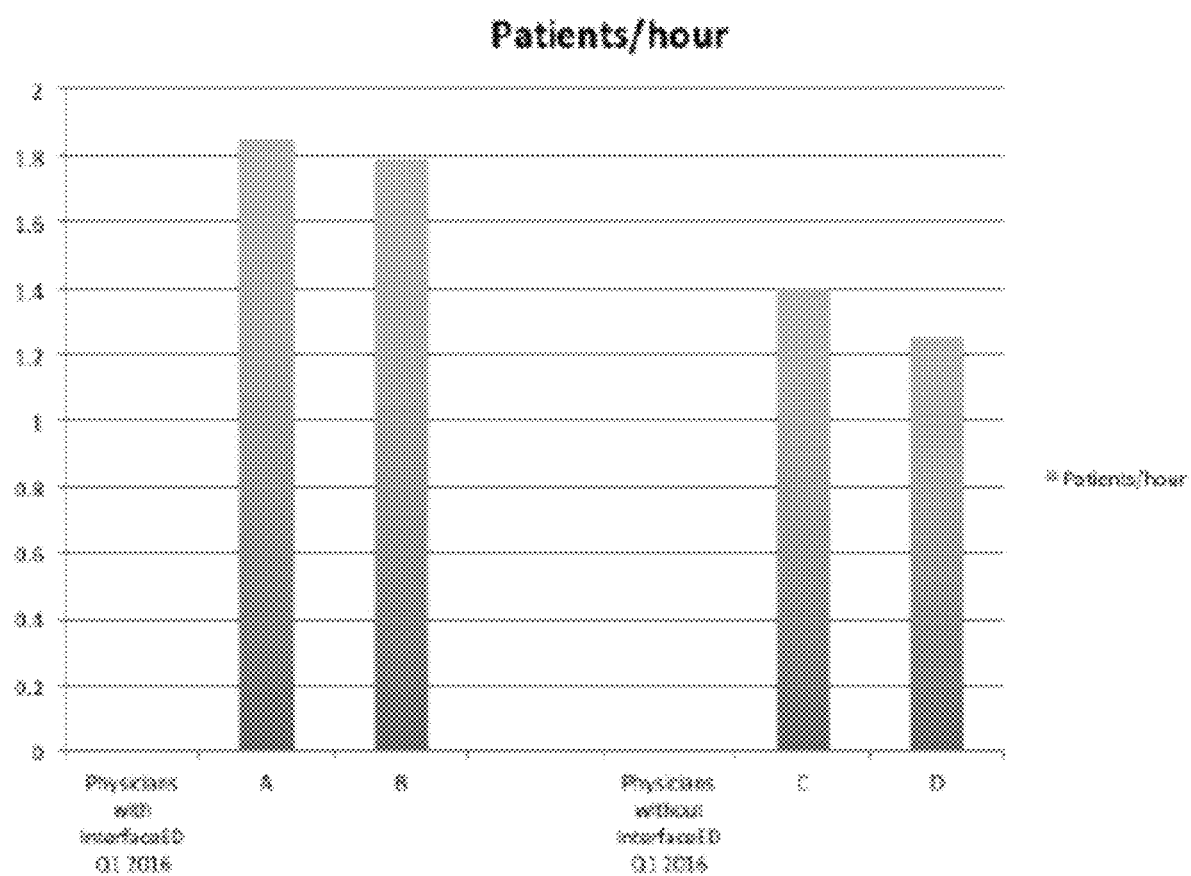
Figure 27C:
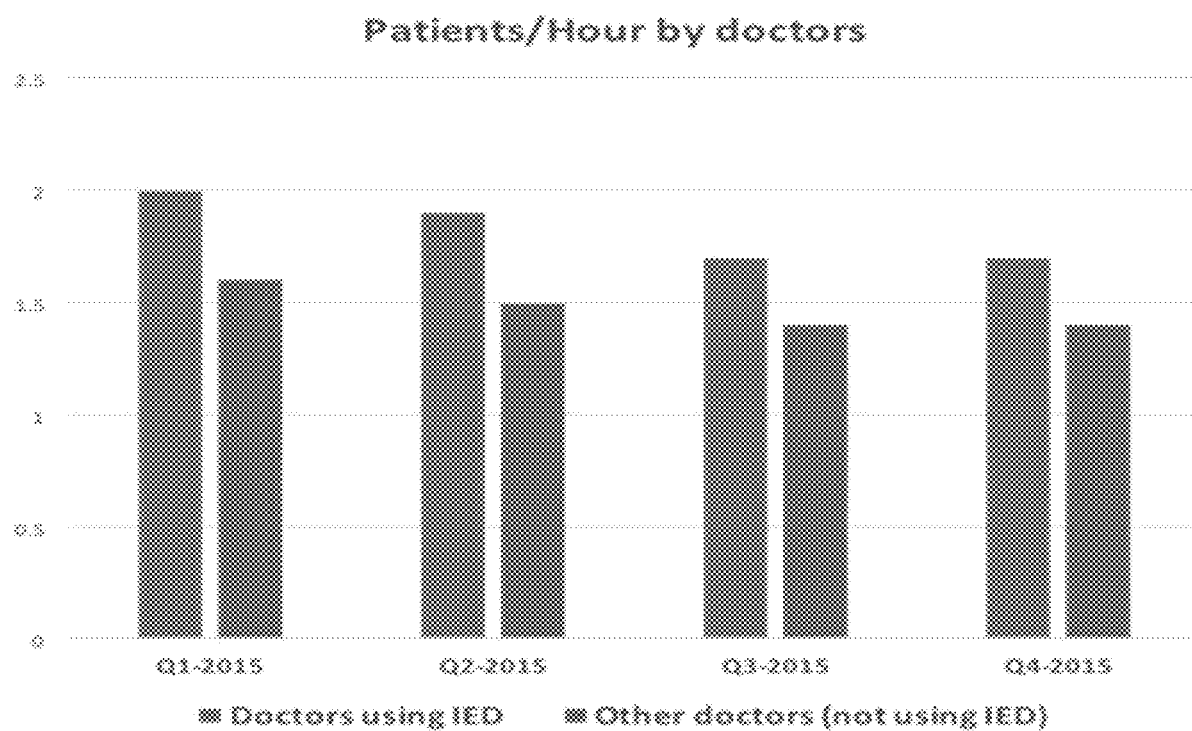
Figure 27D:
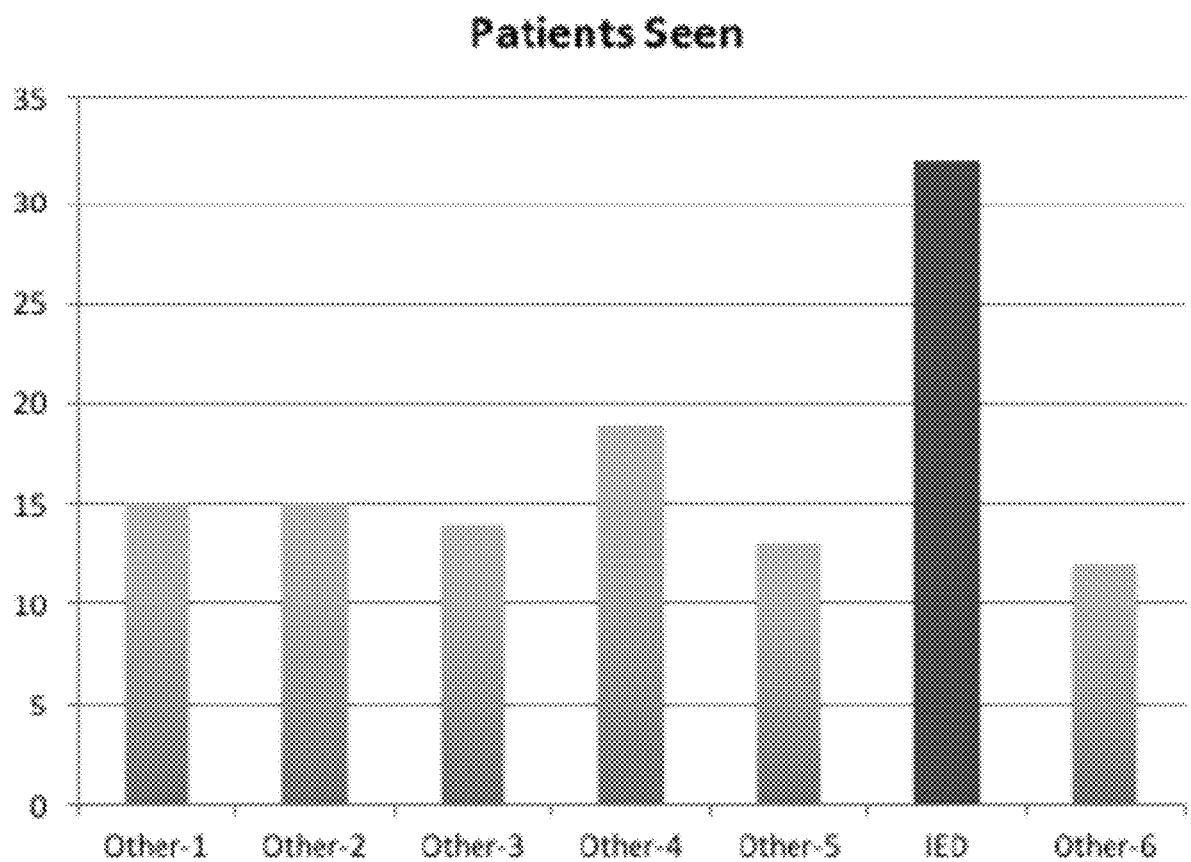
Figure 27E:
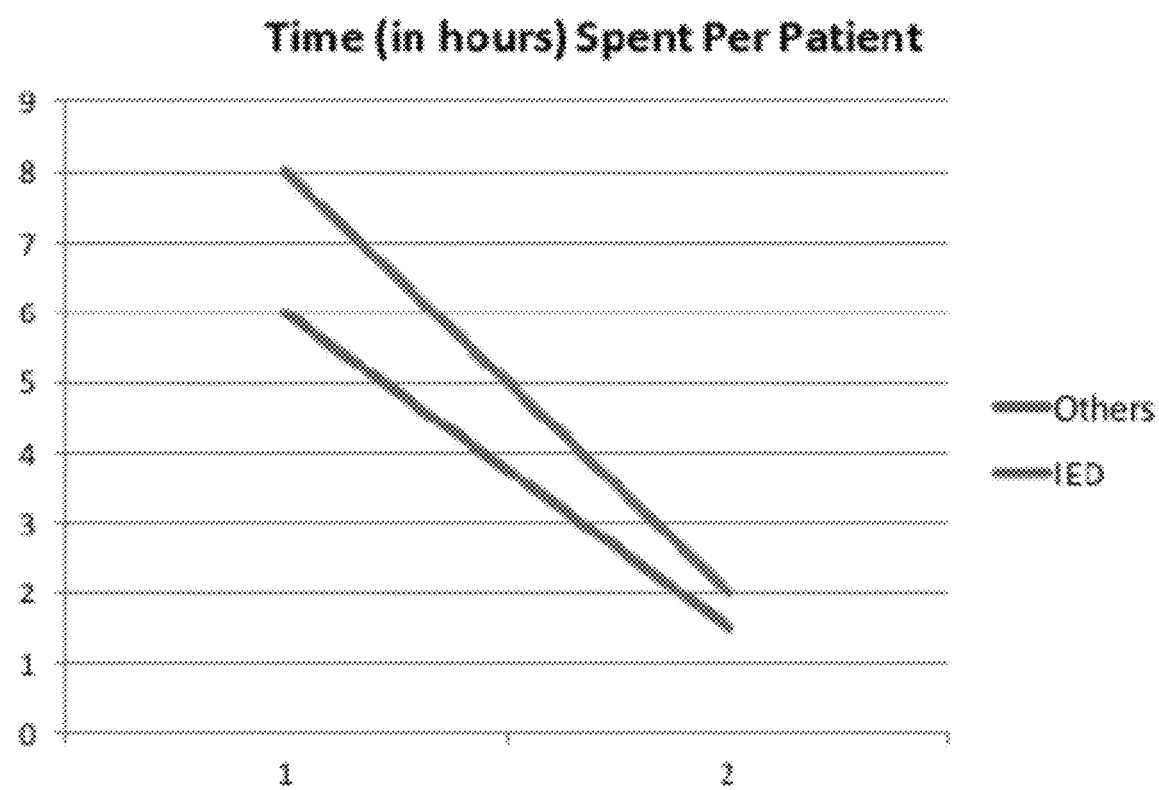

FIGS. 27A, 27B, 27C, 27D and 27E show examples of reports of comparing physician efficiency when using the systems and methods described herein, according to some implementations. Physicians using the automated diagnoses archetypes system are able to see more patients per hour and also charge more per hour. FIGS. 27A and 27B shows charts based on actual performance of two physicians from two different locations using the automated diagnoses archetypes system. Clearly, the graphs show that efficiency of the physicians is increased with the use of the automated diagnoses archetypes system. The automated diagnoses archetypes system promotes efficient use and processing of information that allows the physicians to focus their time and attention on issues that matter. Physicians no longer waste time on processing information that is not of relevance. FIG. 27C shows an annual report showing performance in four quarters for doctors using the automated diagnoses archetypes system and doctors not using them. FIG. 27D shows that the number of patients seen by the doctors using the automated diagnoses archetypes system is higher than those using six different systems available in the industry. FIG. 27E show that the time spent by doctors using the automated diagnoses archetypes system is less than doctors not using the system. The statistical reports shared in FIGS. 27A-27E are based on real comparison and use of the automated diagnoses archetypes system.

Figure 28:
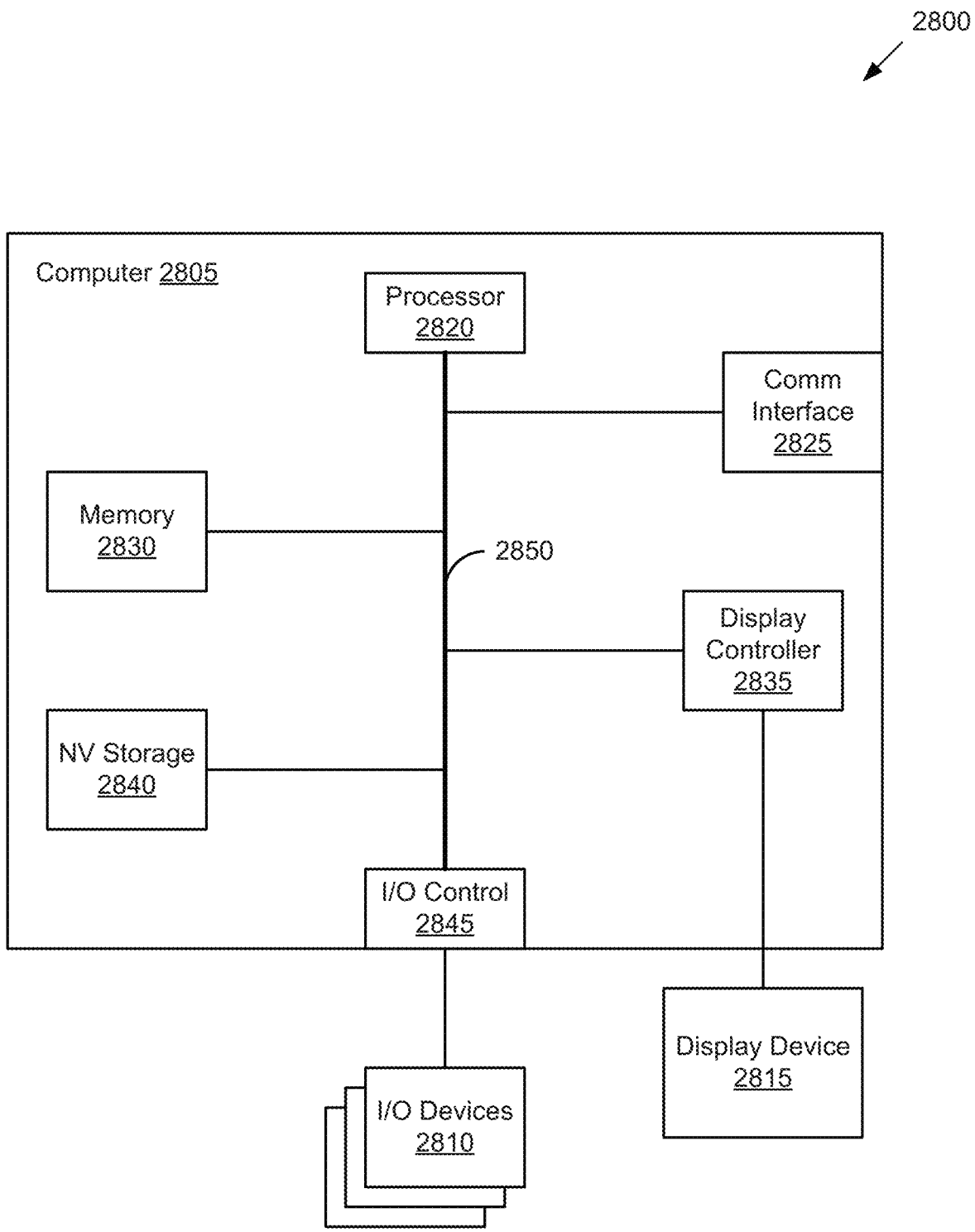
FIG. 28 depicts an example of a computer system.

FIG. 28 is a schematic diagram of computing device 2800 that can be used to implement the methods and systems disclosed herein, according to one or more implementations. FIG. 28 is a schematic of a computing device or a mobile device that can be used to perform and/or implement any of the implementations disclosed herein. In one or more implementations, client system 605 and/or server system 630 of FIG. 6 may be the computing device 2800.

The computing device may represent various forms of digital computers, such as laptops, desktops, workstations, personal digital assistants, servers, blade servers, mainframes, and/or other appropriate computers. The mobile device may represent various forms of mobile devices, such as smartphones, camera phones, personal digital assistants, cellular telephones, and other similar mobile devices. The components shown here, their connections, couples, and relationships, and their functions, are meant to be an example of a only, and are not meant to limit the implementations described and/or claimed.

FIG. 28 depicts an example of a system on which techniques described in this paper can be implemented. The computer system 2800 may be a conventional computer system that can be used as a client computer system, such as a wireless client or a workstation, or a server computer system. The computer system 2800 includes a computer 2805, I/O devices 2810, and a display device 2815. The computer 2805 includes a processor 2810, a communications interface 2825, memory 2830, display controller 2835, non-volatile storage 2840, and I/O controller 2845. The computer 2805 may be coupled to or include the I/O devices 2810 and display device 2815.

The computer 2805 interfaces to external systems through the communications interface 2825, which may include a modem or network interface. It will be appreciated that the communications interface 2825 can be considered to be part of the computer system 2800 or a part of the computer 2805. The communications interface 2825 can be an analog modem, ISDN modem, cable modem, token ring interface, satellite transmission interface (e.g. "direct PC"), or other interfaces for coupling a computer system to other computer systems.

The processor 2810 may be, for example, a conventional microprocessor such as an Intel Pentium microprocessor or Motorola power PC microprocessor. The memory 2830 is coupled to the processor 2810 by a bus 2850. The memory 2830 can be Dynamic Random Access Memory (DRAM) and can also include Static RAM (SRAM). The bus 2850 couples the processor 2810 to the memory 2830, also to the non-volatile storage 2840, to the display controller 2835, and to the I/O controller 2845.

The I/O devices 2810 can include a keyboard, disk drives, printers, a scanner, and other input and output devices, including a mouse or other pointing device. The display controller 2835 may control in the conventional manner a display on the display device 2815, which can be, for example, a cathode ray tube (CRT) or liquid crystal display (LCD). The display controller 2835 and the I/O controller 2845 can be implemented with conventional well known technology.

The non-volatile storage 2840 is often a magnetic hard disk, an optical disk, or another form of storage for large amounts of data. Some of this data is often written, by a direct memory access process, into memory 2830 during execution of software in the computer 2805. One of skill in the art will immediately recognize that the terms "machine-readable medium" or "computer-readable medium" includes any type of storage device that is accessible by the processor 2810 and also encompasses a carrier wave that encodes a data signal.

The computer system 2800 is one example of many possible computer systems which have different architectures. For example, personal computers based on an Intel microprocessor often have multiple buses, one of which can be an I/O bus for the peripherals and one that directly connects the processor 2810 and the memory 2830 (often referred to as a memory bus). The buses are connected together through bridge components that perform any necessary translation due to differing bus protocols.

Network computers are another type of computer system that can be used in conjunction with the teachings provided herein. Network computers do not usually include a hard disk or other mass storage, and the executable programs are loaded from a network connection into the memory 2830 for execution by the processor 2810. A Web TV system, which is known in the art, is also considered to be a computer system, but it may lack some of the features shown in FIG. 28, such as certain input or output devices. A typical computer system will usually include at least a processor, memory, and a bus coupling the memory to the processor.

Various implementations of the systems and techniques described here can be realized in a digital electronic circuitry, an integrated circuitry, a specially designed application specific integrated circuits ("ASICs"), a piece of computer hardware, a firmware, a software application, and a combination thereof. These various implementations can include implementation in one or more computer programs that are executable and/or interpretable on a programmable system including one programmable processor, which may be special or general purpose, coupled to receive data and instructions from, and to transmit data and instructions to, a storage system, one input device, and one output device.

Various implementations of the systems and techniques described here can be realized in a digital electronic circuitry, an integrated circuitry, a specially designed application specific integrated circuits ("ASICs"), a piece of computer hardware, a firmware, a software application, and a combination thereof. These various implementations can include implementation in one or more computer programs that are executable and/or interpretable on a programmable system includes programmable processor, which may be special or general purpose, coupled to receive data and instructions from, and to transmit data and instructions to, a storage system, input device, and output device.

These computer programs (also known as programs, software, software applications, and/or code) comprise machine-readable instructions for a programmable processor, and can be implemented in a high-level procedural and/or object-oriented programming language, and/or in assembly/machine language. As used herein, the terms "machine-readable medium" and/or "computer-readable medium" refers to any computer program product, apparatus and/or device (e.g., magnetic discs, optical disks, memory, and/or Programmable Logic Devices ("PLDs")) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here may be implemented on a computing device having a display device (e.g., a cathode ray tube ("CRT") and/or liquid crystal ("LCD") monitor) for displaying information to the user and a keyboard and a mouse 924 by which the user can provide input to the computer. Other kinds of devices can be used to provide for interaction with a user as well; for example, feedback provided to the user can be any form of sensory feedback (e.g., visual feedback, auditory feedback, and/or tactile feedback) and input from the user can be received in any form, including acoustic, speech, and/or tactile input.

The systems and techniques described here may be implemented in a computing system that includes a back end component (e.g., as a data server), a middleware component (e.g., an application server), a front end component (e.g., a client computer having a graphical user interface, and/or a Web browser through which a user can interact with an implementation of the systems and techniques described here), and a combination thereof. The components of the system may also be coupled through a communication network.

The communication network may include a local area network ("LAN") and a wide area network ("WAN") (e.g., the Internet). The computing system can include a client and a server. In one implementation, the client and the server are remote from each other and interact through the communication network.

A number of implementations have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

It may be appreciated that the various systems, methods, and apparatus disclosed herein may be embodied in a machine-readable medium and/or a machine accessible medium compatible with a data processing system (e.g., a computer system), and/or may be performed in any order.

The structures and modules in the figures may be shown as distinct and communicating with only a few specific structures and not others. The structures may be merged with each other, may perform overlapping functions, and may communicate with other structures not shown to be connected in the figures.

The above-described functions and components may be comprised of instructions that are stored on a storage medium such as a computer readable medium. The instructions may be retrieved and executed by a processor. Some examples of instructions are software, program code, and firmware. Some examples of storage medium are memory devices, tapes, disks, integrated circuits, and servers. The instructions are operational when executed by the processor to direct the processor to operate in accord with some implementations. Those skilled in the art are familiar with instructions, processor(s), and storage medium.

What is claimed is:

1. A method comprising:
receiving current patient information of a first patient at a physical location, the physical location corresponding to a health facility used to assess the first patient for a medical condition;
collecting, automatically by one or more first automated agents using a plurality of application programming interfaces (APIs), first past patient information from the physical location and a plurality of disparate remote locations, wherein the plurality of disparate remote locations provide API communication and include a first electronic medical record (EMR) system and a social network, and wherein at least a portion of the first past patient information collected from the social network comprises global positioning system (GPS) information collected using a corresponding API of the plurality of APIs, and wherein the first past patient information is automatically pushed from the plurality of disparate remote locations to the one or more first automated agents using the plurality of APIs;
screen scraping, in response to determining a second EMR system does not provide API communication, a graphical user interface screen of the second EMR system, the screen scraping including:
reading the graphical user interface screen of the second EMR system;
determining how to interact with the read graphical user interface screen of the second EMR system;
executing, based on the determining how to interact with the read graphical user interface screen of the second EMR system, keyboard, mouse and other input instructions to automatically provide information to the graphical user interface screen of the second EMR system;
associating, based on the screen scraping, a local query to an entry point of the second EMR system;
associating, based on the screen scraping, a local input field to an input field of the second EMR system;
collecting, based on the screen scraping and the associating the local query to the entry point and the associating the local input field to the input field of the second EMR system, second past patient information from the second EMR system;
receiving one or more of current patient data and past patient data from one or more health sensors connected to the patient;
creating a patient profile for the first patient based on the current patient information, the first past patient information, the second past patient information, and the one or more of the current patient data and the past patient data, the patient profile including patient parameters corresponding to automated diagnosis patient archetype parameters;
comparing the patient profile to a super plurality of automated diagnosis patient archetypes, each of the super plurality of automated diagnosis patient archetypes corresponding to a medical condition, a plurality of the super plurality of automated diagnosis patient archetypes corresponding to one or more of the patient parameters;
ranking the plurality of automated diagnosis patient archetypes based upon a respective plurality of applicability scores of the plurality of automated diagnosis patient archetypes, wherein the applicability scores are based on comparing patient parameters to values associated with the plurality of automated diagnosis patient archetype parameters, and on one or more of statistical data and expert recommendations;
repeating one or more times:
obtaining a dynamic physician diagnosis at a first station, wherein the dynamic physician diagnosis can at least be changed in response to a set of the applicability scores;
mapping the physician diagnosis to a subset of the plurality of automated diagnosis patient archetypes;
employing a second automated agent to customize a user interface to emphasize order selections to support changing one or more of the applicability scores;
receiving order selections via the customized user interface;
updating the ranking of the plurality of automated diagnosis patient archetypes in response to orders results;
making the dynamic physician diagnosis available to a second station.

2. The method of claim 1, wherein the plurality of disparate remote locations include a health records datastore.

3. The method of claim 1, wherein the physical location is a first physical location, and wherein a portion of the first past patient information from the plurality of disparate remote locations are associated with a second physical location that is different than the first physical location.

4. The method of claim 1, wherein the physical location is associated with a first time, and wherein a portion of the first past patient information from the plurality of disparate remote locations are associated with the physical location and a second time different than the first time.

5. The method of claim 1, wherein the patient parameters include one or more of a geographic parameter, a demographic parameter, a psychographic parameter, and a behavioristic parameter.

6. The method of claim 1, further comprising presenting the ranking of the plurality of automated diagnosis patient archetypes prior to obtaining the dynamic physician diagnosis.

7. The method of claim 1, wherein the user interface is a graphical user interface customized to emphasize order selections in a human-readable manner.

8. The method of claim 1, wherein the orders include one or more of diagnostics tests, medications, patient care instructions, and referrals.

9. A system comprising a tangible computer-readable medium and one or more processors configured to execute instructions stored in the tangible computer-readable medium, the instructions when executed causing the system to:
receive current patient information of a first patient at a physical location, the physical location corresponding to a health facility used to assess the first patient for a medical condition;
collect, automatically by one or more first automated agents using a plurality of application programming interfaces (APIs), first past patient information from the physical location and a plurality of disparate remote locations, wherein the plurality of disparate remote locations provide API communication and include a first electronic medical record (EMR) system and a social network, and wherein at least a portion of the first past patient information collected from the social network comprises global positioning system (GPS) information collected using a corresponding API of the plurality of APIs, and wherein the first past patient information is automatically pushed from the plurality of disparate remote locations to the one or more first automated agents using the plurality of APIs;

screen scrape, in response to determining a second EMR system does not provide API communication, a graphical user interface screen of the second EMR system, the screen scraping including:
- reading the graphical user interface screen of the second EMR system;
- determining how to interact with the read graphical user interface screen of the second EMR system;
- executing, based on the determining how to interact with the read graphical user interface screen of the second EMR system, keyboard, mouse and other input instructions to automatically provide information to the graphical user interface screen of the second EMR system;

associate, based on the screen scraping, a local query to an entry point of the second EMR system;

associate, based on the screen scraping, a local input field to an input field of the second EMR system;

collect, based on the screen scraping and the associating the local query to the entry point and the associating the local input field to the input field of the second EMR system, second past patient information from the second EMR system;

receive one or more of current patient data and past patient data from one or more health sensors connected to the patient;

create a patient profile for the first patient based on the current patient information, the first past patient information, the second past patient information, and the one or more of the current patient data and the past patient data, the patient profile including patient parameters corresponding to automated diagnosis patient archetype parameters;

compare the patient profile to a super plurality of automated diagnosis patient archetypes, each of the super plurality of automated diagnosis patient archetypes corresponding to a medical condition, a plurality of the super plurality of automated diagnosis patient archetypes corresponding to one or more of the patient parameters;

rank the plurality of automated diagnosis patient archetypes based upon a respective plurality of applicability scores of the plurality of automated diagnosis patient archetypes, wherein the applicability scores are based on comparing patient parameters to values associated with the plurality of automated diagnosis patient archetype parameters, and on one or more of statistical data and expert recommendations;

repeat one or more times:
- obtaining a dynamic physician diagnosis at a first station, wherein the dynamic physician diagnosis can at least be changed in response to a set of the applicability scores;
- mapping the physician diagnosis to a subset of the plurality of automated diagnosis patient archetypes;
- employing a second automated agent to customize a user interface to emphasize order selections to support changing one or more of the applicability scores;
- receiving order selections via the customized user interface;
- updating the ranking of the plurality of automated diagnosis patient archetypes in response to orders results;

to make the dynamic physician diagnosis available to a second station.

10. The system of claim 9, wherein the plurality of disparate remote locations include a health records datastore.

11. The system of claim 9, wherein the physical location is a first physical location, and wherein a portion of the first past patient information from the plurality of disparate remote locations are associated with a second physical location that is different than the first physical location.

12. The system of claim 9, wherein the physical location is associated with a first time, and wherein a portion of the first past patient information from the plurality of disparate remote locations are associated with the physical location and a second time different than the first time.

13. The system of claim 9, wherein the patient parameters include one or more of a geographic parameter, a demographic parameter, a psychographic parameter, and a behavioristic parameter.

14. The system of claim 9, the instructions when executed further causing the system to present the ranking of the plurality of automated diagnosis patient archetypes prior to obtaining the dynamic physician diagnosis.

15. The system of claim 9, wherein the user interface is a graphical user interface customized to emphasize order selections in a human-readable manner.

16. The system of claim 9, wherein the orders include one or more of diagnostics tests, medications, patient care instructions, and referrals.

\* \* \* \* \*